(12) United States Patent
Walter et al.

(10) Patent No.: US 8,202,894 B2
(45) Date of Patent: Jun. 19, 2012

(54) MICROBIOCIDES

(75) Inventors: Harald Walter, Stein (CH); Daniel Stierli, Stein (CH); Hans Tobler, Basel (CH)

(73) Assignee: Syngenta Crop Protection LLC, Greensboro, NC (US)

( * ) Notice: Subject to any disclaimer, the term of this patent is extended or adjusted under 35 U.S.C. 154(b) by 70 days.

(21) Appl. No.: 12/665,349

(22) PCT Filed: Jun. 30, 2008

(86) PCT No.: PCT/EP2008/005343
§ 371 (c)(1),
(2), (4) Date: May 21, 2010

(87) PCT Pub. No.: WO2009/003672
PCT Pub. Date: Jan. 8, 2009

(65) Prior Publication Data
US 2010/0227898 A1    Sep. 9, 2010

(30) Foreign Application Priority Data

Jul. 2, 2007   (EP) .................................... 07012909
Mar. 11, 2008   (EP) .................................... 08004437

(51) Int. Cl.
| | |
|---|---|
| *A01N 43/40* | (2006.01) |
| *A01N 43/56* | (2006.01) |
| *A01N 43/50* | (2006.01) |
| *A01N 43/12* | (2006.01) |
| *A01P 1/00* | (2006.01) |
| *C07D 231/18* | (2006.01) |
| *C07D 409/06* | (2006.01) |
| *C07D 233/64* | (2006.01) |
| *C07D 333/52* | (2006.01) |

(52) U.S. Cl. ........ 514/357; 514/406; 514/397; 514/443; 546/280.4; 548/365.7; 548/315.1; 549/58

(58) Field of Classification Search .................. 514/357, 514/397, 443, 406; 548/364.1, 202, 255; 549/83
See application file for complete search history.

(56) References Cited

FOREIGN PATENT DOCUMENTS
| | | |
|---|---|---|
| WO | 2006108791 | 10/2006 |
| WO | 2007006739 | 1/2007 |
| WO | WO 2007006739 A1 * | 1/2007 |

\* cited by examiner

*Primary Examiner* — Yong Chu
(74) *Attorney, Agent, or Firm* — Kody Jones

(57) ABSTRACT

Compounds of the formula (I) in which the substituents are as defined in claim 1 are suitable for use as microbiocides.

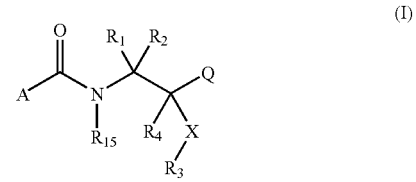

(I)

13 Claims, No Drawings

MICROBIOCIDES

This application is a 371 of International Application No. PCT/EP2008/005343 filed Jun. 30, 2008, which claims priority to EP 07012909.3 filed Jul. 2, 2007 and EP 08004437.3 filed Mar. 11, 2008, the contents of which are incorporated herein by reference.

The present invention relates to novel microbiocidally active, in particular fungicidally active, thienyl/benzthienyl ethyl amides. It further relates to intermediates used in the preparation of these compounds, to compositions which comprise these compounds and to their use in agriculture or horticulture for controlling or preventing infestation of plants by phytopathogenic microorganisms, preferably fungi.

Thienyl ethyl amides and their use as fungicides are described in WO 2006/108791 and EP 1710237 A1. Benzthienyl ethyl amides and their use as fungicides are described in WO 2007/006739.

It has been found that novel thienyl/benzthienyl ethyl amides have microbiocidal activity. The present invention thus provides compounds of the formula I

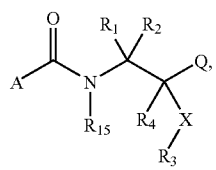
(I)

wherein
$R_1$, $R_2$ and $R_4$ independently of each other are hydrogen, halogen, $C_1$-$C_4$ alkyl or $C_1$-$C_4$ halogenalkyl;
X is oxygen, sulfur, —N($R_9$)— or —N($R_{10}$)—O—;
$R_9$ and $R_{10}$ independently of each other are hydrogen or $C_1$-$C_6$alkyl;
$R_3$ is $C_1$-$C_6$alkyl or $C_1$-$C_6$haloalkyl;
Q is $Q_1$

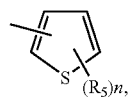
($Q_1$)

or Q is $Q_2$

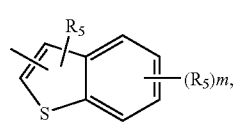
($Q_2$)

wherein
each $R_5$ independently of each other is halogen, $C_1$-$C_4$ alkyl, $C_1$-$C_4$ halogenalkyl, phenyl, halogenphenyl, $C_3$-$C_7$ cycloalkyl acetynyl, phenyl acetynyl or halogenphenyl acetynyl;
n is 1, 2 or 3;
m is 1, 2, 3 or 4;
A is a 5- or 6-membered heterocyclic ring containing one to three heteroatoms, each independently selected from oxygen, nitrogen and sulphur, or a phenyl ring; the heterocyclic ring or the phenyl being substituted by the groups $R_6$, $R_7$ and $R_8$;
$R_6$, $R_7$ and $R_8$ are each, independently, hydrogen, halogen, cyano, nitro, $C_{1-4}$ alkyl, $C_{1-4}$ halogenalkyl, $C_{1-4}$ halogenalkoxy, $C_{1-4}$ alkoxy($C_{1-4}$)alkyl or $C_{1-4}$ halogenalkoxy($C_{1-4}$) alkyl, provided that at least one of $R_6$, $R_7$ and $R_8$ is not hydrogen;
$R_{15}$ is hydrogen or $C_3$-$C_7$cycloalkyl;
and tautomers/isomers/enantiomers of these compounds.

According to the invention, the term "acetynyl", as used in the definition of substituent $R_5$, is the group "—C≡C—". As example, $C_3$ cycloalkyl acetynyl is the group

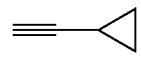

and is present, for example, as substituent $R_{5b}$ in compound 1.17.

The alkyl groups occurring in the definitions of the substituents can be straight-chain or branched and are, for example, methyl, ethyl, n-propyl, n-butyl, n-pentyl, n-hexyl, iso-propyl, n-butyl, sec-butyl, iso-butyl or tert-butyl. Alkoxy, alkenyl and alkynyl radicals are derived from the alkyl radicals mentioned. The alkenyl and alkynyl groups can be mono- or di-unsaturated.

The cycloalkyl groups occurring in the definitions of the substituents are, for example, cyclopropyl, cyclobutyl, cyclopentyl, cyclohexyl or cycloheptyl.

Halogen is generally fluorine, chlorine, bromine or iodine, preferably fluorine, bromine or chlorine. This also applies, correspondingly, to halogen in combination with other meanings, such as halogenalkyl or halogenalkoxy.

Halogenalkyl groups preferably have a chain length of from 1 to 4 carbon atoms. Halogenalkyl is, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl; preferably trichloromethyl, difluorochloromethyl, difluoromethyl, trifluoromethyl and dichlorofluoromethyl.

Alkoxy is, for example, methoxy, ethoxy, propoxy, i-propoxy, n-butoxy, isobutoxy, sec-butoxy and tert-butoxy; preferably methoxy and ethoxy. Halogenalkoxy is, for example, fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy and 2,2,2-trichloroethoxy; preferably difluoromethoxy, 2-chloroethoxy and trifluoromethoxy.

Alkoxyalkyl is, for example, methoxymethyl, methoxyethyl, ethoxymethyl, ethoxyethyl, n-propoxymethyl, n-propoxyethyl, isopropoxymethyl or isopropoxyethyl.

Halogenphenyl is preferably phenyl substituted by 1, 2 or 3 halogen atoms, for example 4-chloro-phenyl.

In the context of the present invention a "5- or 6-membered heterocyclic ring containing one to three heteroatoms, each independently selected from oxygen, nitrogen and sulphur" preferably means pyrazolyl (especially pyrazol-4-yl), thiazolyl (especially thiazol-5-yl), pyrrolyl (especially pyrrol-3-yl), 1,2,3 triazolyl, oxazolyl (especially oxazol-5-yl), pyridyl (especially pyrid-3-yl) or 2,3 dihydro-[1,4]oxathiinyl (especially 2,3 dihydro-[1,4]oxathiin-5-yl).

The compounds of formula I can occur in different isomeric forms; the invention covers all those isomers and mixtures thereof. The compounds of the formula I may occur in different tautomeric forms. For example, compounds of formula I exist in the tautomeric forms $I_I$ and $I_{II}$:

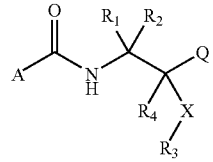

$I_I$

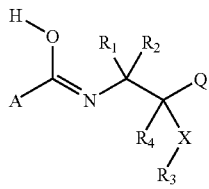

$I_{II}$

The invention covers all those tautomeric forms and mixtures thereof.

Preferred are compounds of formula I, wherein $R_{15}$ is hydrogen.

In a preferred group of compounds A is a 5-membered heterocyclic ring containing one to three heteroatoms, each independently selected from oxygen, nitrogen and sulphur; the heterocyclic ring being substituted by the groups $R_6$, $R_7$ and $R_8$.

Within said preferred group of compounds, further preferably A is $A_1$

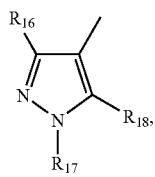

(A₁)

in which
$R_{16}$ is halogen, cyano, nitro, $C_1$-$C_4$alkyl, $C_1$-$C_4$halogenalkyl, $C_1$-$C_4$halogenalkoxy, $C_1$-$C_4$alkoxy-$C_1$-$C_4$alkyl or $C_1$-$C_4$halogenalkoxy-$C_1$-$C_4$alkyl;
$R_{17}$ is $C_1$-$C_4$alkyl, $C_1$-$C_4$halogenalkyl, $C_1$-$C_4$halogenalkoxy, $C_1$-$C_4$alkoxy-$C_1$-$C_4$alkyl or $C_1$-$C_4$halogenalkoxy-$C_1$-$C_4$alkyl; and
$R_{18}$ is hydrogen, halogen or cyano;
or A is $A_2$

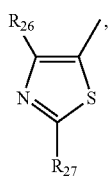

(A₂)

in which
$R_{26}$ is halogen, cyano, nitro, $C_1$-$C_4$alkyl, $C_1$-$C_4$halogenalkyl, $C_1$-$C_4$halogenalkoxy, $C_1$-$C_4$alkoxy-$C_1$-$C_4$alkyl or $C_1$-$C_4$halogenalkoxy-$C_1$-$C_4$alkyl; and
$R_{27}$ is $C_1$-$C_4$alkyl, $C_1$-$C_4$halogenalkyl, $C_1$-$C_4$halogenalkoxy, $C_1$-$C_4$alkoxy-$C_1$-$C_4$alkyl or $C_1$-$C_4$halogenalkoxy-$C_1$-$C_4$alkyl;

or A is $A_3$

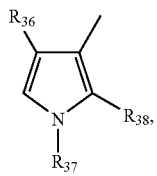

(A₃)

in which
$R_{36}$ is halogen, cyano, nitro, $C_1$-$C_4$alkyl, $C_1$-$C_4$halogenalkyl, $C_1$-$C_4$halogenalkoxy, $C_1$-$C_4$alkoxy-$C_1$-$C_4$alkyl or $C_1$-$C_4$halogenalkoxy-$C_1$-$C_4$alkyl;
$R_{37}$ is $C_1$-$C_4$alkyl, $C_1$-$C_4$halogenalkyl, $C_1$-$C_4$halogenalkoxy, $C_1$-$C_4$alkoxy-$C_1$-$C_4$alkyl or $C_1$-$C_4$halogenalkoxy-$C_1$-$C_4$alkyl; and
$R_{38}$ is hydrogen, halogen or cyano;
or A is $A_4$

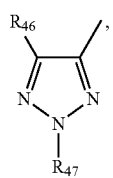

(A₄)

in which
$R_{46}$ and $R_{47}$ independently of one another are halogen, cyano, nitro, $C_1$-$C_4$alkyl, $C_1$-$C_4$halogenalkyl, $C_1$-$C_4$halogenalkoxy, $C_1$-$C_4$alkoxy-$C_1$-$C_4$alkyl or $C_1$-$C_4$halogenalkoxy-$C_1$-$C_4$alkyl.

Within said preferred group of compounds, further preferably A is $A_1$.

Within said preferred group of compounds, further preferably A is $A_2$.

Within said preferred group of compounds, further preferably A is $A_3$.

Within said preferred group of compounds, further preferably A is $A_4$.

In another preferred group of compounds A is a phenyl ring or a 6-membered heterocyclic ring containing one to three heteroatoms, each independently selected from oxygen, nitrogen and sulphur; the phenyl ring or the heterocyclic ring being substituted by the groups $R_6$, $R_7$ and $R_8$.

Within said preferred group of compounds, further preferably A is $A_5$

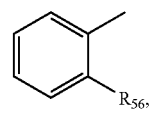

(A₅)

in which
$R_{56}$ is halogen, $C_1$-$C_4$halogenalkyl, $C_1$-$C_4$halogenalkoxy or $C_1$-$C_4$halogenalkoxy-$C_1$-$C_4$alkyl;

or A is $A_6$

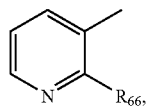

(A₆)

in which
$R_{66}$ is halogen, cyano, nitro, $C_1$-$C_4$alkyl, $C_1$-$C_4$halogenalkyl, $C_1$-$C_4$alkoxy-$C_1$-$C_4$alkyl or $C_1$-$C_4$halogenalkoxy-$C_1$-$C_4$alkyl;
or A is $A_7$

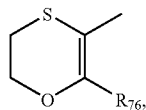

(A₇)

in which
$R_{76}$ is $C_1$-$C_4$alkyl or $C_1$-$C_4$halogenalkyl.

Within said preferred group of compounds, further preferably A is $A_5$.

Within said preferred group of compounds, further preferably A is $A_6$.

Within said preferred group of compounds, further preferably A is $A_7$.

In a particular preferred group of compounds A is $A_1$, wherein $R_{18}$ is hydrogen. In another particular preferred group of compounds A is $A_1$, wherein $R_{16}$ is $C_1$-$C_4$alkyl or $C_1$-$C_4$halogenalkyl, preferably $C_1$-$C_4$halogenalkyl; $R_{17}$ is $C_1$-$C_4$alkyl; and $R_{18}$ is hydrogen or halogen, preferably hydrogen.

In another particular preferred group of compounds A is $A_2$, wherein $R_{26}$ is $C_1$-$C_4$alkyl or $C_1$-$C_4$halogenalkyl; and $R_{27}$ is $C_1$-$C_4$alkyl.

In yet another particular preferred group of compounds A is $A_3$, wherein $R_{36}$ is $C_1$-$C_4$alkyl or $C_1$-$C_4$halogenalkyl; $R_{37}$ is $C_1$-$C_4$alkyl; and $R_{38}$ is hydrogen or halogen.

In yet another particular preferred group of compounds A is $A_4$, wherein $R_{46}$ is $C_1$-$C_4$alkyl or $C_1$-$C_4$halogenalkyl; and $R_{47}$ is $C_1$-$C_4$alkyl.

In yet another particular preferred group of compounds A is $A_4$, wherein $R_{46}$ halogenmethyl, preferably $R_{46}$ is selected from $CF_3$, $CF_2H$ and $CFH_2$; and $R_{47}$ is $C_1$-$C_4$alkyl.

In yet another particular preferred group of compounds A is $A_5$, wherein $R_{56}$ is halogen or $C_1$-$C_4$halogenalkyl.

In yet another particular preferred group of compounds A is $A_6$, wherein $R_{66}$ is halogen or $C_1$-$C_4$halogenalkyl.

In yet another particular preferred group of compounds A is $A_7$, wherein $R_{76}$ is $C_1$-$C_4$alkyl or $C_1$-$C_4$halogenalkyl.

In a preferred group of compounds $R_1$, $R_2$ and $R_4$ independently of each other is hydrogen or methyl. In one embodiment, $R_2$ and $R_4$ are both hydrogen and $R_1$ is methyl. In one embodiment, $R_1$, $R_2$ and $R_4$ are all hydrogen.

In a preferred group of compounds X is oxygen or sulfur.
In a preferred group of compounds X is oxygen.
In a further preferred group of compounds X is sulfur.
In yet a further preferred group of compounds X is —N($R_9$)—.

In yet a further preferred group of compounds X is —N($R_{10}$)—O—.

In a preferred group of compounds $R_3$ is $C_1$-$C_6$alkyl, preferably methyl or ethyl. In one embodiment, $R_3$ is methyl. In another embodiment, $R_3$ is ethyl.

In one embodiment Q is $Q_1$ (thienyl ethyl amides).
In one embodiment $Q_1$ is $Q_{1A}$

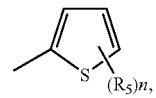

($Q_{1A}$)

wherein $R_5$ and n are as defined under formula I (thien-2-yl ethyl amides).

Preferably, $Q_{1A}$ is $Q_{1A-1}$

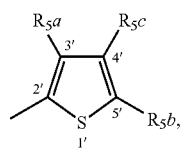

($Q_{1A-1}$)

wherein $R_{5a}$ is halogen, $C_1$-$C_4$ alkyl, $C_1$-$C_4$ halogenalkyl, phenyl, halogenphenyl, $C_3$-$C_7$ cycloalkyl acetynyl, phenyl acetynyl or halogenphenyl acetynyl; $R_{5b}$ is halogen, $C_1$-$C_4$ alkyl, $C_1$-$C_4$ halogenalkyl, phenyl, halogenphenyl, $C_3$-$C_7$ cycloalkyl acetynyl, phenyl acetynyl or halogenphenyl acetynyl; and $R_{5c}$ is hydrogen, halogen, $C_1$-$C_4$ alkyl, $C_1$-$C_4$ halogenalkyl, phenyl, halogenphenyl, $C_3$-$C_7$ cycloalkyl acetynyl, phenyl acetynyl or halogenphenyl acetynyl.

In yet more preferred compounds within this embodiment, $R_{5a}$ is halogen, more preferably chloro; $R_{5b}$ is halogen, phenyl, halogenphenyl, $C_3$-$C_7$ cycloalkyl acetynyl, phenyl acetynyl or halogenphenyl acetynyl; and $R_{5c}$ is hydrogen. These compounds are shown in tables 1 to 13.

In one embodiment $Q_1$ is $Q_{1B}$

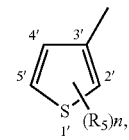

($Q_{1B}$)

wherein $R_5$ and n are as defined under formula I (thien-3-yl ethyl amides).

Preferably, $Q_{1B}$ is $Q_{1B-1}$

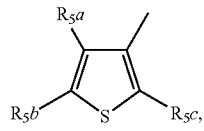

($Q_{1B-1}$)

wherein $R_{5a}$ is halogen, $C_1$-$C_4$ alkyl, $C_1$-$C_4$ halogenalkyl, phenyl, halogenphenyl, $C_3$-$C_7$ cycloalkyl acetynyl, phenyl acetynyl or halogenphenyl acetynyl; $R_{5b}$ is halogen, $C_1$-$C_4$ alkyl, $C_1$-$C_4$ halogenalkyl, phenyl, halogenphenyl, $C_3$-$C_7$ cycloalkyl acetynyl, phenyl acetynyl or halogenphenyl acetynyl; and $R_{5c}$ is halogen, $C_1$-$C_4$ alkyl, $C_1$-$C_4$ halogenalkyl, phenyl, halogenphenyl, $C_3$-$C_7$ cycloalkyl acetynyl, phenyl acetynyl or halogenphenyl acetynyl.

In more preferred compounds within this embodiment, $R_{5a}$ and $R_{5b}$ are both independently from each other halogen, more preferably chloro; and $R_{5c}$ is halogen, $C_1$-$C_4$ alkyl, $C_1$-$C_4$ halogenalkyl, phenyl, halogenphenyl, $C_3$-$C_7$ cycloalkyl acetynyl, phenyl acetynyl or halogenphenyl acetynyl. These compounds are shown in tables 14 to 20.

In further more preferred compounds within this embodiment, $R_{5a}$ and $R_{5c}$ are both independently from each other halogen, more preferably chloro; and $R_{5b}$ is halogen, $C_1$-$C_4$ alkyl, $C_1$-$C_4$ halogenalkyl, phenyl, halogenphenyl, $C_3$-$C_7$ cycloalkyl acetynyl, phenyl acetynyl or halogenphenyl acetynyl. Also these compounds are shown in tables 14 to 20.

In one embodiment Q is $Q_2$ (benzthienyl ethyl amides).

In one embodiment $Q_2$ is $Q_{2A}$

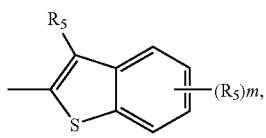

($Q_{2A}$)

wherein $R_5$ and m are as defined under formula I (benzthien-2-yl ethyl amides).

Preferably, $Q_{2A}$ is $Q_{2A-1}$

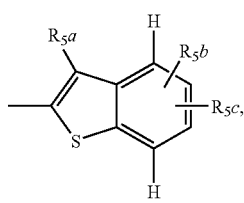

($Q_{2A-1}$)

wherein $R_{5a}$ and $R_{5b}$ are each independently from each other halogen, $C_1$-$C_4$ alkyl, $C_1$-$C_4$ halogenalkyl, phenyl, halogenphenyl, $C_3$-$C_7$ cycloalkyl acetynyl, phenyl acetynyl or halogenphenyl acetynyl; and $R_{5c}$ is hydrogen, halogen, $C_1$-$C_4$ alkyl, $C_1$-$C_4$ halogenalkyl, phenyl, halogenphenyl, $C_3$-$C_7$ cycloalkyl acetynyl, phenyl acetynyl or halogenphenyl acetynyl.

In yet more preferred compounds within this embodiment, $R_{5a}$ is halogen, more preferably chloro; $R_{5b}$ is halogen, phenyl, halogenphenyl, $C_3$-$C_7$ cycloalkyl acetynyl, phenyl acetynyl or halogenphenyl acetynyl; and $R_{5c}$ is hydrogen. In one embodiment, $R_{5b}$ is in the 5'-position of the benzthiophene. In another embodiment, $R_{5b}$ is in the 6'-position of the benzthiophene. These embodiments is represented by compounds of tables 21 to 33.

In one embodiment, $Q_2$ is $Q_{2B}$

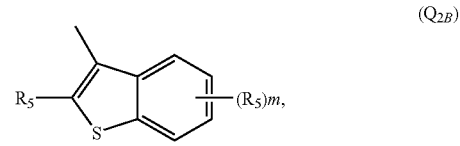

($Q_{2B}$)

wherein $R_5$ and m are as defined under formula I (benzthien-3-yl ethyl amides).

Preferably, $Q_{2B}$ is $Q_{2B-1}$

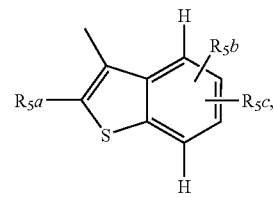

($Q_{2B-1}$)

wherein $R_{5a}$ and $R_{5b}$ are each independently from each other halogen, $C_1$-$C_4$ alkyl, $C_1$-$C_4$ halogenalkyl, phenyl, halogenphenyl, $C_3$-$C_7$ cycloalkyl acetynyl, phenyl acetynyl or halogenphenyl acetynyl; and $R_{5c}$ is hydrogen, halogen, $C_1$-$C_4$ alkyl, $C_1$-$C_4$ halogenalkyl, phenyl, halogenphenyl, $C_3$-$C_7$ cycloalkyl acetynyl, phenyl acetynyl or halogenphenyl acetynyl.

In yet more preferred compounds within this embodiment, $R_{5a}$ is halogen, more preferably chloro; $R_{5b}$ is halogen, phenyl, halogenphenyl, $C_3$-$C_7$ cycloalkyl acetynyl, phenyl acetynyl or halogenphenyl acetynyl; and $R_{5c}$ is hydrogen.

The preparation of compounds of formula I, wherein $R_{15}$ is hydrogen, is shown below. Compounds of formula I, wherein Q is $Q_{1A-1}$; $R_2$ and $R_4$ are both hydrogen; $R_{5a}$ and $R_{5b}$ are both independently from each other chloro or bromo; and $R_{5c}$ is hydrogen (compounds of formula IA according to scheme 1) may be prepared according to scheme 1.

Scheme 1:

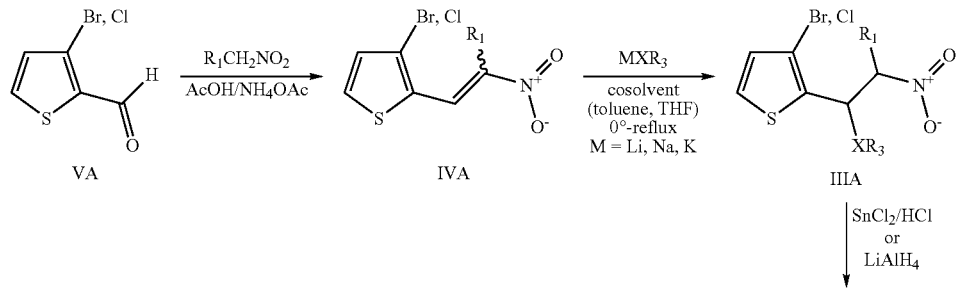

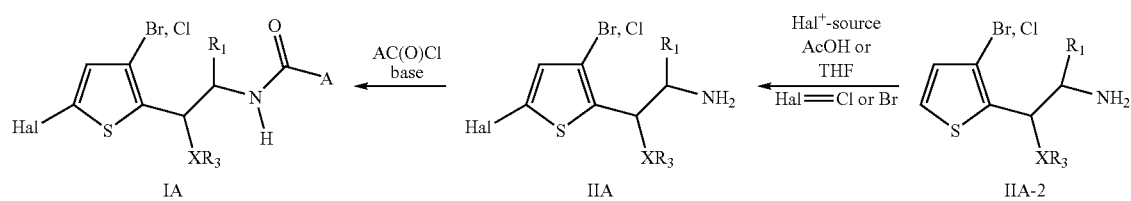

A thiophene-2-aldehyde of formula VA can be reacted with a nitroalkane of the formula $R_1CH_2NO_2$, wherein $R_1$ is as defined under formula I to form the nitroalkenes of formula IVA, in which $R_1$ is as defined under formula I. Said reaction is carried out conveniently in the presence of acetic acid and ammonium acetate at temperatures between ambient temperature and reflux temperature.

The nitroalkene of formula IVA can be reacted with a compound of the formula $MXR_3$, wherein M is Li, Na or K; X and $R_3$ is as defined under formula I, to form the nitroalkanes of formula IIIA, in which X, $R_1$ and $R_3$ are as defined under formula I.

The nitroalkanes of formula IIIA can be reduced to the amines of formula IIA-2, wherein X, $R_1$ and $R_3$ are as defined under formula IIIA, by using, for example, $LiAlH_4$ in an ether solvent, such as diethylether or tetrahydrofurane.

The amines of formula IIA-2 can be chlorinated or brominated, for example with bromine in the presence of acetic acid, to the amines of formula IIA, wherein Hal is chloro or bromo; and X, $R_1$ and $R_3$ are as defined under formula IIIA.

The halogenated amines of formula IIA can be amidated by using the corresponding acid derivatives, such as acid chlorides of the formula A-C(O)Cl, wherein A is as defined under formula I, to form the halogenated amides of formula IA. Said amidations are conveniently carried out in the presence of a base, such as triethylamine, Hunig base, sodium bicarbonate, sodium carbonate, potassium carbonate, pyridine or quinoline, but preferably triethylamine, and in a solvent, such as diethylether, TBME, THF, dichloromethane, chloroform, DMF or NMP, for between 10 minutes and 48 hours, preferably 12 to 24 hours, and between 0° C. and reflux, preferably 20 to 25° C.

Compounds of formula I, wherein Q is $Q_{1A-1}$; $R_2$ and $R_4$ are both hydrogen; $R_{5a}$ is chloro or bromo; and $R_{5b}$ is phenyl, halogenphenyl, $C_3$-$C_7$ cycloalkyl acetynyl, phenyl acetynyl or halogenphenyl acetynyl (compounds of formula IA-2 or IA-3 according to scheme 2) may be prepared according to scheme 2.

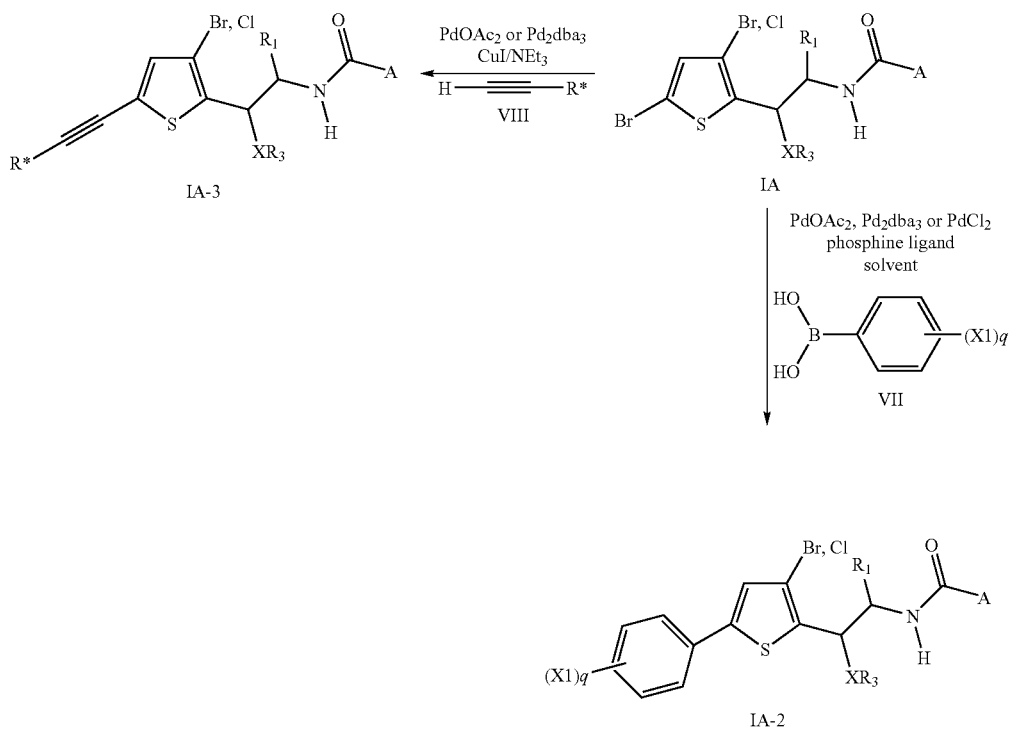

Compounds of formula IA-2, wherein A, X, $R_1$ and $R_3$ are as defined under formula IA and X1 is halogen and q is 0, 1, 2, 3, 4 or 5, may be prepared by reacting an amide of formula IA, wherein A, X, $R_1$ and $R_3$ are as defined under formula IA and Hal is bromo with a compound of formula VII, wherein X1 is halogen and q is 0, 1, 2, 3, 4 or 5, preferably 0 or 1, using the well known Suzuki coupling methodology. The Suzuki reaction has also become one of the standard methods for the direct coupling of two aromatic ring systems and is described, for example, in Journal of the American Chemical Society 121(41), 9550 (1999) and in Journal für Praktische Chemie 342(4), 334-339 (2000).

Compounds of the formula IA-3, wherein A, X, $R_1$ and $R_3$ are as defined under formula IA and R* is $C_3$-$C_7$ cycloalkyl, phenyl or halogenphenyl, may be prepared reacting an amide of formula IA, wherein A, X, $R_1$ and $R_3$ are as defined under formula IA and Hal is bromo with an acetynyl compound of the formula VIII, wherein R* is $C_3$-$C_7$ cycloalkyl, phenyl or halogenphenyl, using the well known Sonogashira coupling methodology. The Sonogashira reaction has become one of the standard methods for introducing an alkynyl function into unsaturated and aromatic or heteroaromatic molecules. It is reviewed, for example, in the *Handbook of Organopalladium Chemistry for Organic Synthesis* Vol. 1, 767-789 (2002); by I. B. Campbell in *Organocopper reagents* (IRL-Press, 1994); by K. C. Nicolaou et. al. in *Angewandte Chemie Int. Ed.*, 44, 4442 (2005); by R. Tykwinski et. al., ibid. 42, 1433 (2002); and by A. Zapf et. al. in *Topics in Catalysis*, 19, 101 (2002).

Compounds of formula I, wherein Q is $Q_{1B-1}$; $R_2$ and $R_4$ are both hydrogen; $R_{5a}$ and $R_{5b}$ are both chloro; and $R_{5c}$ is bromo as well as compounds of formula I, wherein Q is $Q_{1B-1}$; $R_2$ and $R_4$ are both hydrogen; $R_{5a}$ and $R_{5c}$ are both chloro; and $R_{5b}$ is bromo (compounds of formulae IB-1 and IB-2 according to scheme 3a) may be prepared according to scheme 3a.

Thiophene-3-aldehyde (compound of formula VIB) can be exhaustively chlorinated with $Cl_2/AlCl_3$ according to known methods to generate the tri-chlorinated thiophene aldehyde of formula VB.

The compound of formula VB can be reacted with a nitroalkane of the formula $R_1CH_2NO_2$, wherein $R_1$ is as defined under formula I to form the nitroalkene of formula IVB, in which $R_1$ is as defined under formula I.

The nitroalkene of the formula IVB can be reacted with a compound of the formula $MXR_3$, wherein M is Li, Na or K; X and $R_3$ is as defined under formula I to form the nitroalkanes of formula IIIB, in which X, $R_1$ and $R_3$ are as defined under formula I.

The nitroalkanes of formula IIIB can be reduced to the di-chlorinated amines of formulae IIB-3 and IIB-4, in which X, $R_1$ and $R_3$ are as defined under formula I. Subsequently the amines of formulae IIB-3 and IIB-4 can be brominated to form the amines of formulae IIB-1 and IIB-2, in which X, $R_1$ and $R_3$ are as defined under formula I.

The brominated amines of formulae IIB-1 and IIB-2 can be amidated by using the corresponding acid derivatives, such as acid chlorides of the formula A-C(O)Cl, wherein A is as defined under formula I, to form the brominated amides of formulae IB-1 and IB-2, wherein X, A, $R_1$ and $R_3$ are as defined under formula I.

Compounds of formula IB-1 can be prepared according to Scheme 3b:

Scheme 3a:

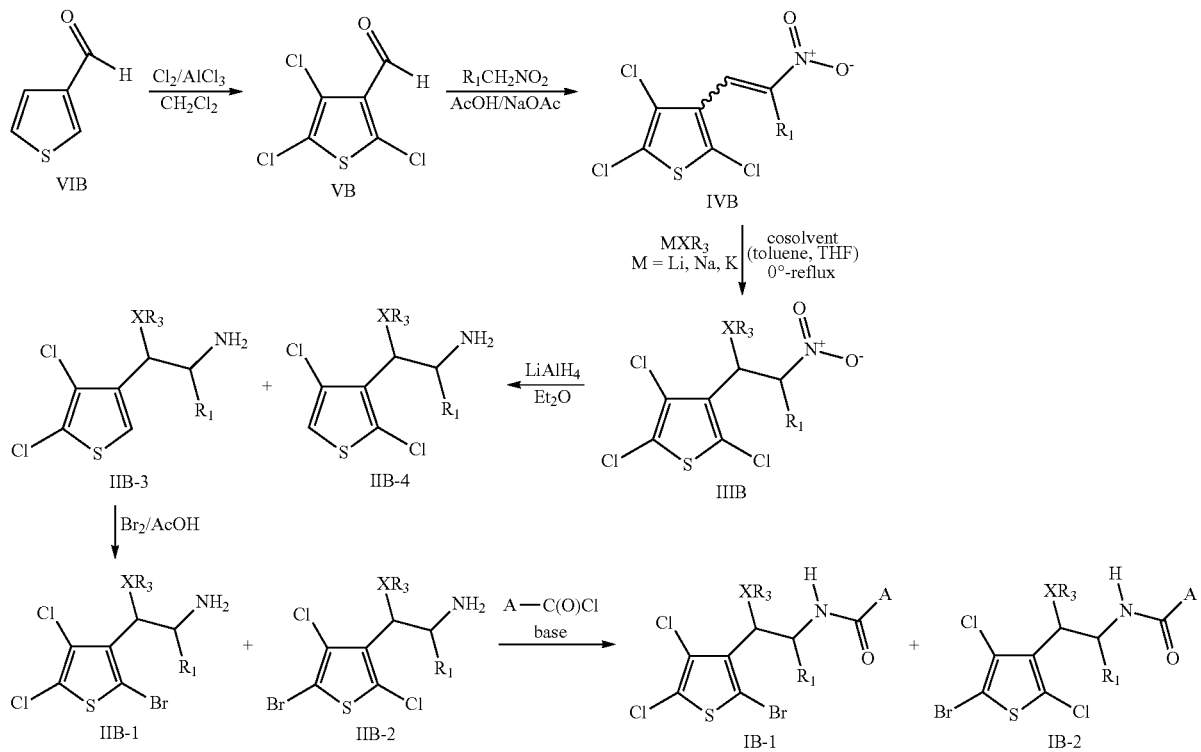

Scheme 3b:

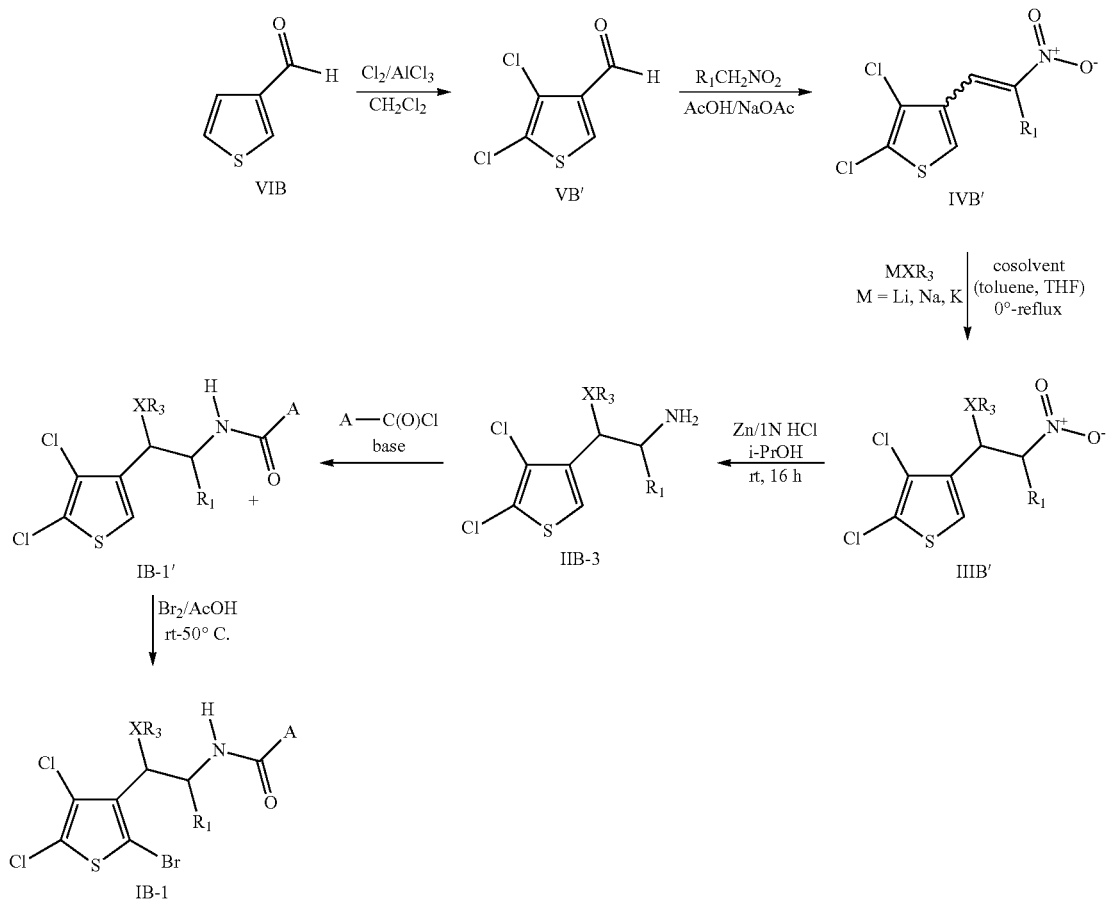

Compounds of the formulae IB-3 and IB-4

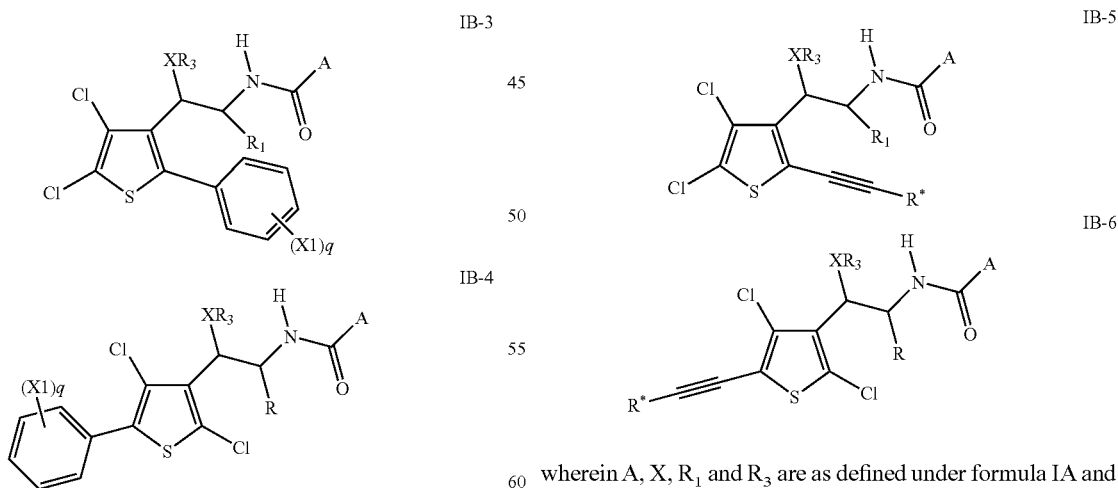

wherein A, X, $R_1$ and $R_3$ are as defined under formula IA and X1 is halogen and q is 0, 1, 2, 3, 4 or 5, may be prepared by reacting the brominated amines of formulae IB-1 and IB-2 with a compound of formula VII via the above-described Suzuki reaction.

Compounds of the formulae IB-5 and IB-6 wherein A, X, $R_1$ and $R_3$ are as defined under formula IA and R* is $C_3$-$C_7$ cycloalkyl, phenyl or halogenphenyl, may be prepared by reacting the brominated amines of formulae IB-1 and IB-2 with an acetynyl compound of the formula VIII using the well known Sonogashira coupling methodology as described above.

Compounds of formulae IIB-1/IIB-2, IIB-3/IIB-4, IB-1/IB-2, IB-3/IB-4 and IB-5/IB-6 can be separated by HPLC.

Compounds of formula I, wherein Q is $Q_{24-1}$, $R_{5a}$ is chloro; and $R_2$ and $R_4$ are both hydrogen (compounds of formula IC according to scheme 4) may be prepared according to scheme 4.

Scheme 4:

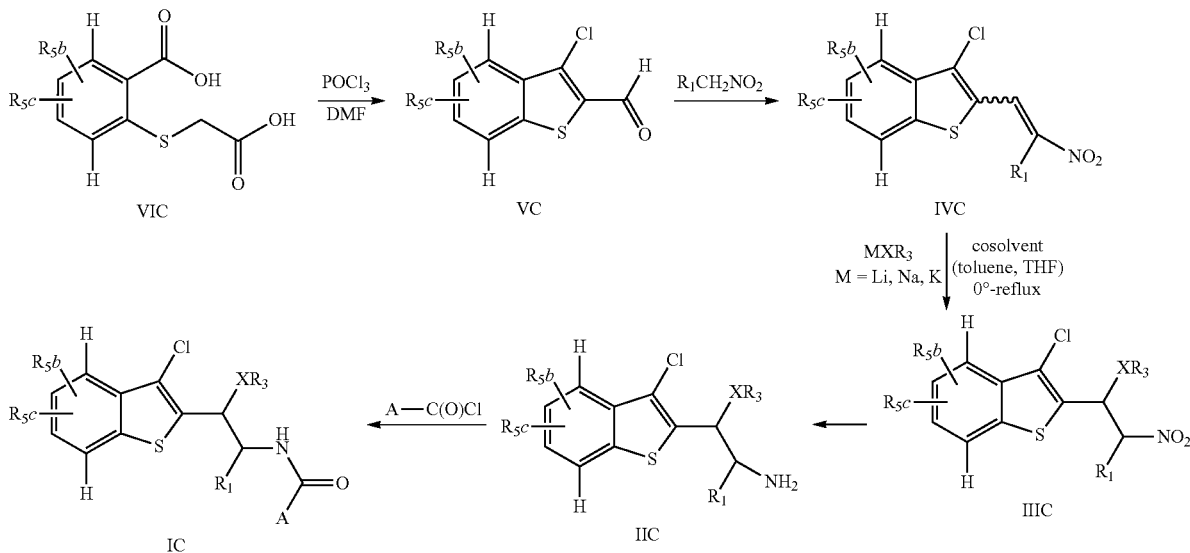

Benzthiophenes of formula VC, wherein $R_{5b}$ and $R_{5c}$ are as defined under formula I, can be prepared from compounds of formula VIC, wherein $R_{5b}$ and $R_{5c}$ are as defined under formula I, as described in J. Org. Chem. 1996, 61(9), 6523-25.

Starting from the benzthiophenes of formula VC, the compounds of formulae IVC, IIIC, IIC and IC, wherein X, A, $R_1$, $R_3$, $R_{5b}$ and $R_{5c}$ are as defined under formula I, can be prepared as described above for scheme 1.

Compounds of formula IC, wherein $R_{5b}$ is phenyl, halogenphenyl, $C_3$-$C_7$ cycloalkyl acetynyl, phenyl acetynyl or halogenphenyl acetynyl; and $R_{5c}$ is hydrogen, may be prepared by reacting a compound of formula IC, wherein $R_{5b}$ is bromo and $R_{5c}$ is hydrogen, with a compound of formula VII or VIII as described above for scheme 1 via the Suzuki reaction or Sonogashira reaction.

The compounds of the formulae VA, VII, VIII, VIB and VIC, wherein the substituents as described above, and the compounds of formulae $R_1CH_2NO_2$ and $MXR_3$, wherein $R_1$ and $R_3$ are as defined under formula I; and M is Li, Na or K, are known and commercially available or can be prepared according to the above-mentioned references or according to methods known in the art.

Compounds of the formula A-C(O)Cl are known and partially commercially available. They can be prepared analogously as described, for example, in WO 00/09482, WO 02/38542, WO 04/018438, EP-0-589-301, WO 93/11117 and Arch. Pharm. Res. 2000, 23(4), 315-323. Compounds of formula I, wherein $R_{15}$ is $C_3$-$C_7$cycloalkyl, can be for example prepared according to the following reaction scheme:

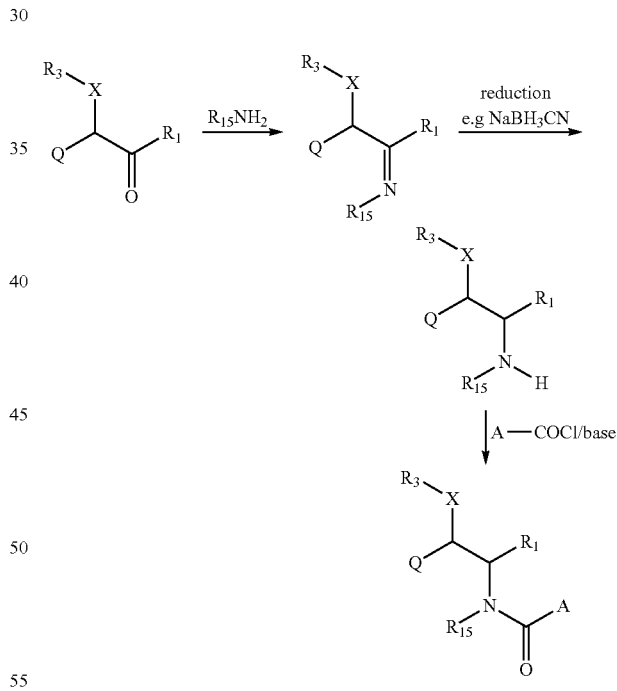

For preparing all further compounds of the formula I functionalized according to the definitions of A, Q, X, $R_1$, $R_2$, $R_3$ and $R_4$, there are a large number of suitable known standard methods, such as alkylation, halogenation, acylation, amidation, oximation, oxidation and reduction. The choice of the preparation methods which are suitable are depending on the properties (reactivity) of the substituents in the intermediates.

The reactions to give compounds of the formula I are advantageously carried out in aprotic inert organic solvents. Such solvents are hydrocarbons such as benzene, toluene, xylene or cyclohexane, chlorinated hydrocarbons such as dichloromethane, trichloromethane, tetrachloromethane or chlorobenzene, ethers such as diethyl ether, ethylene glycol dimethyl ether, diethylene glycol dimethyl ether, tetrahydrofuran or dioxane, nitriles such as acetonitrile or propionitrile, amides such as N,N-dimethylformamide, diethylformamide or N-methylpyrrolidinone. The reaction temperatures are advantageously between −20° C. and +120° C. In general, the reactions are slightly exothermic and, as a rule, they can be carried out at room temperature. To shorten the reaction time, or else to start the reaction, the mixture may be heated briefly to the boiling point of the reaction mixture. The reaction times can also be shortened by adding a few drops of base as reaction catalyst. Suitable bases are, in particular, tertiary amines such as trimethylamine, triethylamine, quinuclidine, 1,4-diazabicyclo[2.2.2]octane, 1,5-diazabicyclo[4.3.0]non-5-ene or 1,5-diazabicyclo-[5.4.0]undec-7-ene. However, inorganic bases such as hydrides, e.g. sodium hydride or calcium hydride, hydroxides, e.g. sodium hydroxide or potassium hydroxide, carbonates such as sodium carbonate and potassium carbonate, or hydrogen carbonates such as potassium hydrogen carbonate and sodium hydrogen carbonate may also be used as bases. The bases can be used as such or else with catalytic amounts of a phase-transfer catalyst, for example a crown ether, in particular 18-crown-6, or a tetraalkylammonium salt.

The compounds of formula I can be isolated in the customary manner by concentrating and/or by evaporating the solvent and purified by recrystallization or trituration of the solid residue in solvents in which they are not readily soluble, such as ethers, aromatic hydrocarbons or chlorinated hydrocarbons.

The compounds I and, where appropriate, the tautomers thereof, can be present in the form of one of the isomers which are possible or as a mixture of these, for example in the form of pure isomers, such as antipodes and/or diastereomers, or as isomer mixtures, such as enantiomer mixtures, for example racemates, diastereomer mixtures or racemate mixtures, depending on the number, absolute and relative configuration of asymmetric carbon atoms which occur in the molecule and/or depending on the configuration of non-aromatic double bonds which occur in the molecule; the invention relates to the pure isomers and also to all isomer mixtures which are possible and is to be understood in each case in this sense hereinabove and hereinbelow, even when stereochemical details are not mentioned specifically in each case.

The compounds I and, where appropriate, the tautomers thereof, can, if appropriate, also be obtained in the form of hydrates and/or include other solvents, for example those which may have been used for the crystallization of compounds which are present in solid form.

The intermediates of the formula II

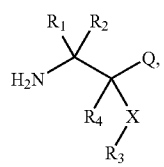

(II)

in which Q, X, $R_1$, $R_2$, $R_3$ and $R_4$ are as defined under formula I, are novel and were developed specifically for the preparation of the compounds of the formula I. Accordingly, these intermediates of the formula II also form part of the subject-matter of the present invention.

A preferred group of intermediates of the formula II are compounds of the formula IIA or IIA-2.

A further preferred group of intermediates of the formula II are compounds of the formula IIB-1, IIB-2, IIB-3 or IIB-4.

A further preferred group of intermediates of the formula II are compounds of the formula IIC.

Also the intermediates of the formula III

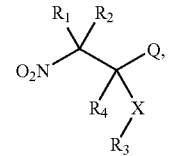

(III)

in which Q, X, $R_1$, $R_2$, $R_3$ and $R_4$ are as defined under formula I, are novel and were developed specifically for the preparation of the compounds of the formula I. Accordingly, these intermediates of the formula III also form part of the subject-matter of the present invention.

A preferred group of intermediates of the formula III are compounds of the formula IIIA.

A further preferred group of intermediates of the formula III are compounds of the formula IIIB.

A further preferred group of intermediates of the formula III are compounds of the formula IIIC.

It has now been found that the compounds of formula I according to the invention have, for practical purposes, a very advantageous spectrum of activities for protecting useful plants against diseases that are caused by phytopathogenic microorganisms, such as fungi, bacteria or viruses.

The invention relates to a method of controlling or preventing infestation of useful plants by phytopathogenic microorganisms, wherein a compound of formula I is applied as active ingredient to the plants, to parts thereof or the locus thereof. The compounds of formula I according to the invention are distinguished by excellent activity at low rates of application, by being well tolerated by plants and by being environmentally safe. They have very useful curative, preventive and systemic properties and are used for protecting numerous useful plants. The compounds of formula I can be used to inhibit or destroy the diseases that occur on plants or parts of plants (fruit, blossoms, leaves, stems, tubers, roots) of different crops of useful plants, while at the same time protecting also those parts of the plants that grow later e.g. from phytopathogenic microorganisms.

It is also possible to use compounds of formula I as dressing agents for the treatment of plant propagation material, in particular of seeds (fruit, tubers, grains) and plant cuttings (e.g. rice), for the protection against fungal infections as well as against phytopathogenic fungi occurring in the soil.

Furthermore the compounds of formula I according to the invention may be used for controlling fungi in related areas, for example in the protection of technical materials, including wood and wood related technical products, in food storage or in hygiene management.

The compounds of formula I are, for example, effective against the phytopathogenic fungi of the following classes: Fungi imperfecti (e.g. *Botrytis*, *Pyricularia*, *Helminthosporium*, *Fusarium*, *Septoria*, *Cercospora* and *Alternaria*) and Basidiomycetes (e.g. *Rhizoctonia*, *Hemileia*, *Puccinia*). Additionally, they are also effective against the Ascomycetes classes (e.g. *Venturia* and *Erysiphe*, *Podosphaera*, *Monilinia*, *Uncinula*) and of the Oomycetes classes (e.g. *Phytophthora*, *Pythium*, *Plasmopara*). Outstanding activity has been observed against powdery mildew (*Erysiphe* spp.). Furthermore, the novel compounds of formula I are effective against phytopathogenic bacteria and viruses (e.g. against *Xanthomonas* spp, *Pseudomonas* spp, *Erwinia amylovora* as well as against the tobacco mosaic virus). Good activity has been observed against Asian soybean rust (*Phakopsora pachyrhizi*).

Within the scope of the invention, useful plants to be protected typically comprise the following species of plants: cereal (wheat, barley, rye, oat, rice, maize, sorghum and related species); beet (sugar beet and fodder beet); pomes, drupes and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts); cucumber plants (pumpkins, cucumbers, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocado, *cinnamomum*, camphor) or plants such as tobacco, nuts, coffee, eggplants, sugar cane, tea, pepper, vines, hops, bananas and natural rubber plants, as well as ornamentals.

The term "useful plants" is to be understood as including also useful plants that have been rendered tolerant to herbicides like bromoxynil or classes of herbicides (such as, for example, HPPD inhibitors, ALS inhibitors, for example primisulfuron, prosulfuron and trifloxysulfuron, EPSPS (5-enol-pyrovyl-shikimate-3-phosphate-synthase) inhibitors, GS (glutamine synthetase) inhibitors or PPO (protoporphyrinogen-oxidase) inhibitors) as a result of conventional methods of breeding or genetic engineering. An example of a crop that has been rendered tolerant to imidazolinones, e.g. imazamox, by conventional methods of breeding (mutagenesis) is Clearfield® summer rape (Canola). Examples of crops that have been rendered tolerant to herbicides or classes of herbicides by genetic engineering methods include glyphosate- and glufosinate-resistant maize varieties commercially available under the trade names RoundupReady®, Herculex I® and LibertyLink®.

The term "useful plants" is to be understood as including also useful plants which have been so transformed by the use of recombinant DNA techniques that they are capable of synthesising one or more selectively acting toxins, such as are known, for example, from toxin-producing bacteria, especially those of the genus *Bacillus*.

The term "useful plants" is to be understood as including also useful plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818, and EP-A-0 353 191. The methods of producing such transgenic plants are generally known to the person skilled in the art and are described, for example, in the publications mentioned above.

The term "locus" of a useful plant as used herein intended to embrace the place on which the useful plants are growing, where the plant propagation materials of the useful plants are sown or where the plant propagation materials of the useful plants will be placed into the soil. An example for such a locus is a field, on which crop plants are growing.

The term "plant propagation material" is understood to denote generative parts of the plant, such as seeds, which can be used for the multiplication of the latter, and vegetative material, such as cuttings or tubers, for example potatoes. There may be mentioned for example seeds (in the strict sense), roots, fruits, tubers, bulbs, rhizomes and parts of plants. Germinated plants and young plants which are to be transplanted after germination or after emergence from the soil, may also be mentioned. These young plants may be protected before transplantation by a total or partial treatment by immersion. Preferably "plant propagation material" is understood to denote seeds.

The compounds of formula I can be used in unmodified form or, preferably, together with carriers and adjuvants conventionally employed in the art of formulation.

Therefore the invention also relates to compositions for controlling and protecting against phytopathogenic microorganisms, comprising a compound of formula I and an inert carrier, and to a method of controlling or preventing infestation of useful plants by phytopathogenic microorganisms, wherein a composition, comprising a compound of formula I as active ingredient and an inert carrier, is applied to the plants, to parts thereof or the locus thereof.

To this end compounds of formula I and inert carriers are conveniently formulated in known manner to emulsifiable concentrates, coatable pastes, directly sprayable or dilutable solutions, dilute emulsions, wettable powders, soluble powders, dusts, granulates, and also encapsulations e.g. in polymeric substances. As with the type of the compositions, the methods of application, such as spraying, atomising, dusting, scattering, coating or pouring, are chosen in accordance with the intended objectives and the prevailing circumstances. The compositions may also contain further adjuvants such as stabilizers, antifoams, viscosity regulators, binders or tackifiers as well as fertilizers, micronutrient donors or other formulations for obtaining special effects.

Suitable carriers and adjuvants can be solid or liquid and are substances useful in formulation technology, e.g. natural or regenerated mineral substances, solvents, dispersants, wetting agents, tackifiers, thickeners, binders or fertilizers. Such carriers are for example described in WO 97/33890.

The compounds of formula I or compositions, comprising a compound of formula I as active ingredient and an inert carrier, can be applied to the locus of the plant or plant to be treated, simultaneously or in succession with further compounds. These further compounds can be e.g. fertilizers or micronutrient donors or other preparations which influence the growth of plants. They can also be selective herbicides as well as insecticides, fungicides, bactericides, nematicides, molluscicides or mixtures of several of these preparations, if desired together with further carriers, surfactants or application promoting adjuvants customarily employed in the art of formulation.

A preferred method of applying a compound of formula I, or a composition, comprising a compound of formula I as active ingredient and an inert carrier, is foliar application. The frequency of application and the rate of application will depend on the risk of infestation by the corresponding pathogen. However, the compounds of formula I can also penetrate the plant through the roots via the soil (systemic action) by drenching the locus of the plant with a liquid formulation, or by applying the compounds in solid form to the soil, e.g. in granular form (soil application). In crops of water rice such granulates can be applied to the flooded rice field. The compounds of formula I may also be applied to seeds (coating) by impregnating the seeds or tubers either with a liquid formulation of the fungicide or coating them with a solid formulation.

A formulation, i.e. a composition comprising the compound of formula I and, if desired, a solid or liquid adjuvant, is prepared in a known manner, typically by intimately mixing and/or grinding the compound with extenders, for example solvents, solid carriers and, optionally, surface-active compounds (surfactants).

The agrochemical formulations will usually contain from 0.1 to 99% by weight, preferably from 0.1 to 95% by weight, of the compound of formula I, 99.9 to 1% by weight, preferably 99.8 to 5% by weight, of a solid or liquid adjuvant, and from 0 to 25% by weight, preferably from 0.1 to 25% by weight, of a surfactant.

Whereas it is preferred to formulate commercial products as concentrates, the end user will normally use dilute formulations.

Advantageous rates of application are normally from 5 g to 2 kg of active ingredient (a.i.) per hectare (ha), preferably from 10 g to 1 kg a.i./ha, most preferably from 20 g to 600 g a.i./ha. When used as seed drenching agent, convenient rates of application are from 10 mg to 1 g of active substance per kg of seeds. The rate of application for the desired action can be determined by experiments. It depends for example on the type of action, the developmental stage of the useful plant, and on the application (location, timing, application method) and can, owing to these parameters, vary within wide limits.

Surprisingly, it has now been found that the compounds of formula I can also be used in methods of protecting crops of useful plants against attack by phytopathogenic organisms as well as the treatment of crops of useful plants infested by phytopathogenic organisms comprising administering a combination of glyphosate and at least one compound of formula I to the plant or locus thereof, wherein the plant is resistant or sensitive to glyphosate.

Said methods may provide unexpectedly improved control of diseases compared to using the compounds of formula I in the absence of glyphosate. Said methods may be effective at enhancing the control of disease by compounds of formula I. While the mixture of glyphosate and at least one compound of formula I may increase the disease spectrum controlled, at least in part, by the compound of formula I, an increase in the activity of the compound of formula I on disease species already known to be controlled to some degree by the compound of formula I can also be the effect observed.

Said methods are particularly effective against the phytopathogenic organisms of the kingdom Fungi, phylum Basidiomycot, class Uredinomycetes, subclass Urediniomycetidae and the order Uredinales (commonly referred to as rusts). Species of rusts having a particularly large impact on agriculture include those of the family Phakopsoraceae, particularly those of the genus *Phakopsora*, for example *Phakopsora pachyrhizi*, which is also referred to as Asian soybean rust, and those of the family Pucciniaceae, particularly those of the genus *Puccinia* such as *Puccinia graminis*, also known as stem rust or black rust, which is a problem disease in cereal crops and *Puccinia recondita*, also known as brown rust.

An embodiment of said method is a method of protecting crops of useful plants against attack by a phytopathogenic organism and/or the treatment of crops of useful plants infested by a phytopathogenic organism, said method comprising simultaneously applying glyphosate, including salts or esters thereof, and at least one compound of formula I, which has activity against the phytopathogenic organism to at least one member selected from the group consisting of the plant, a part of the plant and the locus of the plant.

The compounds of formula (I), or a pharmaceutical salt thereof, described above may also have an advantageous spectrum of activity for the treatment and/or prevention of microbial infection in an animal.

"Animal" can be any animal, for example, insect, mammal, reptile, fish, amphibian, preferably mammal, most preferably human. "Treatment" means the use on an animal which has microbial infection in order to reduce or slow or stop the increase or spread of the infection, or to reduce the infection or to cure the infection. "Prevention" means the use on an animal which has no apparent signs of microbial infection in order to prevent any future infection, or to reduce or slow the increase or spread of any future infection.

According to the present invention there is provided the use of a compound of formula (I) in the manufacture of a medicament for use in the treatment and/or prevention of microbial infection in an animal. There is also provided the use of a compound of formula (I) as a pharmaceutical agent. There is also provided the use of a compound of formula (I) as an antimicrobial agent in the treatment of an animal. According to the present invention there is also provided a pharmaceutical composition comprising as an active ingredient a compound of formula (I), or a pharmaceutically acceptable salt thereof, and a pharmaceutically acceptable diluent or carrier. This composition can be used for the treatment and/or prevention of antimicrobial infection in an animal. This pharmaceutical composition can be in a form suitable for oral administration, such as tablet, lozenges, hard capsules, aqueous suspensions, oily suspensions, emulsions dispersible powders, dispersible granules, syrups and elixirs. Alternatively this pharmaceutical composition can be in a form suitable for topical application, such as a spray, a cream or lotion. Alternatively this pharmaceutical composition can be in a form suitable for parenteral administration, for example injection. Alternatively this pharmaceutical composition can be in inhalable form, such as an aerosol spray. The compounds of formula (I) may be effective against various microbial species able to cause a microbial infection in an animal. Examples of such microbial species are those causing Aspergillosis such as *Aspergillus fumigatus, A. flavus, A. terrus, A. nidulans* and *A. niger*, those causing Blastomycosis such as *Blastomyces dermatitidis*; those causing Candidiasis such as *Candida albicans, C. glabrata, C. tropicalis, C. parapsilosis, C. krusei* and *C. lusitaniae*; those causing Coccidioidomycosis such as *Coccidioides immitis*; those causing Cryptococcosis such as *Cryptococcus neoformans*; those causing Histoplasmosis such as *Histoplasma capsulatum* and those causing Zygomycosis such as *Absidia cotymbifera, Rhizomucor pusillus* and *Rhizopus arrhizus*. Further examples are *Fusarium* Spp such as *Fusarium oxysporum* and *Fusarium solani* and *Scedosporium* Spp such as *Scedosporium apiospermum* and *Scedosporium prolificans*. Still further examples are *Microsporum* Spp, *Trichophyton* Spp, *Epidermophyton* Spp, *Mucor* Spp, *Sporothorix* Spp, *Phialophora* Spp, *Cladosporium* Spp, *Petriellidium* spp, *Paracoccidioides* Spp and *Histoplasma* Spp.

The following non-limiting Examples illustrate the above-described invention in greater detail without limiting it.

PREPARATION EXAMPLES

Example P1

Preparation of 3-difluoromethyl-1-methyl-1H-pyrazole-4-carboxylic acid[2-(3,5-dichlorobenzo[b]thiophen-2-yl)-2-methoxy-1-methylethyl]amide (compound 22.2)

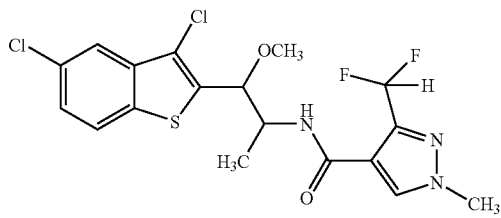

In a sulfonation flask 0.2 g (0.68 mmol) of the amine prepared in example P2c) and 83 mg (0.82 mmol) triethylamine are dissolved in 10 ml of methylenechloride. Then a mixture of 132 mg (0.68 mmol) 3-difluoromethyl-1-methyl-1-H-pyrazole 4-carboxylic acid chloride and 8 ml methylenechloride is added at room temperature under stirring. After stirring for 16 hours the solvent is evaporated in a water jet vacuum and the residue purified by column chromatography over silicagel (eluent: ethylacetate/hexane 1:1). Yield: 240 mg white crystals (80% of theory); m.p. 128-132° C.

Example P2

Preparation of 2-(3,5-dichlorobenz[b]thiophene-2-yl)-2-methoxy-1-methylethylamine a) Preparation of 3,5-dichloro-2-((E)-nitropropenyl)benzo[b]thiophene

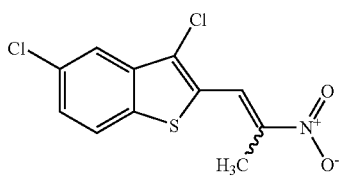

In a sulfonation flask, a mixture containing 6.93 g (0.03 mol) 3,5-dichlorobenzo[b]thio-phene-2-carbaldehyde, 18 g (0.24 mol) nitroethane, 5.8 g (0.075 mol) ammoniumacetate and 60 ml acetic acid is heated at 90° C. for 6 hours. After cooling ethylacetate is added and the organic phase washed three times with water. The organic phase is dried over sodium sulphate and after filration the organic solvent is distilled off in a water jet vacuum. The residue is purified by column chromatography over silicagel (eluent: ethylacetate/heptane 1:5). After chromatography further purification via crystallisation from ethylacetate could be achieved. Yield: 4 g (47% of theory). M.p. 143°-146° C.

b) Preparation of 3,5-dichloro-2-(1-methoxy-2-nitropropyl)benzo[b]thiophene (compound Z6.2)

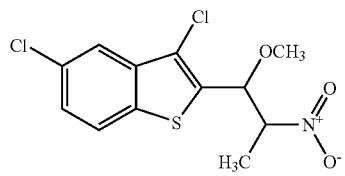

In a sulfonation flask 0.89 g (0.003 mol) 3,5-dichloro-2-((E/Z)-nitropropenyl)benzo[b]thiophene is dissolved in 30 ml of toluene. Then a solution of 2.3 ml of 5.4 m (0.00124 mol) methanolate solution is diluted with 4 ml of methanol and added dropwise to the nitroolefine under stirring at room temperature. The mixture is stirred 3 hours at rt and then 3 ml acetic acid are added and stirring continued for 30 minutes. Then water was added and stirring contued for a few minutes. After addition of ethylacetate the organic phase is separated and the solvent distilled off in a water jet vacuum. The obtained raw material could be used in the next step without further purification. Yield: 1.0 g (ca. 100% of theory) in form of a yellowish oil (diastereoisomeric mixture, ratio: 3:2). $^1$H-NMR: 1.45/d/3H-DS1 (minor isomer), 1.65/d/3H-DS2 (major isomer), 3.30/s/3H-DS1, 3.46/s/3H-DS2, 4.82/m/1H-DS2, 4.87/m/1H-DS1, 5.3/d/1H-DS1, 5.48/d/1H-DS2, 7.4/m/2H-DS1+DS2, 7.7-7.85/m/4H-DS1+DS2.

c) Preparation of 2-(3,5-dichlorobenz[b]thiophene-2-yl)-2-methoxy-1-methylethylamine (compound Z3.2)

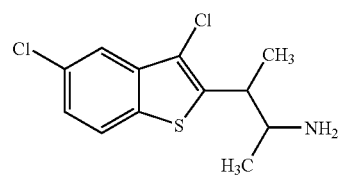

In a sulfonation flask 15 ml (0.015 mol) of an etheral 1 molar LiAlH$_4$ solution is diluted with 40 ml of diethylether. A solution of 0.97 g (0.003 mol) 3,5-dichloro-2-(1-methoxy-2-nitropropyl)benzo[b]thiophene and 30 ml diethylether is added under stirring in such a manner that the internal temperature remains constant at 0-5° C. Then the mixture is warmed up to it and stirring continued for 5 h. Then the reaction mixture is cooled again and water added slowly. After quenching sodium sulphate is added. Filtration and distilling off the solvent in a water jet vacuum, the raw material is obtained. Purification is achieved by column chromatography (eluent: tert. butylmethylether/EtOH 3:1). Yield: 0.62 g (87% of theory) yellowish oil consisting of a diastereoisomeric mixture (ratio:ca. 2:1). $^1$H-NMR: 1.05/d/3H-DS1 (minor isomer), 1.13/d/3H, DS2 (major isomer), 3.2/m/1H-DS1, 3.35/s/6H-DS1+DS2, 3.39/m/1H-DS2, 4.45/d/1H-DS1, 4.52/d/1H-DS2, 7.38/m/2H-DS1+DS2, 7.72/d/2H-DS1+DS2, 7.8/2 s/DS1+DS2.

Tables 1 to 13: Compounds of Formula I-1

The invention is further illustrated by the preferred individual compounds of formula (I-1) listed below in Tables 1 to 13. Characterising data is given in Table 40.

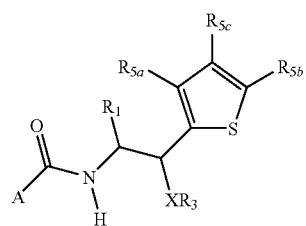

(I-1)

Each of Tables 1 to 13, which follow the Table V below, comprises 48 compounds of the formula (I-1) in which $R_1$, $X$—$R_3$, $R_{5a}$, $R_{5b}$ and $R_{5c}$ have the values given in Table V and A has the value given in the relevant Table 1 to 13. Thus Table 1 corresponds to Table V when V is 1 and A has the value given under the Table 1 heading, Table 2 corresponds to Table V when V is 2 and A has the value given under the Table 2 heading, and so on for Tables 3 to 13.

TABLE V

| Compound Number | $R_1$ | $XR_3$ | $R_{5a}$ | $R_{5b}$ | $R_{5c}$ |
|---|---|---|---|---|---|
| V.1 | H | OMe | Cl | Cl | H |
| V.2 | Me | OMe | Cl | Cl | H |
| V.3 | H | OMe | Cl | Br | H |
| V.4 | Me | OMe | Cl | Br | H |
| V.5 | H | OEt | Cl | Cl | H |
| V.6 | Me | OEt | Cl | Cl | H |
| V.7 | H | OEt | Cl | Br | H |
| V.8 | Me | OEt | Cl | Br | H |
| V.9 | H | SMe | Cl | Cl | H |
| V.10 | Me | SMe | Cl | Cl | H |
| V.11 | H | SMe | Cl | Br | H |
| V.12 | Me | SMe | Cl | Br | H |
| V.13 | H | SEt | Cl | Cl | H |
| V.14 | Me | SEt | Cl | Cl | H |
| V.15 | H | SEt | Cl | Br | H |
| V.16 | Me | SEt | Cl | Br | H |
| V.17 | H | OMe | Cl | ─≡─cyclopropyl | H |
| V.18 | Me | OMe | Cl | ─≡─cyclopropyl | H |
| V.19 | H | OEt | Cl | ─≡─cyclopropyl | H |
| V.20 | Me | OEt | Cl | ─≡─cyclopropyl | H |
| V.21 | H | OMe | Cl | ─≡─cyclopentyl | H |
| V.22 | Me | OMe | Cl | ─≡─cyclopentyl | H |
| V.23 | H | OEt | Cl | ─≡─cyclopentyl | H |
| V.24 | Me | OEt | Cl | ─≡─cyclopentyl | H |
| V.25 | H | OMe | Cl | ─≡─cyclohexyl | H |
| V.26 | Me | OMe | Cl | ─≡─cyclohexyl | H |
| V.27 | H | OEt | Cl | ─≡─cyclohexyl | H |
| V.28 | Me | OEt | Cl | ─≡─cyclohexyl | H |
| V.29 | H | OMe | Cl | ─≡─phenyl | H |
| V.30 | Me | OMe | Cl | ─≡─phenyl | H |
| V.31 | H | OEt | Cl | ─≡─phenyl | H |
| V.32 | Me | OEt | Cl | ─≡─phenyl | H |
| V.33 | H | OMe | Cl | ─(4-Cl-phenyl) | H |
| V.34 | Me | OMe | Cl | ─(4-Cl-phenyl) | H |
| V.35 | H | OEt | Cl | ─(4-Cl-phenyl) | H |
| V.36 | Me | OEt | Cl | ─(4-Cl-phenyl) | H |
| V.37 | H | OMe | Cl | ─(4-F-phenyl) | H |
| V.38 | Me | OMe | Cl | ─(4-F-phenyl) | H |

TABLE V-continued

| Compound Number | $R_1$ | $XR_3$ | $R_{5a}$ | $R_{5b}$ | $R_{5c}$ |
|---|---|---|---|---|---|
| V.39 | H | OEt | Cl | 4-F-C6H4 | H |
| V.40 | Me | OEt | Cl | 4-F-C6H4 | H |
| V.41 | H | OMe | Cl | H | H |
| V.42 | Me | OMe | Cl | H | H |
| V.43 | H | OEt | Cl | H | H |
| V.44 | Me | OEt | Cl | H | H |
| V.45 | H | SMe | Cl | H | H |
| V.46 | Me | SMe | Cl | H | H |
| V.47 | H | SEt | Cl | H | H |
| V.48 | Me | SEt | Cl | H | H |

Table 1 provides 48 compounds of formula (I-1), wherein A is

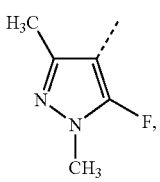

wherein the dashed lines indicate the point of attachment of the group A to the amide group, and $R_1$, X—$R_3$, $R_{5a}$, $R_{5b}$ and $R_{5c}$ are as defined in Table V. For example, compound 1.1 has the following structure:

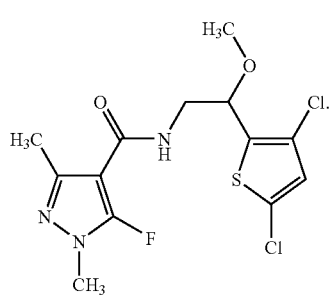
(1.1)

Table 2 provides 48 compounds of formula (I-1) wherein A is

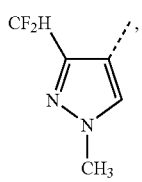

wherein the dashed lines indicate the point of attachment of the group A to the amide group, and $R_1$, X—$R_3$, $R_{5a}$, $R_{5b}$ and $R_{5c}$ are as defined in Table V.

Table 3 provides 48 compounds of formula (I-1) wherein A is

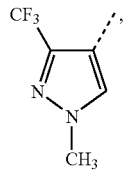

wherein the dashed lines indicate the point of attachment of the group A to the amide group, and $R_1$, X—$R_3$, $R_{5a}$, $R_{5b}$ and $R_{5c}$ are as defined in Table V.

Table 4 provides 48 compounds of formula (I-1) wherein A is

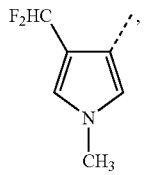

wherein the dashed lines indicate the point of attachment of the group A to the amide group, and $R_1$, X—$R_3$, $R_{5a}$, $R_{5b}$ and $R_{5c}$ are as defined in Table V.

Table 5 provides 48 compounds of formula (I-1) wherein A is

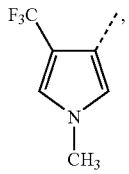

wherein the dashed lines indicate the point of attachment of the group A to the amide group, and $R_1$, X—$R_3$, $R_{5a}$, $R_{5b}$ and $R_{5c}$ are as defined in Table V.

Table 6 provides 48 compounds of formula (I-1) wherein. A is

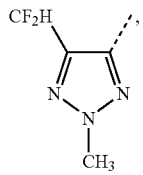

wherein the dashed lines indicate the point of attachment of the group A to the amide group, and $R_1$, X—$R_3$, $R_{5a}$, $R_{5b}$ and $R_{5c}$ are as defined in Table V.

Table 7 provides 48 compounds of formula (I-1) wherein A is

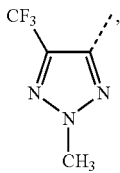

wherein the dashed lines indicate the point of attachment of the group A to the amide group, and $R_1$, X—$R_3$, $R_{5a}$, $R_{5b}$ and $R_{5c}$ are as defined in Table V.

Table 8 provides 48 compounds of formula (I-1) wherein A is

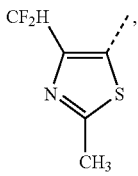

wherein the dashed lines indicate the point of attachment of the group A to the amide group, and $R_1$, X—$R_3$, $R_{5a}$, $R_{5b}$ and $R_{5c}$ are as defined in Table V.

Table 9 provides 48 compounds of formula (I-1) wherein A is

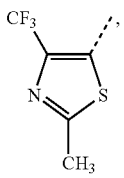

wherein the dashed lines indicate the point of attachment of the group A to the amide group, and $R_1$, X—$R_3$, $R_{5a}$, $R_{5b}$ and $R_{5c}$ are as defined in Table V.

Table 10 provides 48 compounds of formula (I-1) wherein A is

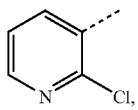

wherein the dashed lines indicate the point of attachment of the group A to the amide group, and $R_1$, X—$R_3$, $R_{5a}$, $R_{5b}$ and $R_{5c}$ are as defined in Table V.

Table 11 provides 48 compounds of formula (I-1) wherein A is

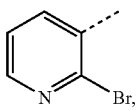

wherein the dashed lines indicate the point of attachment of the group A to the amide group, and $R_1$, X—$R_3$, $R_{5a}$, $R_{5b}$ and $R_{5c}$ are as defined in Table V.

Table 12 provides 48 compounds of formula (I-1) wherein A is

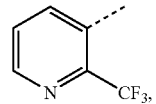

wherein the dashed lines indicate the point of attachment of the group A to the amide group, and $R_1$, X—$R_3$, $R_{5a}$, $R_{5b}$ and $R_{5c}$, are as defined in Table V.

Table 13 provides 48 compounds of formula (I-1) wherein A is

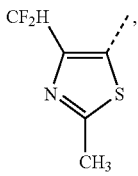

wherein the dashed lines indicate the point of attachment of the group A to the amide group, and $R_1$, X—$R_3$, $R_{5a}$, $R_{5b}$ and $R_{5c}$ are as defined in Table V.

Tables 14 to 20: Compounds of Formula I-2:

The invention is further illustrated by the preferred individual compounds of formula (I-2) listed below in Tables 14 to 20. Characterising data is given in Table 40.

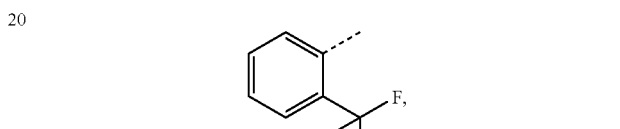

(I-2)

Each of Tables 14 to 20, which follow the Table W below, comprises 158 compounds of the formula (I-2) in which $R_1$, X—$R_3$, $R_{5a}$, $R_{5b}$ and $R_{5c}$ have the values given in Table W and A has the value given in the relevant Table 14 to 20. Thus Table 14 corresponds to Table W when W is 14 and A has the value given under the Table 14 heading, Table 15 corresponds to Table W when W is 15 and A has the value given under the Table 15 heading, and so on for Tables 16 to 20.

TABLE W

| Compound Number | $R_1$ | $XR_3$ | $R_{5a}$ | $R_{5b}$ | $R_{5c}$ |
|---|---|---|---|---|---|
| W.1 | H | OMe | Cl | ≡─◁ | Cl |
| W.2 | Me | OMe | Cl | ≡─◁ | Cl |
| W.3 | H | OEt | Cl | ≡─◁ | Cl |

TABLE W-continued

| Compound Number | R₁ | XR₃ | R₅ₐ | R₅ᵦ | R₅c |
|---|---|---|---|---|---|
| W.4 | Me | OEt | Cl | ≡−△ | Cl |
| W.5 | H | SMe | Cl | ≡−△ | Cl |
| W.6 | Me | SMe | Cl | ≡−△ | Cl |
| W.7 | H | SEt | Cl | ≡−△ | Cl |
| W.8 | Me | SEt | Cl | ≡−△ | Cl |
| W.9 | H | OMe | Cl | Cl | ≡−△ |
| W.10 | Me | OMe | Cl | Cl | ≡−△ |
| W.11 | H | OEt | Cl | Cl | ≡−△ |
| W.12 | Me | OEt | Cl | Cl | ≡−△ |
| W.13 | H | SMe | Cl | Cl | ≡−△ |
| W.14 | Me | SMe | Cl | Cl | ≡−△ |
| W.15 | H | SEt | Cl | Cl | ≡−△ |
| W.16 | Me | SEt | Cl | Cl | ≡−△ |
| W.17 | H | OMe | Cl | ≡−cyclopentyl | Cl |
| W.18 | Me | OMe | Cl | ≡−cyclopentyl | Cl |
| W.19 | H | OEt | Cl | ≡−cyclopentyl | Cl |
| W.20 | Me | OEt | Cl | ≡−cyclopentyl | Cl |
| W.21 | H | SMe | Cl | ≡−cyclopentyl | Cl |
| W.22 | Me | SMe | Cl | ≡−cyclopentyl | Cl |
| W.23 | H | SEt | Cl | ≡−cyclopentyl | Cl |
| W.24 | Me | SEt | Cl | ≡−cyclopentyl | Cl |
| W.25 | H | OMe | Cl | Cl | ≡−cyclopentyl |
| W.26 | Me | OMe | Cl | Cl | ≡−cyclopentyl |
| W.27 | H | OEt | Cl | Cl | ≡−cyclopentyl |
| W.28 | Me | OEt | Cl | Cl | ≡−cyclopentyl |
| W.29 | H | SMe | Cl | Cl | ≡−cyclopentyl |
| W.30 | Me | SMe | Cl | Cl | ≡−cyclopentyl |
| W.31 | H | SEt | Cl | Cl | ≡−cyclopentyl |
| W.32 | Me | SEt | Cl | Cl | ≡−cyclopentyl |
| W.33 | H | OMe | Cl | ≡−cyclohexyl | Cl |
| W.34 | Me | OMe | Cl | ≡−cyclohexyl | Cl |
| W.35 | H | OEt | Cl | ≡−cyclohexyl | Cl |
| W.36 | Me | OEt | Cl | ≡−cyclohexyl | Cl |
| W.37 | H | SMe | Cl | ≡−cyclohexyl | Cl |
| W.38 | Me | SMe | Cl | ≡−cyclohexyl | Cl |
| W.39 | H | SEt | Cl | ≡−cyclohexyl | Cl |
| W.40 | Me | SEt | Cl | ≡−cyclohexyl | Cl |
| W.41 | H | OMe | Cl | Cl | ≡−cyclohexyl |
| W.42 | Me | OMe | Cl | Cl | ≡−cyclohexyl |
| W.43 | H | OEt | Cl | Cl | ≡−cyclohexyl |
| W.44 | Me | OEt | Cl | Cl | ≡−cyclohexyl |

TABLE W-continued

| Compound Number | R₁ | XR₃ | R₅ₐ | R₅ᵦ | R₅ᵧ |
|---|---|---|---|---|---|
| W.45 | H | SMe | Cl | Cl | 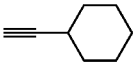 |
| W.46 | Me | SMe | Cl | Cl | 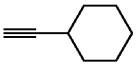 |
| W.47 | H | SEt | Cl | Cl | 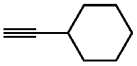 |
| W.48 | Me | SEt | Cl | Cl | 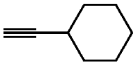 |
| W.49 | H | OMe | Cl | 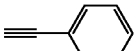 | Cl |
| W.50 | Me | OMe | Cl | 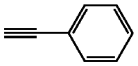 | Cl |
| W.51 | H | OEt | Cl | 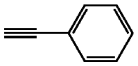 | Cl |
| W.52 | Me | OEt | Cl | 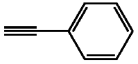 | Cl |
| W.53 | H | SMe | Cl | 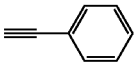 | Cl |
| W.54 | Me | SMe | Cl | 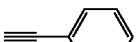 | Cl |
| W.55 | H | SEt | Cl | 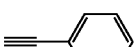 | Cl |
| W.56 | Me | SEt | Cl | 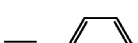 | Cl |
| W.57 | H | OMe | Cl | Cl |  |
| W.58 | Me | OMe | Cl | Cl |  |
| W.59 | H | OEt | Cl | Cl | 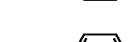 |
| W.60 | Me | OEt | Cl | Cl | 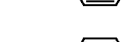 |
| W.61 | H | SMe | Cl | Cl | 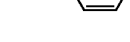 |
| W.62 | Me | SMe | Cl | Cl | 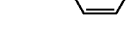 |
| W.63 | H | SEt | Cl | Cl | 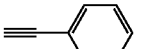 |
| W.64 | Me | SEt | Cl | Cl | 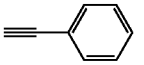 |
| W.65 | H | OMe | Cl | 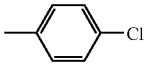 | Cl |
| W.66 | Me | OMe | Cl |  | Cl |
| W.67 | H | OEt | Cl | 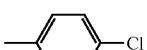 | Cl |
| W.68 | Me | OEt | Cl | 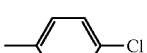 | Cl |
| W.69 | H | SMe | Cl | 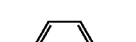 | Cl |
| W.70 | Me | SMe | Cl | 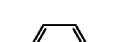 | Cl |
| W.71 | H | SEt | Cl | 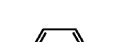 | Cl |
| W.72 | Me | SEt | Cl | 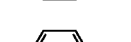 | Cl |
| W.73 | H | OMe | Cl | Cl |  |
| W.74 | Me | OMe | Cl | Cl |  |
| W.75 | H | OEt | Cl | Cl | 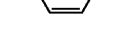 |
| W.76 | Me | OEt | Cl | Cl | 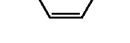 |
| W.77 | H | SMe | Cl | Cl | 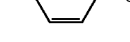 |
| W.78 | Me | SMe | Cl | Cl | 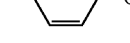 |
| W.79 | H | SEt | Cl | Cl | 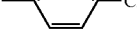 |
| W.80 | Me | SEt | Cl | Cl | 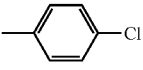 |

TABLE W-continued

| Compound Number | R₁ | XR₃ | R₅ₐ | R₅ᵦ | R₅c |
|---|---|---|---|---|---|
| W.81 | H | OMe | Cl | 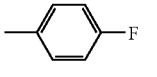 | Cl |
| W.82 | Me | OMe | Cl | 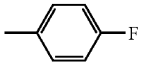 | Cl |
| W.83 | H | OEt | Cl | 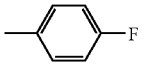 | Cl |
| W.84 | Me | OEt | Cl | 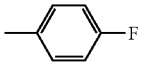 | Cl |
| W.85 | H | SMe | Cl | 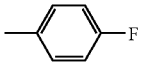 | Cl |
| W.86 | Me | SMe | Cl | 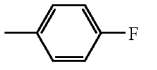 | Cl |
| W.87 | H | SEt | Cl | 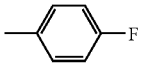 | Cl |
| W.88 | Me | SEt | Cl | 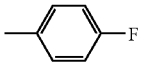 | Cl |
| W.89 | H | OMe | Cl | Cl |  |
| W.90 | Me | OMe | Cl | Cl |  |
| W.91 | H | OEt | Cl | Cl | 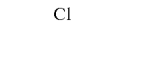 |
| W.92 | Me | OEt | Cl | Cl |  |
| W.93 | H | SMe | Cl | Cl | 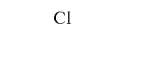 |
| W.94 | Me | SMe | Cl | Cl | 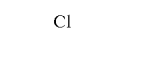 |
| W.95 | H | SEt | Cl | Cl | 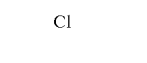 |
| W.96 | Me | SEt | Cl | Cl |  |
| W.97 | H | OMe | Cl | Cl | Cl |
| W.98 | Me | OMe | Cl | Cl | Cl |
| W.99 | H | OEt | Cl | Cl | Cl |
| W.100 | Me | OEt | Cl | Cl | Cl |
| W.101 | H | SMe | Cl | Cl | Cl |
| W.102 | Me | SMe | Cl | Cl | Cl |
| W.103 | H | SEt | Cl | Cl | Cl |
| W.104 | Me | SEt | Cl | Cl | Cl |
| W.105 | H | OMe | Cl | H | Cl |
| W.106 | Me | OMe | Cl | H | Cl |
| W.107 | H | OEt | Cl | H | Cl |
| W.108 | Me | OEt | Cl | H | Cl |
| W.109 | H | SMe | Cl | H | Cl |
| W.110 | Me | SMe | Cl | H | Cl |
| W.111 | H | SEt | Cl | H | Cl |
| W.112 | Me | SEt | Cl | H | Cl |
| W.113 | H | OMe | Cl | Cl | H |
| W.114 | Me | OMe | Cl | Cl | H |
| W.115 | H | OEt | Cl | Cl | H |
| W.116 | Me | OEt | Cl | Cl | H |
| W.117 | H | SMe | Cl | Cl | H |
| W.118 | Me | SMe | Cl | Cl | H |
| W.119 | H | SEt | Cl | Cl | H |
| W.120 | Me | SEt | Cl | Cl | H |
| W.121 | H | OMe | Cl | Br | Cl |
| W.122 | Me | OMe | Cl | Br | Cl |
| W.123 | H | OEt | Cl | Br | Cl |
| W.124 | Me | OEt | Cl | Br | Cl |
| W.125 | H | SMe | Cl | Br | Cl |
| W.126 | Me | SMe | Cl | Br | Cl |
| W.127 | H | SEt | Cl | Br | Cl |
| W.128 | Me | SEt | Cl | Br | Cl |
| W.129 | H | OMe | Cl | Cl | Br |
| W.130 | Me | OMe | Cl | Cl | Br |
| W.131 | H | OEt | Cl | Cl | Br |
| W.132 | Me | OEt | Cl | Cl | Br |
| W.133 | H | SMe | Cl | Cl | Br |
| W.134 | Me | SMe | Cl | Cl | Br |
| W.135 | H | SEt | Cl | Cl | Br |
| W.136 | Me | SEt | Cl | Cl | Br |
| W.137 | H | OMe | Cl | Cl | 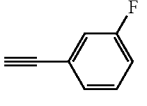 |
| W.138 | Me | OMe | Cl | Cl | 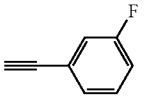 |
| W.139 | H | OMe | Cl | Cl | 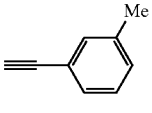 |
| W.140 | Me | OMe | Cl | Cl | 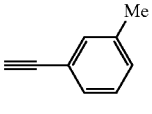 |
| W.141 | H | OMe | Cl | Cl | 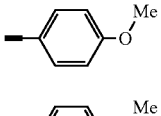 |
| W.142 | Me | OMe | Cl | Cl | 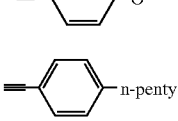 |
| W.143 | H | OMe | Cl | Cl | 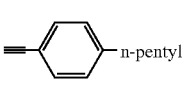 |
| W.144 | Me | OMe | Cl | Cl |  |

TABLE W-continued

| Compound Number | R$_1$ | XR$_3$ | R$_{5a}$ | R$_{5b}$ | R$_{5c}$ |
|---|---|---|---|---|---|
| W.145 | H | OMe | Cl | Cl | ethynyl-2,4,5-trimethylphenyl |
| W.146 | Me | OMe | Cl | Cl | ethynyl-2,4,5-trimethylphenyl |
| W.147 | H | OMe | Cl | Cl | 2-(trifluoromethyl)phenylethynyl |
| W.148 | Me | OMe | Cl | Cl | 2-(trifluoromethyl)phenylethynyl |
| W.149 | H | OMe | Cl | Cl | pyridin-3-ylethynyl |
| W.150 | Me | OMe | Cl | Cl | pyridin-3-ylethynyl |
| W.151 | H | OMe | Cl | Cl | (6-methylpyridin-3-yl)ethynyl |
| W.152 | Me | OMe | Cl | Cl | (6-methylpyridin-3-yl)ethynyl |
| W.153 | H | OMe | Cl | Cl | thiophen-3-ylethynyl |
| W.154 | Me | OMe | Cl | Cl | thiophen-3-ylethynyl |
| W.155 | H | OMe | Cl | Cl | (1-methyl-1H-imidazol-5-yl)ethynyl |
| W.156 | Me | OMe | Cl | Cl | (1-methyl-1H-imidazol-5-yl)ethynyl |
| W.157 | H | OMe | Cl | Cl | 3-(trifluoromethyl)phenyl |
| W.158 | Me | OMe | Cl | Cl | 3-(trifluoromethyl)phenyl |

Table 14 provides 158 compounds of formula (I-2), wherein A is

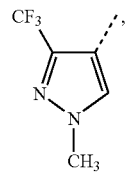

wherein the dashed lines indicate the point of attachment of the group A to the amide group, and R$_1$, X—R$_3$, R$_{5a}$, R$_{5b}$ and R$_{5c}$ are as defined in Table W.

Table 15 provides 158 compounds of formula (I-2) wherein A is

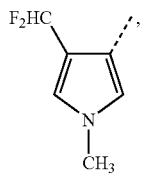

wherein the dashed lines indicate the point of attachment of the group A to the amide group, and R$_1$, X—R$_3$, R$_{5a}$, R$_{5b}$ and R$_{5c}$ are as defined in Table W.

Table 16 provides 158 compounds of formula (I-2) wherein A is

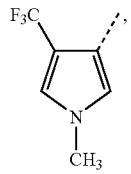

wherein the dashed lines indicate the point of attachment of the group A to the amide group, and R$_1$, X—R$_3$, R$_{5a}$, R$_{5b}$ and R$_{5c}$ are as defined in Table W.

Table 17 provides 158 compounds of formula (I-2) wherein A is

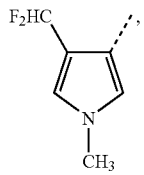

wherein the dashed lines indicate the point of attachment of the group A to the amide group, and R$_1$, X—R$_3$, R$_{5a}$, R$_{5b}$ and R$_{5c}$ are as defined in Table W.

Table 18 provides 158 compounds of formula (I-2) wherein A is

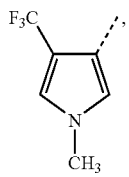

wherein the dashed lines indicate the point of attachment of the group A to the amide group, and $R_1$, $X$—$R_3$, $R_{5a}$, $R_{5b}$ and $R_{5c}$ are as defined in Table W.

Table 19 provides 158 compounds of formula (I-2) wherein A is

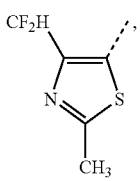

wherein the dashed lines indicate the point of attachment of the group A to the amide group, and $R_1$, $X$—$R_3$, $R_{5a}$, $R_{5b}$ and $R_{5c}$ are as defined in Table W.

Table 20 provides 158 compounds of formula (I-2) wherein A is

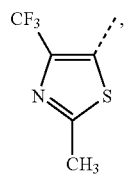

wherein the dashed lines indicate the point of attachment of the group A to the amide group, and $R_1$, $X$—$R_3$, $R_{5a}$, $R_{5b}$ and $R_{5c}$ are as defined in Table W.

Tables 21 to 33: Compounds of Formula I-3:

The invention is further illustrated by the preferred individual compounds of formula (I-3) listed below in Tables 21 to 33. Characterising data is given in Table 40.

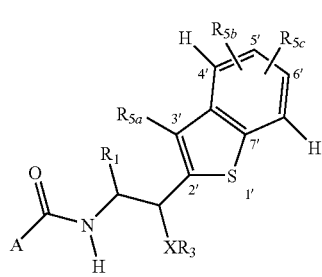

(I-3)

Each of Tables 21 to 33, which follow the Table Y below, comprises 64 compounds of the formula (I-3) in which $R_1$, $X$—$R_3$, $R_{5a}$, $R_{5b}$ and $R_{5c}$ have the values given in Table Y and A has the value given in the relevant Table 21 to 33. Thus Table 21 corresponds to Table Y when Y is 21 and A has the value given under the Table 21 heading, Table 22 corresponds to Table Y when Y is 22 and A has the value given under the Table 22 heading, and so on for Tables 23 to 33.

TABLE Y

| Compound Number | $R_1$ | $XR_3$ | $R_{5a}$ | $R_{5b}$ | $R_{5c}$ |
|---|---|---|---|---|---|
| Y.1 | H | OMe | Cl | 5'-Cl | H |
| Y.2 | Me | OMe | Cl | 5'-Cl | H |
| Y.3 | H | OEt | Cl | 5'-Cl | H |
| Y.4 | Me | OEt | Cl | 5'-Cl | H |
| Y.5 | H | SMe | Cl | 5'-Cl | H |
| Y.6 | Me | SMe | Cl | 5'-Cl | H |
| Y.7 | H | SEt | Cl | 5'-Cl | H |
| Y.8 | Me | SEt | Cl | 5'-Cl | H |
| Y.9 | H | OMe | Cl | 5'-Br | H |
| Y.10 | Me | OMe | Cl | 5'-Br | H |
| Y.11 | H | OEt | Cl | 5'-Br | H |
| Y.12 | Me | OEt | Cl | 5'-Br | H |
| Y.13 | H | SMe | Cl | 5'-Br | H |
| Y.14 | Me | SMe | Cl | 5'-Br | H |
| Y.15 | H | SEt | Cl | 5'-Br | H |
| Y.16 | Me | SEt | Cl | 5'-Br | H |
| Y.17 | H | OMe | Cl | 5'-≡-▷ | H |
| Y.18 | Me | OMe | Cl | 5'-≡-▷ | H |
| Y.19 | H | OEt | Cl | 5'-≡-▷ | H |
| Y.20 | Me | OEt | Cl | 5'-≡-▷ | H |
| Y.21 | H | SMe | Cl | 5'-≡-▷ | H |
| Y.22 | Me | SMe | Cl | 5'-≡-▷ | H |
| Y.23 | H | SEt | Cl | 5'-≡-▷ | H |
| Y.24 | Me | SEt | Cl | 5'-≡-▷ | H |
| Y.25 | H | OMe | Cl | 5'-⌬-Cl | H |
| Y.26 | Me | OMe | Cl | 5'-⌬-Cl | H |
| Y.27 | H | OEt | Cl | 5'-⌬-Cl | H |
| Y.28 | Me | OEt | Cl | 5'-⌬-Cl | H |
| Y.29 | H | SMe | Cl | 5'-⌬-Cl | H |

TABLE Y-continued

| Compound Number | R₁ | XR₃ | R₅ₐ | R₅ᵦ | R₅c |
|---|---|---|---|---|---|
| Y.30 | Me | SMe | Cl | 5'-(4-chlorophenyl) | H |
| Y.31 | H | SEt | Cl | 5'-(4-chlorophenyl) | H |
| Y.32 | Me | SEt | Cl | 5'-(4-chlorophenyl) | H |
| Y.33 | H | OMe | Cl | 6'-Cl | H |
| Y.34 | Me | OMe | Cl | 6'-Cl | H |
| Y.35 | H | OEt | Cl | 6'-Cl | H |
| Y.36 | Me | OEt | Cl | 6'-Cl | H |
| Y.37 | H | SMe | Cl | 6'-Cl | H |
| Y.38 | Me | SMe | Cl | 6'-Cl | H |
| Y.39 | H | SEt | Cl | 6'-Cl | H |
| Y.40 | Me | SEt | Cl | 6'-Cl | H |
| Y.41 | H | OMe | Cl | 6'-Br | H |
| Y.42 | Me | OMe | Cl | 6'-Br | H |
| Y.43 | H | OEt | Cl | 6'-Br | H |
| Y.44 | Me | OEt | Cl | 6'-Br | H |
| Y.45 | H | SMe | Cl | 6'-Br | H |
| Y.46 | Me | SMe | Cl | 6'-Br | H |
| Y.47 | H | SEt | Cl | 6'-Br | H |
| Y.48 | Me | SEt | Cl | 6'-Br | H |
| Y.49 | H | OMe | Cl | 6'-(cyclopropylethynyl) | H |
| Y.50 | Me | OMe | Cl | 6'-(cyclopropylethynyl) | H |
| Y.51 | H | OEt | Cl | 6'-(cyclopropylethynyl) | H |
| Y.52 | Me | OEt | Cl | 6'-(cyclopropylethynyl) | H |
| Y.53 | H | SMe | Cl | 6'-(cyclopropylethynyl) | H |
| Y.54 | Me | SMe | Cl | 6'-(cyclopropylethynyl) | H |
| Y.55 | H | SEt | Cl | 6'-(cyclopropylethynyl) | H |
| Y.56 | Me | SEt | Cl | 6'-(cyclopropylethynyl) | H |
| Y.57 | H | OMe | Cl | 6'-(4-chlorophenyl) | H |
| Y.58 | Me | OMe | Cl | 6'-(4-chlorophenyl) | H |
| Y.59 | H | OEt | Cl | 6'-(4-chlorophenyl) | H |
| Y.60 | Me | OEt | Cl | 6'-(4-chlorophenyl) | H |
| Y.61 | H | SMe | Cl | 6'-(4-chlorophenyl) | H |
| Y.62 | Me | SMe | Cl | 6'-(4-chlorophenyl) | H |
| Y.63 | H | SEt | Cl | 6'-(4-chlorophenyl) | H |
| Y.64 | Me | SEt | Cl | 6'-(4-chlorophenyl) | H |

Table 21 provides 64 compounds of formula (I-3), wherein A is

[3-methyl-5-fluoro-1-methyl-1H-pyrazol-4-yl structure with H₃C at 3-position, F at 5-position, CH₃ on N1, attachment at 4-position]

wherein the dashed lines indicate the point of attachment of the group A to the amide group, and R₁, X—R₃, R₅ₐ, R₅ᵦ and R₅c are as defined in Table Y.

Table 22 provides 64 compounds of formula (I-3) wherein A is

[3-difluoromethyl-1-methyl-1H-pyrazol-4-yl structure with CF₂H at 3-position, CH₃ on N1, attachment at 4-position]

wherein the dashed lines indicate the point of attachment of the group A to the amide group, and R₁, X—R₃, R₅ₐ, R₅ᵦ and R₅c are as defined in Table Y.

Table 23 provides 64 compounds of formula (I-3) wherein A is

[3-trifluoromethyl-1-methyl-1H-pyrazol-4-yl structure with CF₃ at 3-position, CH₃ on N1, attachment at 4-position]

wherein the dashed lines indicate the point of attachment of the group A to the amide group, and $R_1$, $X—R_3$, $R_{5a}$, $R_{5b}$ and $R_{5c}$ are as defined in Table Y.

Table 24 provides 64 compounds of formula (I-3) wherein A is

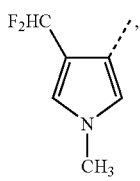

wherein the dashed lines indicate the point of attachment of the group A to the amide group, and $R_1$, $X—R_3$, $R_{5a}$, $R_{5b}$ and $R_{5c}$ are as defined in Table Y.

Table 25 provides 64 compounds of formula (I-3) wherein A is

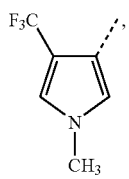

wherein the dashed lines indicate the point of attachment of the group A to the amide group, and $R_1$, $X—R_3$, $R_{5a}$, $R_{5b}$ and $R_{5c}$ are as defined in Table.

Table 26 provides 64 compounds of formula (I-3) wherein A is

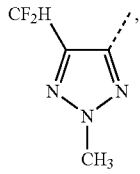

wherein the dashed lines indicate the point of attachment of the group A to the amide group, and $R_1$, $X—R_3$, $R_{5a}$, $R_{5b}$ and $R_{5c}$ are as defined in Table Y.

Table 27 provides 64 compounds of formula (I-3) wherein A is

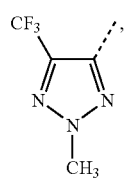

wherein the dashed lines indicate the point of attachment of the group A to the amide group, and $R_1$, $X—R_3$, $R_{5a}$, $R_{5b}$ and $R_{5c}$ are as defined in Table Y.

Table 28 provides 64 compounds of formula (I-3) wherein A is

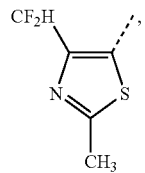

wherein the dashed lines indicate the point of attachment of the group A to the amide group, and $R_1$, $X—R_3$, $R_{5a}$, $R_{5b}$ and $R_{5c}$ are as defined in Table Y.

Table 29 provides 64 compounds of formula (I-3) wherein A is

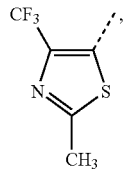

wherein the dashed lines indicate the point of attachment of the group A to the amide group, and $R_1$, $X—R_3$, $R_{5a}$, $R_{5b}$ and $R_{5c}$ are as defined in Table Y.

Table 30 provides 64 compounds of formula (I-3) wherein A is

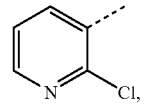

wherein the dashed lines indicate the point of attachment of the group A to the amide group, and $R_1$, $X—R_3$, $R_{5a}$, $R_{5b}$ and $R_{5c}$ are as defined in Table Y.

Table 31 provides 64 compounds of formula (I-3) wherein A is

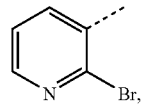

wherein the dashed lines indicate the point of attachment of the group A to the amide group, and $R_1$, $X—R_3$, $R_{5a}$, $R_{5b}$ and $R_{5c}$ are as defined in Table.

Table 32 provides 64 compounds of formula (I-3) wherein A is

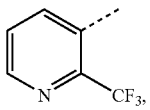

wherein the dashed lines indicate the point of attachment of the group A to the amide group, and $R_1$, $X—R_3$, $R_{5a}$, $R_{5b}$ and $R_{5c}$ are as defined in Table Y.

Table 33 provides 64 compounds of formula (I-3) wherein A is

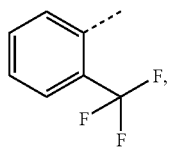

wherein the dashed lines indicate the point of attachment of the group A to the amide group, and $R_1$, $X-R_3$, $R_{5a}$, $R_{5b}$ and $R_{5c}$ are as defined in Table Y.

TABLE 34

Compounds of formula II-1
The invention is further illustrated by the preferred individual compounds of formula (II-1) listed below in Table 34. Characterising data is given in Table 40.

(II-1)

| Compound Number | $R_1$ | $XR_3$ | $R_{5a}$ | $R_{5b}$ | $R_{5c}$ |
|---|---|---|---|---|---|
| Z1.1 | H | OMe | Cl | Cl | H |
| Z1.2 | Me | OMe | Cl | Cl | H |
| Z1.3 | H | OMe | Cl | Br | H |
| Z1.4 | Me | OMe | Cl | Br | H |
| Z1.5 | H | OEt | Cl | Cl | H |
| Z1.6 | Me | OEt | Cl | Cl | H |
| Z1.7 | H | OEt | Cl | Br | H |
| Z1.8 | Me | OEt | Cl | Br | H |
| Z1.9 | H | SMe | Cl | Cl | H |
| Z1.10 | Me | SMe | Cl | Cl | H |
| Z1.11 | H | SMe | Cl | Br | H |
| Z1.12 | Me | SMe | Cl | Br | H |
| Z1.13 | H | SEt | Cl | Cl | H |
| Z1.14 | Me | SEt | Cl | Cl | H |
| Z1.15 | H | SEt | Cl | Br | H |
| Z1.16 | Me | SEt | Cl | Br | H |
| Z1.17 | H | OMe | Cl | ethynyl-cyclopropyl | H |
| Z1.18 | Me | OMe | Cl | ethynyl-cyclopropyl | H |
| Z1.19 | H | OEt | Cl | ethynyl-cyclopropyl | H |
| Z1.20 | Me | OEt | Cl | ethynyl-cyclopropyl | H |
| Z1.21 | H | OMe | Cl | ethynyl-cyclopentyl | H |
| Z1.22 | Me | OMe | Cl | ethynyl-cyclopentyl | H |
| Z1.23 | H | OEt | Cl | ethynyl-cyclopentyl | H |
| Z1.24 | Me | OEt | Cl | ethynyl-cyclopentyl | H |
| Z1.25 | H | OMe | Cl | ethynyl-cyclohexyl | H |
| Z1.26 | Me | OMe | Cl | ethynyl-cyclohexyl | H |
| Z1.27 | H | OEt | Cl | ethynyl-cyclohexyl | H |
| Z1.28 | Me | OEt | Cl | ethynyl-cyclohexyl | H |
| Z1.29 | H | OMe | Cl | ethynyl-phenyl | H |
| Z1.30 | Me | OMe | Cl | ethynyl-phenyl | H |
| Z1.31 | H | OEt | Cl | ethynyl-phenyl | H |
| Z1.32 | Me | OEt | Cl | ethynyl-phenyl | H |
| Z1.33 | H | OMe | Cl | 4-chlorophenyl | H |

TABLE 34-continued

Compounds of formula II-1
The invention is further illustrated by the preferred individual compounds of formula (II-1) listed below in Table 34. Characterising data is given in Table 40.

(II-1): thiophene ring with R$_{5a}$, R$_{5c}$, R$_{5b}$ substituents; side chain –CH(R$_1$)(NH$_2$)–CH(XR$_3$)–

| Compound Number | R$_1$ | XR$_3$ | R$_{5a}$ | R$_{5b}$ | R$_{5c}$ |
|---|---|---|---|---|---|
| Z1.34 | Me | OMe | Cl | 4-Cl-phenyl | H |
| Z1.35 | H | OEt | Cl | 4-Cl-phenyl | H |
| Z1.36 | Me | OEt | Cl | 4-Cl-phenyl | H |
| Z1.37 | H | OMe | Cl | 4-F-phenyl | H |
| Z1.38 | Me | OMe | Cl | 4-F-phenyl | H |
| Z1.39 | H | OEt | Cl | 4-F-phenyl | H |
| Z1.40 | Me | OEt | Cl | 4-F-phenyl | H |
| Z1.41 | H | OMe | Cl | H | H |
| Z1.42 | Me | OMe | Cl | H | H |
| Z1.43 | H | OEt | Cl | H | H |
| Z1.44 | Me | OEt | Cl | H | H |
| Z1.45 | H | SMe | Cl | H | H |
| Z1.46 | Me | SMe | Cl | H | H |
| Z1.47 | H | SEt | Cl | H | H |
| Z1.48 | Me | SEt | Cl | H | H |

TABLE 35

Compounds of formula II-2
The invention is further illustrated by the preferred individual compounds of formula (II-2) listed below in Table 35. Characterising data is given in Table 40.

(II-2): thiophene ring with R$_{5c}$, R$_{5b}$, R$_{5a}$ substituents; side chain –CH(R$_1$)(NH$_2$)–CH(XR$_3$)–

| Compound Number | R$_1$ | XR$_3$ | R$_{5a}$ | R$_{5b}$ | R$_{5c}$ |
|---|---|---|---|---|---|
| Z2.1 | H | OMe | Cl | ethynyl-cyclopropyl | Cl |
| Z2.2 | Me | OMe | Cl | ethynyl-cyclopropyl | Cl |
| Z2.3 | H | OEt | Cl | ethynyl-cyclopropyl | Cl |
| Z2.4 | Me | OEt | Cl | ethynyl-cyclopropyl | Cl |
| Z2.5 | H | SMe | Cl | ethynyl-cyclopropyl | Cl |
| Z2.6 | Me | SMe | Cl | ethynyl-cyclopropyl | Cl |
| Z2.7 | H | SEt | Cl | ethynyl-cyclopropyl | Cl |
| Z2.8 | Me | SEt | Cl | ethynyl-cyclopropyl | Cl |
| Z2.9 | H | OMe | Cl | Cl | ethynyl-cyclopropyl |
| Z2.10 | Me | OMe | Cl | Cl | ethynyl-cyclopropyl |
| Z2.11 | H | OEt | Cl | Cl | ethynyl-cyclopropyl |
| Z2.12 | Me | OEt | Cl | Cl | ethynyl-cyclopropyl |
| Z2.13 | H | SMe | Cl | Cl | ethynyl-cyclopropyl |
| Z2.14 | Me | SMe | Cl | Cl | ethynyl-cyclopropyl |
| Z2.15 | H | SEt | Cl | Cl | ethynyl-cyclopropyl |
| Z2.16 | Me | SEt | Cl | Cl | ethynyl-cyclopropyl |
| Z2.17 | H | OMe | Cl | ethynyl-cyclopentyl | Cl |
| Z2.18 | Me | OMe | Cl | ethynyl-cyclopentyl | Cl |

TABLE 35-continued

Compounds of formula II-2
The invention is further illustrated by the preferred individual
compounds of formula (II-2) listed below in Table 35.
Characterising data is given in Table 40.

(II-2)

| Compound Number | $R_1$ | $XR_3$ | $R_{5a}$ | $R_{5b}$ | $R_{5c}$ |
|---|---|---|---|---|---|
| Z2.19 | H | OEt | Cl | ethynylcyclopentyl | Cl |
| Z2.20 | Me | OEt | Cl | ethynylcyclopentyl | Cl |
| Z2.21 | H | SMe | Cl | ethynylcyclopentyl | Cl |
| Z2.22 | Me | SMe | Cl | ethynylcyclopentyl | Cl |
| Z2.23 | H | SEt | Cl | ethynylcyclopentyl | Cl |
| Z2.24 | Me | SEt | Cl | ethynylcyclopentyl | Cl |
| Z2.25 | H | OMe | Cl | Cl | ethynylcyclopentyl |
| Z2.26 | Me | OMe | Cl | Cl | ethynylcyclopentyl |
| Z2.27 | H | OEt | Cl | Cl | ethynylcyclopentyl |
| Z2.28 | Me | OEt | Cl | Cl | ethynylcyclopentyl |
| Z2.29 | H | SMe | Cl | Cl | ethynylcyclopentyl |
| Z2.30 | Me | SMe | Cl | Cl | ethynylcyclopentyl |
| Z2.31 | H | SEt | Cl | Cl | ethynylcyclopentyl |
| Z2.32 | Me | SEt | Cl | Cl | ethynylcyclopentyl |
| Z2.33 | H | OMe | Cl | ethynylcyclohexyl | Cl |
| Z2.34 | Me | OMe | Cl | ethynylcyclohexyl | Cl |
| Z2.35 | H | OEt | Cl | ethynylcyclohexyl | Cl |
| Z2.36 | Me | OEt | Cl | ethynylcyclohexyl | Cl |
| Z2.37 | H | SMe | Cl | ethynylcyclohexyl | Cl |
| Z2.38 | Me | SMe | Cl | ethynylcyclohexyl | Cl |
| Z2.39 | H | SEt | Cl | ethynylcyclohexyl | Cl |
| Z2.40 | Me | SEt | Cl | ethynylcyclohexyl | Cl |
| Z2.41 | H | OMe | Cl | Cl | ethynylcyclohexyl |
| Z2.42 | Me | OMe | Cl | Cl | ethynylcyclohexyl |
| Z2.43 | H | OEt | Cl | Cl | ethynylcyclohexyl |
| Z2.44 | Me | OEt | Cl | Cl | ethynylcyclohexyl |
| Z2.45 | H | SMe | Cl | Cl | ethynylcyclohexyl |

TABLE 35-continued

Compounds of formula II-2
The invention is further illustrated by the preferred individual compounds of formula (II-2) listed below in Table 35. Characterising data is given in Table 40.

(II-2)

$$\text{structure with } R_1, H_2N, XR_3, R_{5a}, R_{5b}, R_{5c}, S$$

| Compound Number | R$_1$ | XR$_3$ | R$_{5a}$ | R$_{5b}$ | R$_{5c}$ |
|---|---|---|---|---|---|
| Z2.46 | Me | SMe | Cl | Cl | cyclohexyl-C≡C- |
| Z2.47 | H | SEt | Cl | Cl | cyclohexyl-C≡C- |
| Z2.48 | Me | SEt | Cl | Cl | cyclohexyl-C≡C- |
| Z2.49 | H | OMe | Cl | phenyl-C≡C- | Cl |
| Z2.50 | Me | OMe | Cl | phenyl-C≡C- | Cl |
| Z2.51 | H | OEt | Cl | phenyl-C≡C- | Cl |
| Z2.52 | Me | OEt | Cl | phenyl-C≡C- | Cl |
| Z2.53 | H | SMe | Cl | phenyl-C≡C- | Cl |
| Z2.54 | Me | SMe | Cl | phenyl-C≡C- | Cl |
| Z2.55 | H | SEt | Cl | phenyl-C≡C- | Cl |
| Z2.56 | Me | SEt | Cl | phenyl-C≡C- | Cl |
| Z2.57 | H | OMe | Cl | Cl | phenyl-C≡C- |
| Z2.58 | Me | OMe | Cl | Cl | phenyl-C≡C- |
| Z2.59 | H | OEt | Cl | Cl | phenyl-C≡C- |
| Z2.60 | Me | OEt | Cl | Cl | phenyl-C≡C- |
| Z2.61 | H | SMe | Cl | Cl | phenyl-C≡C- |
| Z2.62 | Me | SMe | Cl | Cl | phenyl-C≡C- |
| Z2.63 | H | SEt | Cl | Cl | phenyl-C≡C- |
| Z2.64 | Me | SEt | Cl | Cl | phenyl-C≡C- |
| Z2.65 | H | OMe | Cl | 4-Cl-phenyl | Cl |
| Z2.66 | Me | OMe | Cl | 4-Cl-phenyl | Cl |
| Z2.67 | H | OEt | Cl | 4-Cl-phenyl | Cl |
| Z2.68 | Me | OEt | Cl | 4-Cl-phenyl | Cl |
| Z2.69 | H | SMe | Cl | 4-Cl-phenyl | Cl |
| Z2.70 | Me | SMe | Cl | 4-Cl-phenyl | Cl |
| Z2.71 | H | SEt | Cl | 4-Cl-phenyl | Cl |

TABLE 35-continued

Compounds of formula II-2
The invention is further illustrated by the preferred individual compounds of formula (II-2) listed below in Table 35. Characterising data is given in Table 40.

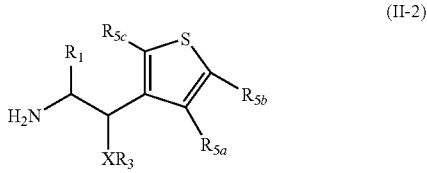

(II-2)

| Compound Number | R₁ | XR₃ | R₅ₐ | R₅ᵦ | R₅c |
|---|---|---|---|---|---|
| Z2.72 | Me | SEt | Cl | 4-Cl-phenyl | Cl |
| Z2.73 | H | OMe | Cl | Cl | 4-Cl-phenyl |
| Z2.74 | Me | OMe | Cl | Cl | 4-Cl-phenyl |
| Z2.75 | H | OEt | Cl | Cl | 4-Cl-phenyl |
| Z2.76 | Me | OEt | Cl | Cl | 4-Cl-phenyl |
| Z2.77 | H | SMe | Cl | Cl | 4-Cl-phenyl |
| Z2.78 | Me | SMe | Cl | Cl | 4-Cl-phenyl |
| Z2.79 | H | SEt | Cl | Cl | 4-Cl-phenyl |
| Z2.80 | Me | SEt | Cl | Cl | 4-Cl-phenyl |
| Z2.81 | H | OMe | Cl | 4-F-phenyl | Cl |
| Z2.82 | Me | OMe | Cl | 4-F-phenyl | Cl |
| Z2.83 | H | OEt | Cl | 4-F-phenyl | Cl |
| Z2.84 | Me | OEt | Cl | 4-F-phenyl | Cl |
| Z2.85 | H | SMe | Cl | 4-F-phenyl | Cl |
| Z2.86 | Me | SMe | Cl | 4-F-phenyl | Cl |
| Z2.87 | H | SEt | Cl | 4-F-phenyl | Cl |
| Z2.88 | Me | SEt | Cl | 4-F-phenyl | Cl |
| Z2.89 | H | OMe | Cl | Cl | 4-F-phenyl |
| Z2.90 | Me | OMe | Cl | Cl | 4-F-phenyl |
| Z2.91 | H | OEt | Cl | Cl | 4-F-phenyl |
| Z2.92 | Me | OEt | Cl | Cl | 4-F-phenyl |
| Z2.93 | H | SMe | Cl | Cl | 4-F-phenyl |
| Z2.94 | Me | SMe | Cl | Cl | 4-F-phenyl |
| Z2.95 | H | SEt | Cl | Cl | 4-F-phenyl |
| Z2.96 | Me | SEt | Cl | Cl | 4-F-phenyl |
| Z2.97 | H | OMe | Cl | Cl | Cl |
| Z2.98 | Me | OMe | Cl | Cl | Cl |
| Z2.99 | H | OEt | Cl | Cl | Cl |
| Z2.100 | Me | OEt | Cl | Cl | Cl |
| Z2.101 | H | SMe | Cl | Cl | Cl |
| Z2.102 | Me | SMe | Cl | Cl | Cl |
| Z2.103 | H | SEt | Cl | Cl | Cl |
| Z2.104 | Me | SEt | Cl | Cl | Cl |
| Z2.105 | H | OMe | Cl | H | Cl |
| Z2.106 | Me | OMe | Cl | H | Cl |
| Z2.107 | H | OEt | Cl | H | Cl |
| Z2.108 | Me | OEt | Cl | H | Cl |

TABLE 35-continued

Compounds of formula II-2
The invention is further illustrated by the preferred individual compounds of formula (II-2) listed below in Table 35.
Characterising data is given in Table 40.

(II-2)
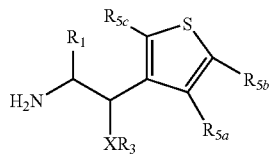

| Compound Number | $R_1$ | $XR_3$ | $R_{5a}$ | $R_{5b}$ | $R_{5c}$ |
|---|---|---|---|---|---|
| Z2.109 | H | SMe | Cl | H | Cl |
| Z2.110 | Me | SMe | Cl | H | Cl |
| Z2.111 | H | SEt | Cl | H | Cl |
| Z2.112 | Me | SEt | Cl | H | Cl |
| Z2.113 | H | OMe | Cl | Cl | H |
| Z2.114 | Me | OMe | Cl | Cl | H |
| Z2.115 | H | OEt | Cl | Cl | H |
| Z2.116 | Me | OEt | Cl | Cl | H |
| Z2.117 | H | SMe | Cl | Cl | H |
| Z2.118 | Me | SMe | Cl | Cl | H |
| Z2.119 | H | SEt | Cl | Cl | H |
| Z2.120 | Me | SEt | Cl | Cl | H |
| Z2.121 | H | OMe | Cl | Br | Cl |
| Z2.122 | Me | OMe | Cl | Br | Cl |
| Z2.123 | H | OEt | Cl | Br | Cl |
| Z2.124 | Me | OEt | Cl | Br | Cl |
| Z2.125 | H | SMe | Cl | Br | Cl |
| Z2.126 | Me | SMe | Cl | Br | Cl |
| Z2.127 | H | SEt | Cl | Br | Cl |
| Z2.128 | Me | SEt | Cl | Br | Cl |
| Z2.129 | H | OMe | Cl | Cl | Br |
| Z2.130 | Me | OMe | Cl | Cl | Br |
| Z2.131 | H | OEt | Cl | Cl | Br |
| Z2.132 | Me | OEt | Cl | Cl | Br |
| Z2.133 | H | SMe | Cl | Cl | Br |
| Z2.134 | Me | SMe | Cl | Cl | Br |
| Z2.135 | H | SEt | Cl | Cl | Br |
| Z2.136 | Me | SEt | Cl | Cl | Br |

TABLE 36

Compounds of formula II-3
The invention is further illustrated by the preferred individual compounds of formula (II-3) listed below in Table 36.
Characterising data is given in Table 40.

(II-3)
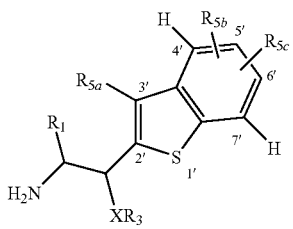

| Compound Number | $R_1$ | $XR_3$ | $R_{5a}$ | $R_{5b}$ | $R_{5c}$ |
|---|---|---|---|---|---|
| Z3.1 | H | OMe | Cl | 5'-Cl | H |
| Z3.2 | Me | OMe | Cl | 5'-Cl | H |
| Z3.3 | H | OEt | Cl | 5'-Cl | H |
| Z3.4 | Me | OEt | Cl | 5'-Cl | H |
| Z3.5 | H | SMe | Cl | 5'-Cl | H |
| Z3.6 | Me | SMe | Cl | 5'-Cl | H |
| Z3.7 | H | SEt | Cl | 5'-Cl | H |
| Z3.8 | Me | SEt | Cl | 5'-Cl | H |
| Z3.9 | H | OMe | Cl | 5'-Br | H |
| Z3.10 | Me | OMe | Cl | 5'-Br | H |
| Z3.11 | H | OEt | Cl | 5'-Br | H |
| Z3.12 | Me | OEt | Cl | 5'-Br | H |
| Z3.13 | H | SMe | Cl | 5'-Br | H |
| Z3.14 | Me | SMe | Cl | 5'-Br | H |
| Z3.15 | H | SEt | Cl | 5'-Br | H |
| Z3.16 | Me | SEt | Cl | 5'-Br | H |
| Z3.17 | H | OMe | Cl | 5'-≡-△ | H |
| Z3.18 | Me | OMe | Cl | 5'-≡-△ | H |
| Z3.19 | H | OEt | Cl | 5'-≡-△ | H |
| Z3.20 | Me | OEt | Cl | 5'-≡-△ | H |
| Z3.21 | H | SMe | Cl | 5'-≡-△ | H |
| Z3.22 | Me | SMe | Cl | 5'-≡-△ | H |
| Z3.23 | H | SEt | Cl | 5'-≡-△ | H |
| Z3.24 | Me | SEt | Cl | 5'-≡-△ | H |
| Z3.25 | H | OMe | Cl | 5'-C₆H₄-Cl | H |
| Z3.26 | Me | OMe | Cl | 5'-C₆H₄-Cl | H |
| Z3.27 | H | OEt | Cl | 5'-C₆H₄-Cl | H |
| Z3.28 | Me | OEt | Cl | 5'-C₆H₄-Cl | H |

TABLE 36-continued

Compounds of formula II-3
The invention is further illustrated by the preferred individual
compounds of formula (II-3) listed below in Table 36.
Characterising data is given in Table 40.

(II-3)

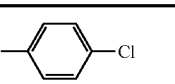

| Compound Number | $R_1$ | $XR_3$ | $R_{5a}$ | $R_{5b}$ | $R_{5c}$ |
|---|---|---|---|---|---|
| Z3.29 | H | SMe | Cl | 5'--Cl | H |
| Z3.30 | Me | SMe | Cl | 5'-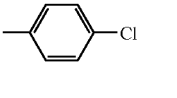-Cl | H |
| Z3.31 | H | SEt | Cl | 5'--Cl | H |
| Z3.32 | Me | SEt | Cl | 5'-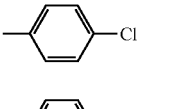-Cl | H |
| Z3.33 | H | OMe | Cl | 6'-Cl | H |
| Z3.34 | Me | OMe | Cl | 6'-Cl | H |
| Z3.35 | H | OEt | Cl | 6'-Cl | H |
| Z3.36 | Me | OEt | Cl | 6'-Cl | H |
| Z3.37 | H | SMe | Cl | 6'-Cl | H |
| Z3.38 | Me | SMe | Cl | 6'-Cl | H |
| Z3.39 | H | SEt | Cl | 6'-Cl | H |
| Z3.40 | Me | SEt | Cl | 6'-Cl | H |
| Z3.41 | H | OMe | Cl | 6'-Br | H |
| Z3.42 | Me | OMe | Cl | 6'-Br | H |
| Z3.43 | H | OEt | Cl | 6'-Br | H |
| Z3.44 | Me | OEt | Cl | 6'-Br | H |
| Z3.45 | H | SMe | Cl | 6'-Br | H |
| Z3.46 | Me | SMe | Cl | 6'-Br | H |
| Z3.47 | H | SEt | Cl | 6'-Br | H |
| Z3.48 | Me | SEt | Cl | 6'-Br | H |
| Z3.49 | H | OMe | Cl | 6'- | H |
| Z3.50 | Me | OMe | Cl | 6'-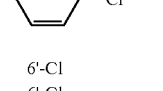 | H |
| Z3.51 | H | OEt | Cl | 6'-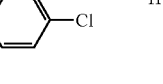 | H |
| Z3.52 | Me | OEt | Cl | 6'-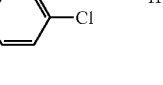 | H |
| Z3.53 | H | SMe | Cl | 6'-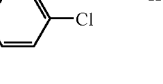 | H |
| Z3.54 | Me | SMe | Cl | 6'-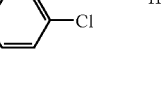 | H |
| Z3.55 | H | SEt | Cl | 6'-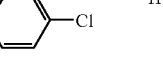 | H |
| Z3.56 | Me | SEt | Cl | 6'-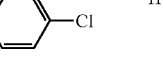 | H |
| Z3.57 | H | OMe | Cl | 6'-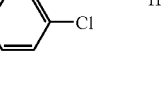-Cl | H |
| Z3.58 | Me | OMe | Cl | 6'-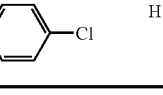-Cl | H |
| Z3.59 | H | OEt | Cl | 6'-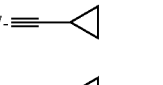-Cl | H |
| Z3.60 | Me | OEt | Cl | 6'-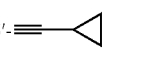-Cl | H |
| Z3.61 | H | SMe | Cl | 6'-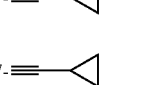-Cl | H |
| Z3.62 | Me | SMe | Cl | 6'-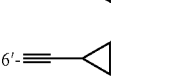-Cl | H |
| Z3.63 | H | SEt | Cl | 6'--Cl | H |
| Z3.64 | Me | SEt | Cl | 6'--Cl | H |

TABLE 37

Compounds of formula III-1
The invention is further illustrated by the preferred individual compounds of formula (II-1) listed below in Table 37.
Characterising data is given in Table 40.

(III-1)

| Compound Number | R$_1$ | XR$_3$ | R$_{5a}$ | R$_{5b}$ | R$_{5c}$ |
|---|---|---|---|---|---|
| Z4.1 | H | OMe | Cl | Cl | H |
| Z4.2 | Me | OMe | Cl | Cl | H |
| Z4.3 | H | OMe | Cl | Br | H |
| Z4.4 | Me | OMe | Cl | Br | H |
| Z4.5 | H | OEt | Cl | Cl | H |
| Z4.6 | Me | OEt | Cl | Cl | H |
| Z4.7 | H | OEt | Cl | Br | H |
| Z4.8 | Me | OEt | Cl | Br | H |
| Z4.9 | H | SMe | Cl | Cl | H |
| Z4.10 | Me | SMe | Cl | Cl | H |
| Z4.11 | H | SMe | Cl | Br | H |
| Z4.12 | Me | SMe | Cl | Br | H |
| Z4.13 | H | SEt | Cl | Cl | H |
| Z4.14 | Me | SEt | Cl | Cl | H |
| Z4.15 | H | SEt | Cl | Br | H |
| Z4.16 | Me | SEt | Cl | Br | H |
| Z4.17 | H | OMe | Cl |  | H |
| Z4.18 | Me | OMe | Cl |  | H |
| Z4.19 | H | OEt | Cl |  | H |
| Z4.20 | Me | OEt | Cl |  | H |
| Z4.21 | H | OMe | Cl |  | H |
| Z4.22 | Me | OMe | Cl |  | H |
| Z4.23 | H | OEt | Cl |  | H |
| Z4.24 | Me | OEt | Cl |  | H |
| Z4.25 | H | OMe | Cl |  | H |
| Z4.26 | Me | OMe | Cl |  | H |
| Z4.27 | H | OEt | Cl | 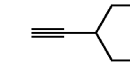 | H |
| Z4.28 | Me | OEt | Cl |  | H |
| Z4.29 | H | OMe | Cl |  | H |
| Z4.30 | Me | OMe | Cl |  | H |
| Z4.31 | H | OEt | Cl |  | H |
| Z4.32 | Me | OEt | Cl | 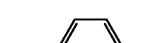 | H |
| Z4.33 | H | OMe | Cl | 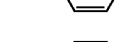 | H |
| Z4.34 | Me | OMe | Cl | 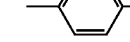 | H |
| Z4.35 | H | OEt | Cl | 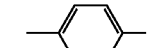 | H |
| Z4.36 | Me | OEt | Cl | 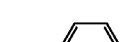 | H |
| Z4.37 | H | OMe | Cl | 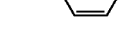 | H |
| Z4.38 | Me | OMe | Cl | 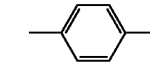 | H |
| Z4.39 | H | OEt | Cl | 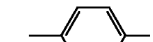 | H |
| Z4.40 | Me | OEt | Cl | 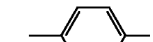 | H |
| Z4.41 | H | OMe | Cl | H | H |
| Z4.42 | Me | OMe | Cl | H | H |
| Z4.43 | H | OEt | Cl | H | H |
| Z4.44 | Me | OEt | Cl | H | H |
| Z4.45 | H | SMe | Cl | H | H |
| Z4.46 | Me | SMe | Cl | H | H |

TABLE 37-continued

Compounds of formula III-1
The invention is further illustrated by the preferred individual compounds of formula (II-1) listed below in Table 37.
Characterising data is given in Table 40.

(III-1)

| Compound Number | $R_1$ | $XR_3$ | $R_{5a}$ | $R_{5b}$ | $R_{5c}$ |
|---|---|---|---|---|---|
| Z4.47 | H | SEt | Cl | H | H |
| Z4.48 | Me | SEt | Cl | H | H |

TABLE 38

Compounds of formula III-2
The invention is further illustrated by the preferred individual compounds of formula (III-2) listed below in Table 38.
Characterising data is given in Table 40.

(III-2)

| Compound Number | $R_1$ | $XR_3$ | $R_{5a}$ | $R_{5b}$ | $R_{5c}$ |
|---|---|---|---|---|---|
| Z5.1 | H | OMe | Cl |  | Cl |
| Z5.2 | Me | OMe | Cl |  | Cl |
| Z5.3 | H | OEt | Cl |  | Cl |
| Z5.4 | Me | OEt | Cl |  | Cl |
| Z5.5 | H | SMe | Cl |  | Cl |
| Z5.6 | Me | SMe | Cl |  | Cl |
| Z5.7 | H | SEt | Cl |  | Cl |
| Z5.8 | Me | SEt | Cl |  | Cl |
| Z5.9 | H | OMe | Cl | Cl |  |
| Z5.10 | Me | OMe | Cl | Cl |  |
| Z5.11 | H | OEt | Cl | Cl |  |
| Z5.12 | Me | OEt | Cl | Cl |  |
| Z5.13 | H | SMe | Cl | Cl |  |
| Z5.14 | Me | SMe | Cl | Cl |  |
| Z5.15 | H | SEt | Cl | Cl | 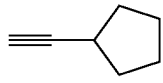 |
| Z5.16 | Me | SEt | Cl | Cl | 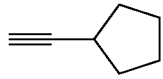 |
| Z5.17 | H | OMe | Cl | 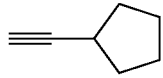 | Cl |
| Z5.18 | Me | OMe | Cl | 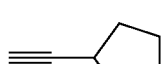 | Cl |
| Z5.19 | H | OEt | Cl |  | Cl |
| Z5.20 | Me | OEt | Cl |  | Cl |
| Z5.21 | H | SMe | Cl | 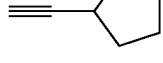 | Cl |
| Z5.22 | Me | SMe | Cl | 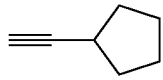 | Cl |
| Z5.23 | H | SEt | Cl | 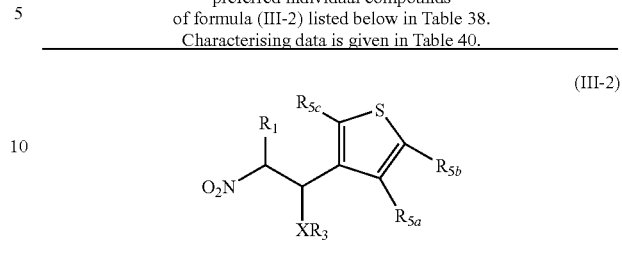 | Cl |
| Z5.24 | Me | SEt | Cl | | Cl |

TABLE 38-continued

Compounds of formula III-2
The invention is further illustrated by the preferred individual compounds of formula (III-2) listed below in Table 38.
Characterising data is given in Table 40.

(III-2)

| Compound Number | R$_1$ | XR$_3$ | R$_{5a}$ | R$_{5b}$ | R$_{5c}$ |
|---|---|---|---|---|---|
| Z5.25 | H | OMe | Cl | Cl | cyclopentyl-C≡C- |
| Z5.26 | Me | OMe | Cl | Cl | cyclopentyl-C≡C- |
| Z5.27 | H | OEt | Cl | Cl | cyclopentyl-C≡C- |
| Z5.28 | Me | OEt | Cl | Cl | cyclopentyl-C≡C- |
| Z5.29 | H | SMe | Cl | Cl | cyclopentyl-C≡C- |
| Z5.30 | Me | SMe | Cl | Cl | cyclopentyl-C≡C- |
| Z5.31 | H | SEt | Cl | Cl | cyclopentyl-C≡C- |
| Z5.32 | Me | SEt | Cl | Cl | cyclopentyl-C≡C- |
| Z5.33 | H | OMe | Cl | cyclohexyl-C≡C- | Cl |
| Z5.34 | Me | OMe | Cl | cyclohexyl-C≡C- | Cl |
| Z5.35 | H | OEt | Cl | cyclohexyl-C≡C- | Cl |
| Z5.36 | Me | OEt | Cl | cyclohexyl-C≡C- | Cl |
| Z5.37 | H | SMe | Cl | cyclohexyl-C≡C- | Cl |
| Z5.38 | Me | SMe | Cl | cyclohexyl-C≡C- | Cl |
| Z5.39 | H | SEt | Cl | cyclohexyl-C≡C- | Cl |
| Z5.40 | Me | SEt | Cl | cyclohexyl-C≡C- | Cl |
| Z5.41 | H | OMe | Cl | Cl | cyclohexyl-C≡C- |
| Z5.42 | Me | OMe | Cl | Cl | cyclohexyl-C≡C- |
| Z5.43 | H | OEt | Cl | Cl | cyclohexyl-C≡C- |
| Z5.44 | Me | OEt | Cl | Cl | cyclohexyl-C≡C- |
| Z5.45 | H | SMe | Cl | Cl | cyclohexyl-C≡C- |
| Z5.46 | Me | SMe | Cl | Cl | cyclohexyl-C≡C- |
| Z5.47 | H | SEt | Cl | Cl | cyclohexyl-C≡C- |
| Z5.48 | Me | SEt | Cl | Cl | cyclohexyl-C≡C- |
| Z5.49 | H | OMe | Cl | phenyl-C≡C- | Cl |
| Z5.50 | Me | OMe | Cl | phenyl-C≡C- | Cl |
| Z5.51 | H | OEt | Cl | phenyl-C≡C- | Cl |

TABLE 38-continued

Compounds of formula III-2
The invention is further illustrated by the preferred individual compounds of formula (III-2) listed below in Table 38.
Characterising data is given in Table 40.

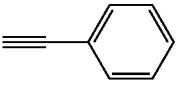
(III-2)

| Compound Number | R₁ | XR₃ | R₅ₐ | R₅ᵦ | R₅c |
|---|---|---|---|---|---|
| Z5.52 | Me | OEt | Cl | 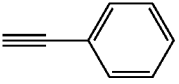 | Cl |
| Z5.53 | H | SMe | Cl | 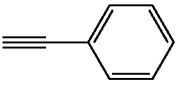 | Cl |
| Z5.54 | Me | SMe | Cl | 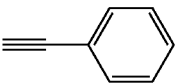 | Cl |
| Z5.55 | H | SEt | Cl | 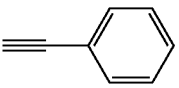 | Cl |
| Z5.56 | Me | SEt | Cl | 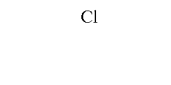 | Cl |
| Z5.57 | H | OMe | Cl | Cl | 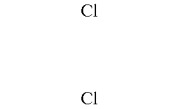 |
| Z5.58 | Me | OMe | Cl | Cl | 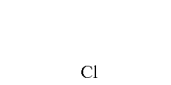 |
| Z5.59 | H | OEt | Cl | Cl |  |
| Z5.60 | Me | OEt | Cl | Cl |  |
| Z5.61 | H | SMe | Cl | Cl | 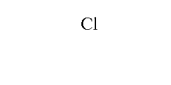 |
| Z5.62 | Me | SMe | Cl | Cl |  |
| Z5.63 | H | SEt | Cl | Cl |  |
| Z5.64 | Me | SEt | Cl | Cl | 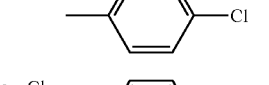 |
| Z5.65 | H | OMe | Cl | 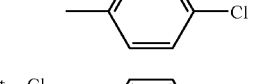 | Cl |
| Z5.66 | Me | OMe | Cl | 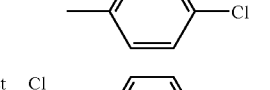 | Cl |
| Z5.67 | H | OEt | Cl | 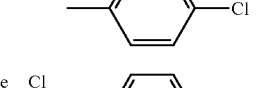 | Cl |
| Z5.68 | Me | OEt | Cl | 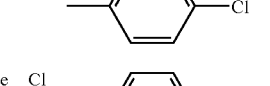 | Cl |
| Z5.69 | H | SMe | Cl | 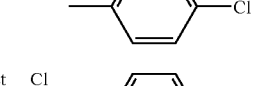 | Cl |
| Z5.70 | Me | SMe | Cl | 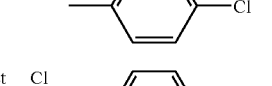 | Cl |
| Z5.71 | H | SEt | Cl | 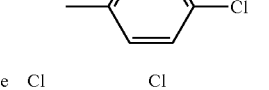 | Cl |
| Z5.72 | Me | SEt | Cl | 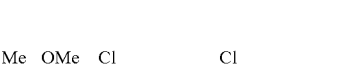 | Cl |
| Z5.73 | H | OMe | Cl | Cl |  |
| Z5.74 | Me | OMe | Cl | Cl | 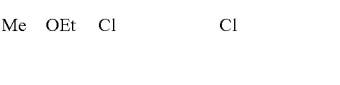 |
| Z5.75 | H | OEt | Cl | Cl |  |
| Z5.76 | Me | OEt | Cl | Cl |  |
| Z5.77 | H | SMe | Cl | Cl | |

TABLE 38-continued

Compounds of formula III-2
The invention is further illustrated by the preferred individual compounds of formula (III-2) listed below in Table 38.
Characterising data is given in Table 40.

(III-2)

| Compound Number | $R_1$ | $XR_3$ | $R_{5a}$ | $R_{5b}$ | $R_{5c}$ |
|---|---|---|---|---|---|
| Z5.78 | Me | SMe | Cl | Cl | 4-Cl-phenyl |
| Z5.79 | H | SEt | Cl | Cl | 4-Cl-phenyl |
| Z5.80 | Me | SEt | Cl | Cl | 4-Cl-phenyl |
| Z5.81 | H | OMe | Cl | 4-F-phenyl | Cl |
| Z5.82 | Me | OMe | Cl | 4-F-phenyl | Cl |
| Z5.83 | H | OEt | Cl | 4-F-phenyl | Cl |
| Z5.84 | Me | OEt | Cl | 4-F-phenyl | Cl |
| Z5.85 | H | SMe | Cl | 4-F-phenyl | Cl |
| Z5.86 | Me | SMe | Cl | 4-F-phenyl | Cl |
| Z5.87 | H | SEt | Cl | 4-F-phenyl | Cl |
| Z5.88 | Me | SEt | Cl | 4-F-phenyl | Cl |
| Z5.89 | H | OMe | Cl | Cl | 4-F-phenyl |
| Z5.90 | Me | OMe | Cl | Cl | 4-F-phenyl |
| Z5.91 | H | OEt | Cl | Cl | 4-F-phenyl |
| Z5.92 | Me | OEt | Cl | Cl | 4-F-phenyl |
| Z5.93 | H | SMe | Cl | Cl | 4-F-phenyl |
| Z5.94 | Me | SMe | Cl | Cl | 4-F-phenyl |
| Z5.95 | H | SEt | Cl | Cl | 4-F-phenyl |
| Z5.96 | Me | SEt | Cl | Cl | 4-F-phenyl |
| Z5.97 | H | OMe | Cl | Cl | Cl |
| Z5.98 | Me | OMe | Cl | Cl | Cl |
| Z5.99 | H | OEt | Cl | Cl | Cl |
| Z5.100 | Me | OEt | Cl | Cl | Cl |
| Z5.101 | H | SMe | Cl | Cl | Cl |
| Z5.102 | Me | SMe | Cl | Cl | Cl |
| Z5.103 | H | SEt | Cl | Cl | Cl |
| Z5.104 | Me | SEt | Cl | Cl | Cl |
| Z5.105 | H | OMe | Cl | H | Cl |
| Z5.106 | Me | OMe | Cl | H | Cl |
| Z5.107 | H | OEt | Cl | H | Cl |
| Z5.108 | Me | OEt | Cl | H | Cl |
| Z5.109 | H | SMe | Cl | H | Cl |
| Z5.110 | Me | SMe | Cl | H | Cl |
| Z5.111 | H | SEt | Cl | H | Cl |
| Z5.112 | Me | SEt | Cl | H | Cl |
| Z5.113 | H | OMe | Cl | Cl | H |
| Z5.114 | Me | OMe | Cl | Cl | H |
| Z5.115 | H | OEt | Cl | Cl | H |
| Z5.116 | Me | OEt | Cl | Cl | H |
| Z5.117 | H | SMe | Cl | Cl | H |
| Z5.118 | Me | SMe | Cl | Cl | H |
| Z5.119 | H | SEt | Cl | Cl | H |
| Z5.120 | Me | SEt | Cl | Cl | H |
| Z5.121 | H | OMe | Cl | Br | Cl |
| Z5.122 | Me | OMe | Cl | Br | Cl |
| Z5.123 | H | OEt | Cl | Br | Cl |
| Z5.124 | Me | OEt | Cl | Br | Cl |
| Z5.125 | H | SMe | Cl | Br | Cl |
| Z5.126 | Me | SMe | Cl | Br | Cl |
| Z5.127 | H | SEt | Cl | Br | Cl |
| Z5.128 | Me | SEt | Cl | Br | Cl |
| Z5.129 | H | OMe | Cl | Cl | Br |
| Z5.130 | Me | OMe | Cl | Cl | Br |
| Z5.131 | H | OEt | Cl | Cl | Br |

TABLE 38-continued

Compounds of formula III-2
The invention is further illustrated by the
preferred individual compounds
of formula (III-2) listed below in Table 38.
Characterising data is given in Table 40.

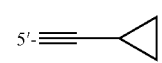

(III-2)

| Compound Number | $R_1$ | $XR_3$ | $R_{5a}$ | $R_{5b}$ | $R_{5c}$ |
|---|---|---|---|---|---|
| Z5.132 | Me | OEt | Cl | Cl | Br |
| Z5.133 | H | SMe | Cl | Cl | Br |
| Z5.134 | Me | SMe | Cl | Cl | Br |
| Z5.135 | H | SEt | Cl | Cl | Br |
| Z5.136 | Me | SEt | Cl | Cl | Br |

TABLE 39

Compounds of formula III-3
The invention is further illustrated by the preferred individual
compounds of formula (III-3) listed below in Table 39.
Characterising data is given in Table 40.

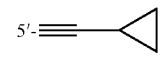

(III-3)

| Compound Number | $R_1$ | $XR_3$ | $R_{5a}$ | $R_{5b}$ | $R_{5c}$ |
|---|---|---|---|---|---|
| Z6.1 | H | OMe | Cl | 5'-Cl | H |
| Z6.2 | Me | OMe | Cl | 5'-Cl | H |
| Z6.3 | H | OEt | Cl | 5'-Cl | H |
| Z6.4 | Me | OEt | Cl | 5'-Cl | H |
| Z6.5 | H | SMe | Cl | 5'-Cl | H |
| Z6.6 | Me | SMe | Cl | 5'-Cl | H |
| Z6.7 | H | SEt | Cl | 5'-Cl | H |
| Z6.8 | Me | SEt | Cl | 5'-Cl | H |
| Z6.9 | H | OMe | Cl | 5'-Br | H |
| Z6.10 | Me | OMe | Cl | 5'-Br | H |
| Z6.11 | H | OEt | Cl | 5'-Br | H |
| Z6.12 | Me | OEt | Cl | 5'-Br | H |
| Z6.13 | H | SMe | Cl | 5'-Br | H |
| Z6.14 | Me | SMe | Cl | 5'-Br | H |
| Z6.15 | H | SEt | Cl | 5'-Br | H |
| Z6.16 | Me | SEt | Cl | 5'-Br | H |
| Z6.17 | H | OMe | Cl | 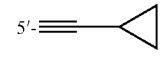 | H |
| Z6.18 | Me | OMe | Cl | 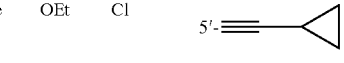 | H |
| Z6.19 | H | OEt | Cl |  | H |

TABLE 39-continued

Compounds of formula III-3
The invention is further illustrated by the preferred individual
compounds of formula (III-3) listed below in Table 39.
Characterising data is given in Table 40.

(III-3)

| Compound Number | $R_1$ | $XR_3$ | $R_{5a}$ | $R_{5b}$ | $R_{5c}$ |
|---|---|---|---|---|---|
| Z6.20 | Me | OEt | Cl |  | H |
| Z6.21 | H | SMe | Cl | 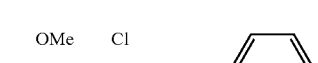 | H |
| Z6.22 | Me | SMe | Cl |  | H |
| Z6.23 | H | SEt | Cl | 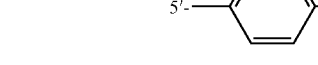 | H |
| Z6.24 | Me | SEt | Cl | 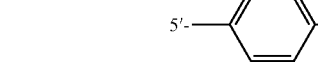 | H |
| Z6.25 | H | OMe | Cl | 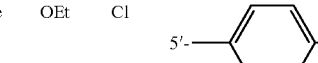 | H |
| Z6.26 | Me | OMe | Cl | 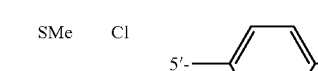 | H |
| Z6.27 | H | OEt | Cl |  | H |
| Z6.28 | Me | OEt | Cl | 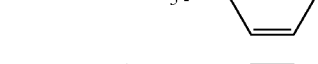 | H |
| Z6.29 | H | SMe | Cl | 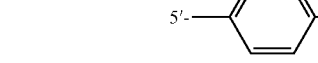 | H |
| Z6.30 | Me | SMe | Cl | | H |
| Z6.31 | H | SEt | Cl | | H |
| Z6.32 | Me | SEt | Cl | | H |
| Z6.33 | H | OMe | Cl | 6'-Cl | H |
| Z6.34 | Me | OMe | Cl | 6'-Cl | H |
| Z6.35 | H | OEt | Cl | 6'-Cl | H |

TABLE 39-continued

Compounds of formula III-3
The invention is further illustrated by the preferred individual compounds of formula (III-3) listed below in Table 39.
Characterising data is given in Table 40.

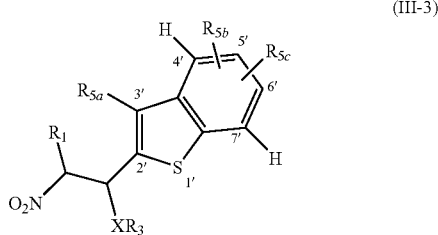

(III-3)

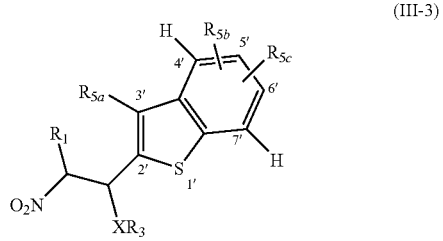

(III-3)

| Compound Number | R₁ | XR₃ | R₅ₐ | R₅ᵦ | R₅c |
|---|---|---|---|---|---|
| Z6.36 | Me | OEt | Cl | 6'-Cl | H |
| Z6.37 | H | SMe | Cl | 6'-Cl | H |
| Z6.38 | Me | SMe | Cl | 6'-Cl | H |
| Z6.39 | H | SEt | Cl | 6'-Cl | H |
| Z6.40 | Me | SEt | Cl | 6'-Cl | H |
| Z6.41 | H | OMe | Cl | 6'-Br | H |
| Z6.42 | Me | OMe | Cl | 6'-Br | H |
| Z6.43 | H | OEt | Cl | 6'-Br | H |
| Z6.44 | Me | OEt | Cl | 6'-Br | H |
| Z6.45 | H | SMe | Cl | 6'-Br | H |
| Z6.46 | Me | SMe | Cl | 6'-Br | H |
| Z6.47 | H | SEt | Cl | 6'-Br | H |
| Z6.48 | Me | SEt | Cl | 6'-Br | H |
| Z6.49 | H | OMe | Cl | 6'-≡-cyclopropyl | H |
| Z6.50 | Me | OMe | Cl | 6'-≡-cyclopropyl | H |
| Z6.51 | H | OEt | Cl | 6'-≡-cyclopropyl | H |
| Z6.52 | Me | OEt | Cl | 6'-≡-cyclopropyl | H |
| Z6.53 | H | SMe | Cl | 6'-≡-cyclopropyl | H |
| Z6.54 | Me | SMe | Cl | 6'-≡-cyclopropyl | H |
| Z6.55 | H | SEt | Cl | 6'-≡-cyclopropyl | H |
| Z6.56 | Me | SEt | Cl | 6'-≡-cyclopropyl | H |
| Z6.57 | H | OMe | Cl | 6'-(4-Cl-phenyl) | H |
| Z6.58 | Me | OMe | Cl | 6'-(4-Cl-phenyl) | H |
| Z6.59 | H | OEt | Cl | 6'-(4-Cl-phenyl) | H |
| Z6.60 | Me | OEt | Cl | 6'-(4-Cl-phenyl) | H |
| Z6.61 | H | SMe | Cl | 6'-(4-Cl-phenyl) | H |
| Z6.62 | Me | SMe | Cl | 6'-(4-Cl-phenyl) | H |
| Z6.63 | H | SEt | Cl | 6'-(4-Cl-phenyl) | H |
| Z6.64 | Me | SEt | Cl | 6'-(4-Cl-phenyl) | H |

Physical Data (Melting Points in ° C.):

Throughout this description, temperatures are given in degrees Celsius; "NMR" means nuclear magnetic resonance spectrum; MS is mass spectrum; and "%" is percent by weight, unless corresponding concentrations are indicated in other units.

The following abbreviations are used throughout this description:

| | |
|---|---|
| m.p. = melting point | b.p. = boiling point. |
| S = singlet | br = broad |
| d = doublet | dd = doublet of doublets |
| t = triplet | q = quartet |
| m = multiplet | ppm = parts per million |

Table 40 shows selected melting points, and NMR data, all with CDCl₃ as solvent, if not otherwise stated; if a mixture of solvents is present, this is indicated as, for example, (CDCl₃/d₆-DMSO).

TABLE 40

| Cpd No. | ¹H-NMR data: (ppm/multiplicity/number of Hs). | m.p./(° C.) |
|---|---|---|
| 22.2 | — | 128-132 |
| 22.4 | — | 115-125 |

TABLE 40-continued

| Cpd No. | ¹H-NMR data: (ppm/multiplicity/number of Hs). | m.p./(° C.) |
|---|---|---|
| 22.33 | — | 139-141 |
| 22.34 | — | 150-155 |
| 22.36 | — | 130-135 |
| 25.34 | — | resin |
| 29.34 | — | resin |
| 30.2 | — | 115-125 |
| 30.4 | — | 112-116 |
| 30.33 | — | 117-120 |
| 30.34 | — | resin |
| 33.1 | — | resin |
| 33.2 | — | 125-130 |
| 33.4 | — | 100-104 |
| 33.33 | — | 141-143 |
| 33.34 | — | resin |
| 33.36 | — | 150-155 |

Tables 1a to 13a: Compounds of Formula I-1a

The invention is further illustrated by the preferred individual compounds of formula (I-1a) listed below in Tables 1a to 13a.

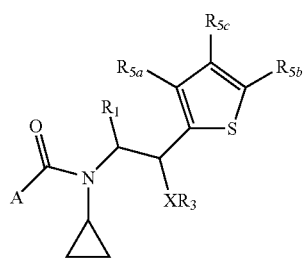

(I-1a)

Each of Tables 1a to 13a, which follow the Table Va below, comprises 48 compounds of the formula (I-1a) in which $R_1$, X—$R_3$, $R_{5a}$, $R_{5b}$ and $R_{5c}$, have the values given in Table Va and A has the value given in the relevant Table 1a to 13a. Thus Table 1a corresponds to Table Va when Va is 1 and A has the value given under the Table 1a heading, Table 2a corresponds to Table V when Va is 2 and A has the value given under the Table 2a heading, and so on for Tables 3a to 13a.

TABLE Va

| Compound Number | $R_1$ | $XR_3$ | $R_{5a}$ | $R_{5b}$ | $R_{5c}$ |
|---|---|---|---|---|---|
| Va.1 | H | OMe | Cl | Cl | H |
| Va.2 | Me | OMe | Cl | Cl | H |
| Va.3 | H | OMe | Cl | Br | H |
| Va.4 | Me | OMe | Cl | Br | H |
| Va.5 | H | OEt | Cl | Cl | H |
| Va.6 | Me | OEt | Cl | Cl | H |
| Va.7 | H | OEt | Cl | Br | H |
| Va.8 | Me | OEt | Cl | Br | H |
| Va.9 | H | SMe | Cl | Cl | H |
| Va.10 | Me | SMe | Cl | Cl | H |
| Va.11 | H | SMe | Cl | Br | H |
| Va.12 | Me | SMe | Cl | Br | H |
| Va.13 | H | SEt | Cl | Cl | H |
| Va.14 | Me | SEt | Cl | Cl | H |
| Va.15 | H | SEt | Cl | Br | H |
| Va.16 | Me | SEt | Cl | Br | H |
| Va.17 | H | OMe | Cl | ≡-cyclopropyl | H |
| Va.18 | Me | OMe | Cl | ≡-cyclopropyl | H |
| Va.19 | H | OEt | Cl | ≡-cyclopropyl | H |
| Va.20 | Me | OEt | Cl | ≡-cyclopropyl | H |
| Va.21 | H | OMe | Cl | ≡-cyclopentyl | H |
| Va.22 | Me | OMe | Cl | ≡-cyclopentyl | H |
| Va.23 | H | OEt | Cl | ≡-cyclopentyl | H |
| Va.24 | Me | OEt | Cl | ≡-cyclopentyl | H |
| Va.25 | H | OMe | Cl | ≡-cyclohexyl | H |
| Va.26 | Me | OMe | Cl | ≡-cyclohexyl | H |
| Va.27 | H | OEt | Cl | ≡-cyclohexyl | H |
| Va.28 | Me | OEt | Cl | ≡-cyclohexyl | H |
| Va.29 | H | OMe | Cl | ≡-phenyl | H |
| Va.30 | Me | OMe | Cl | ≡-phenyl | H |
| Va.31 | H | OEt | Cl | ≡-phenyl | H |
| Va.32 | Me | OEt | Cl | ≡-phenyl | H |
| Va.33 | H | OMe | Cl | -C₆H₄-Cl (4-Cl-phenyl) | H |
| Va.34 | Me | OMe | Cl | -C₆H₄-Cl (4-Cl-phenyl) | H |

TABLE Va-continued

| Compound Number | $R_1$ | $XR_3$ | $R_{5a}$ | $R_{5b}$ | $R_{5c}$ |
|---|---|---|---|---|---|
| Va.35 | H | OEt | Cl | 4-Cl-phenyl | H |
| Va.36 | Me | OEt | Cl | 4-Cl-phenyl | H |
| Va.37 | H | OMe | Cl | 4-F-phenyl | H |
| Va.38 | Me | OMe | Cl | 4-F-phenyl | H |
| Va.39 | H | OEt | Cl | 4-F-phenyl | H |
| Va.40 | Me | OEt | Cl | 4-F-phenyl | H |
| Va.41 | H | OMe | Cl | H | H |
| Va.42 | Me | OMe | Cl | H | H |
| Va.43 | H | OEt | Cl | H | H |
| Va.44 | Me | OEt | Cl | H | H |
| Va.45 | H | SMe | Cl | H | H |
| Va.46 | Me | SMe | Cl | H | H |
| Va.47 | H | SEt | Cl | H | H |
| Va.48 | Me | SEt | Cl | H | H |

Table 1a provides 48 compounds of formula (I-1a), wherein A is

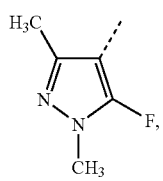

wherein the dashed lines indicate the point of attachment of the group A to the amide group, and $R_1$, X—$R_3$, $R_{5a}$, $R_{5b}$ and $R_{5c}$ are as defined in Table Va. For example, compound 1a.1 has the following structure:

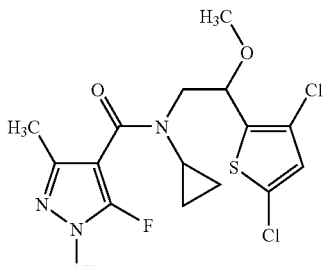

(1a.1)

Table 2a provides 48 compounds of formula (I-1a) wherein A is

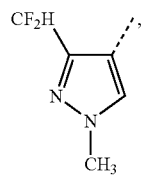

wherein the dashed lines indicate the point of attachment of the group A to the amide group, and $R_1$, X—$R_3$, $R_{5a}$, $R_{5b}$ and $R_{5c}$ are as defined in Table Va.

Table 3a provides 48 compounds of formula (I-1a) wherein A is

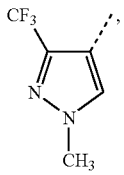

wherein the dashed lines indicate the point of attachment of the group A to the amide group, and $R_1$, X—$R_3$, $R_{5a}$, $R_{5b}$ and $R_{5c}$ are as defined in Table Va.

Table 4a provides 48 compounds of formula (I-1a) wherein A is

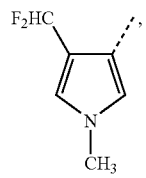

wherein the dashed lines indicate the point of attachment of the group A to the amide group, and $R_1$, X—$R_3$, $R_{5a}$, $R_{5b}$ and $R_{5c}$ are as defined in Table Va.

Table 5a provides 48 compounds of formula (I-1a) wherein A is

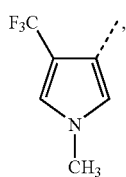

wherein the dashed lines indicate the point of attachment of the group A to the amide group, and $R_1$, $X$—$R_3$, $R_{5a}$, $R_{5b}$ and $R_{5c}$ are as defined in Table Va.

Table 6a provides 48 compounds of formula (I-1a) wherein A is

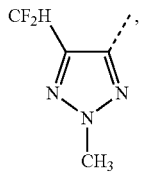

wherein the dashed lines indicate the point of attachment of the group A to the amide group, and $R_1$, $X$—$R_3$, $R_{5a}$, $R_{5b}$ and $R_{5c}$ are as defined in Table Va.

Table 7a provides 48 compounds of formula (I-1a) wherein A is

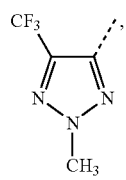

wherein the dashed lines indicate the point of attachment of the group A to the amide group, and $R_1$, $X$—$R_3$, $R_{5a}$, $R_{5b}$ and $R_{5c}$ are as defined in Table Va.

Table 8a provides 48 compounds of formula (I-1a) wherein A is

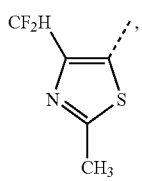

wherein the dashed lines indicate the point of attachment of the group A to the amide group, and $R_1$, $X$—$R_3$, $R_{5a}$, $R_{5b}$ and $R_{5c}$ are as defined in Table Va.

Table 9a provides 48 compounds of formula (I-1a) wherein A is

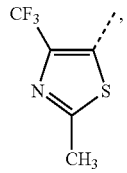

wherein the dashed lines indicate the point of attachment of the group A to the amide group, and $R_1$, $X$—$R_3$, $R_{5a}$, $R_{5b}$ and $R_{5c}$ are as defined in Table Va.

Table 10a provides 48 compounds of formula (I-1a) wherein A is

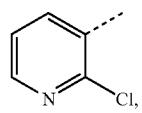

wherein the dashed lines indicate the point of attachment of the group A to the amide group, and $R_1$, $X$—$R_3$, $R_{5a}$, $R_{5b}$ and $R_{5c}$ are as defined in Table Va.

Table 11a provides 48 compounds of formula (I-1a) wherein A is

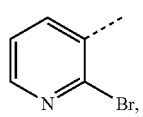

wherein the dashed lines indicate the point of attachment of the group A to the amide group, and $R_1$, $X$—$R_3$, $R_{5a}$, $R_{5b}$ and $R_{5c}$ are as defined in Table Va.

Table 12a provides 48 compounds of formula (I-1a) wherein A is

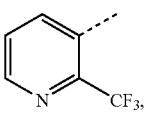

wherein the dashed lines indicate the point of attachment of the group A to the amide group, and $R_1$, $X$—$R_3$, $R_{5a}$, $R_{5b}$ and $R_{5c}$ are as defined in Table Va.

Table 13a provides 48 compounds of formula (I-1a) wherein A is

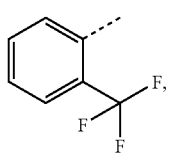

wherein the dashed lines indicate the point of attachment of the group A to the amide group, and $R_1$, $X$—$R_3$, $R_{5a}$, $R_{5b}$ and $R_{5c}$ are as defined in Table Va.

Tables 14a to 20a: Compounds of Formula I-2a:

The invention is further illustrated by the preferred individual compounds of formula (I-2a) listed below in Tables 14a to 20a.

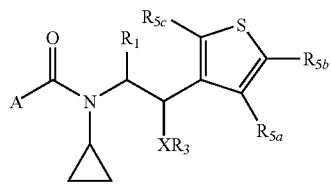

(I-2a)

Each of Tables 14a to 20a, which follow the Table Wa below, comprises 136 compounds of the formula (I-2a) in which $R_1$, X—$R_3$, $R_{5a}$, $R_{5b}$ and $R_{5c}$ have the values given in Table Wa and A has the value given in the relevant Table 14a to 20a. Thus Table 14 corresponds to Table Wa when Wa is 14 and A has the value given under the Table 14a heading, Table 15a corresponds to Table Wa when Wa is 15 and A has the value given under the Table 15a heading, and so on for Tables 16a to 20a.

TABLE Wa

| Compound Number | $R_1$ | $XR_3$ | $R_{5a}$ | $R_{5b}$ | $R_{5c}$ |
|---|---|---|---|---|---|
| Wa.1 | H | OMe | Cl | ≡─◁ | Cl |
| Wa.2 | Me | OMe | Cl | ≡─◁ | Cl |
| Wa.3 | H | OEt | Cl | ≡─◁ | Cl |
| Wa.4 | Me | OEt | Cl | ≡─◁ | Cl |
| Wa.5 | H | SMe | Cl | ≡─◁ | Cl |
| Wa.6 | Me | SMe | Cl | ≡─◁ | Cl |
| Wa.7 | H | SEt | Cl | ≡─◁ | Cl |
| Wa.8 | Me | SEt | Cl | ≡─◁ | Cl |
| Wa.9 | H | OMe | Cl | Cl | ≡─◁ |
| Wa.10 | Me | OMe | Cl | Cl | ≡─◁ |
| Wa.11 | H | OEt | Cl | Cl | ≡─◁ |
| Wa.12 | Me | OEt | Cl | Cl | ≡─◁ |
| Wa.13 | H | SMe | Cl | Cl | ≡─◁ |
| Wa.14 | Me | SMe | Cl | Cl | ≡─◁ |
| Wa.15 | H | SEt | Cl | Cl | ≡─◁ |
| Wa.16 | Me | SEt | Cl | Cl | ≡─◁ |
| Wa.17 | H | OMe | Cl | ≡─⬠ | Cl |
| Wa.18 | Me | OMe | Cl | ≡─⬠ | Cl |
| Wa.19 | H | OEt | Cl | ≡─⬠ | Cl |
| Wa.20 | Me | OEt | Cl | ≡─⬠ | Cl |
| Wa.21 | H | SMe | Cl | ≡─⬠ | Cl |
| Wa.22 | Me | SMe | Cl | ≡─⬠ | Cl |
| Wa.23 | H | SEt | Cl | ≡─⬠ | Cl |
| Wa.24 | Me | SEt | Cl | ≡─⬠ | Cl |
| Wa.25 | H | OMe | Cl | Cl | ≡─⬠ |
| Wa.26 | Me | OMe | Cl | Cl | ≡─⬠ |
| Wa.27 | H | OEt | Cl | Cl | ≡─⬠ |
| Wa.28 | Me | OEt | Cl | Cl | ≡─⬠ |
| Wa.29 | H | SMe | Cl | Cl | ≡─⬠ |
| Wa.30 | Me | SMe | Cl | Cl | ≡─⬠ |
| Wa.31 | H | SEt | Cl | Cl | ≡─⬠ |
| Wa.32 | Me | SEt | Cl | Cl | ≡─⬠ |
| Wa.33 | H | OMe | Cl | ≡─⬡ | Cl |
| Wa.34 | Me | OMe | Cl | ≡─⬡ | Cl |
| Wa.35 | H | OEt | Cl | ≡─⬡ | Cl |

TABLE Wa-continued

| Compound Number | $R_1$ | $XR_3$ | $R_{5a}$ | $R_{5b}$ | $R_{5c}$ |
|---|---|---|---|---|---|
| Wa.36 | Me | OEt | Cl | ethynyl-cyclohexyl | Cl |
| Wa.37 | H | SMe | Cl | ethynyl-cyclohexyl | Cl |
| Wa.38 | Me | SMe | Cl | ethynyl-cyclohexyl | Cl |
| Wa.39 | H | SEt | Cl | ethynyl-cyclohexyl | Cl |
| Wa.40 | Me | SEt | Cl | ethynyl-cyclohexyl | Cl |
| Wa.41 | H | OMe | Cl | Cl | ethynyl-cyclohexyl |
| Wa.42 | Me | OMe | Cl | Cl | ethynyl-cyclohexyl |
| Wa.43 | H | OEt | Cl | Cl | ethynyl-cyclohexyl |
| Wa.44 | Me | OEt | Cl | Cl | ethynyl-cyclohexyl |
| Wa.45 | H | SMe | Cl | Cl | ethynyl-cyclohexyl |
| Wa.46 | Me | SMe | Cl | Cl | ethynyl-cyclohexyl |
| Wa.47 | H | SEt | Cl | Cl | ethynyl-cyclohexyl |
| Wa.48 | Me | SEt | Cl | Cl | ethynyl-cyclohexyl |
| Wa.49 | H | OMe | Cl | ethynyl-phenyl | Cl |
| Wa.50 | Me | OMe | Cl | ethynyl-phenyl | Cl |
| Wa.51 | H | OEt | Cl | ethynyl-phenyl | Cl |
| Wa.52 | Me | OEt | Cl | ethynyl-phenyl | Cl |
| Wa.53 | H | SMe | Cl | ethynyl-phenyl | Cl |
| Wa.54 | Me | SMe | Cl | ethynyl-phenyl | Cl |
| Wa.55 | H | SEt | Cl | ethynyl-phenyl | Cl |
| Wa.56 | Me | SEt | Cl | ethynyl-phenyl | Cl |
| Wa.57 | H | OMe | Cl | Cl | ethynyl-phenyl |
| Wa.58 | Me | OMe | Cl | Cl | ethynyl-phenyl |
| Wa.59 | H | OEt | Cl | Cl | ethynyl-phenyl |
| Wa.60 | Me | OEt | Cl | Cl | ethynyl-phenyl |
| Wa.61 | H | SMe | Cl | Cl | ethynyl-phenyl |
| Wa.62 | Me | SMe | Cl | Cl | ethynyl-phenyl |
| Wa.63 | H | SEt | Cl | Cl | ethynyl-phenyl |
| Wa.64 | Me | SEt | Cl | Cl | ethynyl-phenyl |
| Wa.65 | H | OMe | Cl | 4-Cl-phenyl | Cl |
| Wa.66 | Me | OMe | Cl | 4-Cl-phenyl | Cl |
| Wa.67 | H | OEt | Cl | 4-Cl-phenyl | Cl |
| Wa.68 | Me | OEt | Cl | 4-Cl-phenyl | Cl |
| Wa.69 | H | SMe | Cl | 4-Cl-phenyl | Cl |
| Wa.70 | Me | SMe | Cl | 4-Cl-phenyl | Cl |
| Wa.71 | H | SEt | Cl | 4-Cl-phenyl | Cl |
| Wa.72 | Me | SEt | Cl | 4-Cl-phenyl | Cl |
| Wa.73 | H | OMe | Cl | Cl | 4-Cl-phenyl |

TABLE Wa-continued

| Compound Number | R₁ | XR₃ | R₅ₐ | R₅ᵦ | R₅c |
|---|---|---|---|---|---|
| Wa.74 | Me | OMe | Cl | Cl | 4-Cl-C₆H₄ |
| Wa.75 | H | OEt | Cl | Cl | 4-Cl-C₆H₄ |
| Wa.76 | Me | OEt | Cl | Cl | 4-Cl-C₆H₄ |
| Wa.77 | H | SMe | Cl | Cl | 4-Cl-C₆H₄ |
| Wa.78 | Me | SMe | Cl | Cl | 4-Cl-C₆H₄ |
| Wa.79 | H | SEt | Cl | Cl | 4-Cl-C₆H₄ |
| Wa.80 | Me | SEt | Cl | Cl | 4-Cl-C₆H₄ |
| Wa.81 | H | OMe | Cl | 4-F-C₆H₄ | Cl |
| Wa.82 | Me | OMe | Cl | 4-F-C₆H₄ | Cl |
| Wa.83 | H | OEt | Cl | 4-F-C₆H₄ | Cl |
| Wa.84 | Me | OEt | Cl | 4-F-C₆H₄ | Cl |
| Wa.85 | H | SMe | Cl | 4-F-C₆H₄ | Cl |
| Wa.86 | Me | SMe | Cl | 4-F-C₆H₄ | Cl |
| Wa.87 | H | SEt | Cl | 4-F-C₆H₄ | Cl |
| Wa.88 | Me | SEt | Cl | 4-F-C₆H₄ | Cl |
| Wa.89 | H | OMe | Cl | Cl | 4-F-C₆H₄ |
| Wa.90 | Me | OMe | Cl | Cl | 4-F-C₆H₄ |
| Wa.91 | H | OEt | Cl | Cl | 4-F-C₆H₄ |
| Wa.92 | Me | OEt | Cl | Cl | 4-F-C₆H₄ |
| Wa.93 | H | SMe | Cl | Cl | 4-F-C₆H₄ |
| Wa.94 | Me | SMe | Cl | Cl | 4-F-C₆H₄ |
| Wa.95 | H | SEt | Cl | Cl | 4-F-C₆H₄ |
| Wa.96 | Me | SEt | Cl | Cl | 4-F-C₆H₄ |
| Wa.97 | H | OMe | Cl | Cl | Cl |
| Wa.98 | Me | OMe | Cl | Cl | Cl |
| Wa.99 | H | OEt | Cl | Cl | Cl |
| Wa.100 | Me | OEt | Cl | Cl | Cl |
| Wa.101 | H | SMe | Cl | Cl | Cl |
| Wa.102 | Me | SMe | Cl | Cl | Cl |
| Wa.103 | H | SEt | Cl | Cl | Cl |
| Wa.104 | Me | SEt | Cl | Cl | Cl |
| Wa.105 | H | OMe | Cl | H | Cl |
| Wa.106 | Me | OMe | Cl | H | Cl |
| Wa.107 | H | OEt | Cl | H | Cl |
| Wa.108 | Me | OEt | Cl | H | Cl |
| Wa.109 | H | SMe | Cl | H | Cl |
| Wa.110 | Me | SMe | Cl | H | Cl |
| Wa.111 | H | SEt | Cl | H | Cl |
| Wa.112 | Me | SEt | Cl | H | Cl |
| Wa.113 | H | OMe | Cl | Cl | H |
| Wa.114 | Me | OMe | Cl | Cl | H |
| Wa.115 | H | OEt | Cl | Cl | H |
| Wa.116 | Me | OEt | Cl | Cl | H |
| Wa.117 | H | SMe | Cl | Cl | H |
| Wa.118 | Me | SMe | Cl | Cl | H |
| Wa.119 | H | SEt | Cl | Cl | H |
| Wa.120 | Me | SEt | Cl | Cl | H |
| Wa.121 | H | OMe | Cl | Br | Cl |
| Wa.122 | Me | OMe | Cl | Br | Cl |
| Wa.123 | H | OEt | Cl | Br | Cl |
| Wa.124 | Me | OEt | Cl | Br | Cl |
| Wa.125 | H | SMe | Cl | Br | Cl |
| Wa.126 | Me | SMe | Cl | Br | Cl |
| Wa.127 | H | SEt | Cl | Br | Cl |
| Wa.128 | Me | SEt | Cl | Br | Cl |
| Wa.129 | H | OMe | Cl | Cl | Br |
| Wa.130 | Me | OMe | Cl | Cl | Br |
| Wa.131 | H | OEt | Cl | Cl | Br |
| Wa.132 | Me | OEt | Cl | Cl | Br |
| Wa.133 | H | SMe | Cl | Cl | Br |
| Wa.134 | Me | SMe | Cl | Cl | Br |
| Wa.135 | H | SEt | Cl | Cl | Br |
| Wa.136 | Me | SEt | Cl | Cl | Br |

Table 14a provides 136 compounds of formula (I-2a), wherein A is

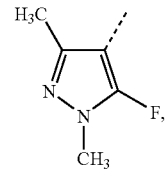

wherein the dashed lines indicate the point of attachment of the group A to the amide group, and $R_1$, X—$R_3$, $R_{5a}$, $R_{5b}$ and $R_{5c}$ are as defined in Table Wa.

Table 15a provides 136 compounds of formula (I-2a) wherein A is

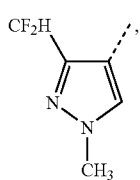

wherein the dashed lines indicate the point of attachment of the group A to the amide group, and $R_1$, X—$R_3$, $R_{5a}$, $R_{5b}$ and $R_{5c}$ are as defined in Table Wa.

Table 16a provides 136 compounds of formula (I-2a) wherein A is

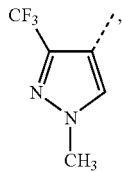

wherein the dashed lines indicate the point of attachment of the group A to the amide group, and $R_1$, X—$R_3$, $R_{5a}$, $R_{5b}$ and $R_{5c}$ are as defined in Table Wa.

Table 17a provides 136 compounds of formula (I-2a) wherein A is

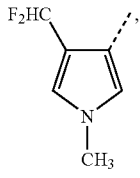

wherein the dashed lines indicate the point of attachment of the group A to the amide group, and $R_1$, X—$R_3$, $R_{5a}$, $R_{5b}$ and $R_{5c}$ are as defined in Table Wa.

Table 18a provides 136 compounds of formula (I-2a) wherein A is

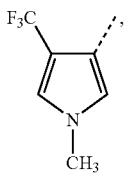

wherein the dashed lines indicate the point of attachment of the group A to the amide group, and $R_1$, X—$R_3$, $R_{5a}$, $R_{5b}$ and $R_{5c}$ are as defined in Table Wa.

Table 19a provides 136 compounds of formula (I-2a) wherein A is

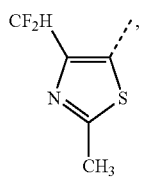

wherein the dashed lines indicate the point of attachment of the group A to the amide group, and $R_1$, X—$R_3$, $R_{5a}$, $R_{5b}$ and $R_{5c}$ are as defined in Table Wa.

Table 20a provides 136 compounds of formula (I-2a) wherein A is

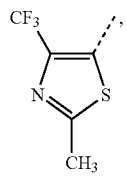

wherein the dashed lines indicate the point of attachment of the group A to the amide group, and $R_1$, X—$R_3$, $R_{5a}$, $R_{5b}$ and $R_{5c}$ are as defined in Table Wa.

Tables 21a to 33a: Compounds of Formula I-3a:

The invention is further illustrated by the preferred individual compounds of formula (I-3a) listed below in Tables 21a to 33a.

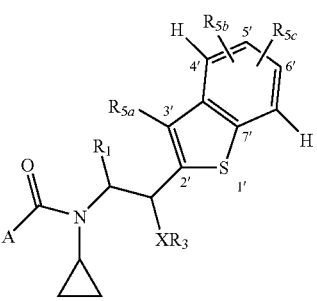

(I-3a)

Each of Tables 21a to 33a, which follow the Table Ya below, comprises 64 compounds of the formula (I-3a) in which $R_1$, X—$R_3$, $R_{5a}$, $R_{5b}$ and $R_{5c}$ have the values given in Table Ya and A has the value given in the relevant Table 21a to 33a. Thus Table 21a corresponds to Table Ya when Ya is 21 and A has the value given under the Table 21a heading, Table 22a corresponds to Table Ya when Ya is 22 and A has the value given under the Table 22a heading, and so on for Tables 23a to 33a.

TABLE Ya

| Compound Number | $R_1$ | $XR_3$ | $R_{5a}$ | $R_{5b}$ | $R_{5c}$ |
|---|---|---|---|---|---|
| Ya.1 | H | OMe | Cl | 5'-Cl | H |
| Ya.2 | Me | OMe | Cl | 5'-Cl | H |
| Ya.3 | H | OEt | Cl | 5'-Cl | H |
| Ya.4 | Me | OEt | Cl | 5'-Cl | H |
| Ya.5 | H | SMe | Cl | 5'-Cl | H |

TABLE Ya-continued

| Compound Number | $R_1$ | $XR_3$ | $R_{5a}$ | $R_{5b}$ | $R_{5c}$ |
|---|---|---|---|---|---|
| Ya.6 | Me | SMe | Cl | 5'-Cl | H |
| Ya.7 | H | SEt | Cl | 5'-Cl | H |
| Ya.8 | Me | SEt | Cl | 5'-Cl | H |
| Ya.9 | H | OMe | Cl | 5'-Br | H |
| Ya.10 | Me | OMe | Cl | 5'-Br | H |
| Ya.11 | H | OEt | Cl | 5'-Br | H |
| Ya.12 | Me | OEt | Cl | 5'-Br | H |
| Ya.13 | H | SMe | Cl | 5'-Br | H |
| Ya.14 | Me | SMe | Cl | 5'-Br | H |
| Ya.15 | H | SEt | Cl | 5'-Br | H |
| Ya.16 | Me | SEt | Cl | 5'-Br | H |
| Ya.17 | H | OMe | Cl | 5'-ethynyl-cyclopropyl | H |
| Ya.18 | Me | OMe | Cl | 5'-ethynyl-cyclopropyl | H |
| Ya.19 | H | OEt | Cl | 5'-ethynyl-cyclopropyl | H |
| Ya.20 | Me | OEt | Cl | 5'-ethynyl-cyclopropyl | H |
| Ya.21 | H | SMe | Cl | 5'-ethynyl-cyclopropyl | H |
| Ya.22 | Me | SMe | Cl | 5'-ethynyl-cyclopropyl | H |
| Ya.23 | H | SEt | Cl | 5'-ethynyl-cyclopropyl | H |
| Ya.24 | Me | SEt | Cl | 5'-ethynyl-cyclopropyl | H |
| Ya.25 | H | OMe | Cl | 5'-(4-chlorophenyl) | H |
| Ya.26 | Me | OMe | Cl | 5'-(4-chlorophenyl) | H |
| Ya.27 | H | OEt | Cl | 5'-(4-chlorophenyl) | H |
| Ya.28 | Me | OEt | Cl | 5'-(4-chlorophenyl) | H |
| Ya.29 | H | SMe | Cl | 5'-(4-chlorophenyl) | H |
| Ya.30 | Me | SMe | Cl | 5'-(4-chlorophenyl) | H |
| Ya.31 | H | SEt | Cl | 5'-(4-chlorophenyl) | H |
| Ya.32 | Me | SEt | Cl | 5'-(4-chlorophenyl) | H |
| Ya.33 | H | OMe | Cl | 6'-Cl | H |
| Ya.34 | Me | OMe | Cl | 6'-Cl | H |
| Ya.35 | H | OEt | Cl | 6'-Cl | H |
| Ya.36 | Me | OEt | Cl | 6'-Cl | H |
| Ya.37 | H | SMe | Cl | 6'-Cl | H |
| Ya.38 | Me | SMe | Cl | 6'-Cl | H |
| Ya.39 | H | SEt | Cl | 6'-Cl | H |
| Ya.40 | Me | SEt | Cl | 6'-Cl | H |
| Ya.41 | H | OMe | Cl | 6'-Br | H |
| Ya.42 | Me | OMe | Cl | 6'-Br | H |
| Ya.43 | H | OEt | Cl | 6'-Br | H |
| Ya.44 | Me | OEt | Cl | 6'-Br | H |
| Ya.45 | H | SMe | Cl | 6'-Br | H |
| Ya.46 | Me | SMe | Cl | 6'-Br | H |
| Ya.47 | H | SEt | Cl | 6'-Br | H |
| Ya.48 | Me | SEt | Cl | 6'-Br | H |
| Ya.49 | H | OMe | Cl | 6'-ethynyl-cyclopropyl | H |
| Ya.50 | Me | OMe | Cl | 6'-ethynyl-cyclopropyl | H |
| Ya.51 | H | OEt | Cl | 6'-ethynyl-cyclopropyl | H |
| Ya.52 | Me | OEt | Cl | 6'-ethynyl-cyclopropyl | H |
| Ya.53 | H | SMe | Cl | 6'-ethynyl-cyclopropyl | H |
| Ya.54 | Me | SMe | Cl | 6'-ethynyl-cyclopropyl | H |
| Ya.55 | H | SEt | Cl | 6'-ethynyl-cyclopropyl | H |
| Ya.56 | Me | SEt | Cl | 6'-ethynyl-cyclopropyl | H |
| Ya.57 | H | OMe | Cl | 6'-(4-chlorophenyl) | H |
| Ya.58 | Me | OMe | Cl | 6'-(4-chlorophenyl) | H |
| Ya.59 | H | OEt | Cl | 6'-(4-chlorophenyl) | H |
| Ya.60 | Me | OEt | Cl | 6'-(4-chlorophenyl) | H |
| Ya.61 | H | SMe | Cl | 6'-(4-chlorophenyl) | H |

TABLE Ya-continued

| Compound Number | R₁ | XR₃ | R₅ₐ | R₅ᵦ | R₅꜀ |
|---|---|---|---|---|---|
| Ya.62 | Me | SMe | Cl | 6'-⟨C₆H₄⟩-Cl | H |
| Ya.63 | H | SEt | Cl | 6'-⟨C₆H₄⟩-Cl | H |
| Ya.64 | Me | SEt | Cl | 6'-⟨C₆H₄⟩-Cl | H |

Table 21a provides 64 compounds of formula (I-3a), wherein A is

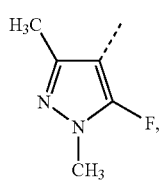

wherein the dashed lines indicate the point of attachment of the group A to the amide group, and $R_1$, X—$R_3$, $R_{5a}$, $R_{5b}$ and $R_{5c}$ are as defined in Table Ya.

Table 22a provides 64 compounds of formula (I-3a) wherein A is

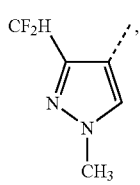

wherein the dashed lines indicate the point of attachment of the group A to the amide group, and $R_1$, X—$R_3$, $R_{5a}$, $R_{5b}$ and $R_{5c}$ are as defined in Table Ya.

Table 23a provides 64 compounds of formula (I-3a) wherein A is

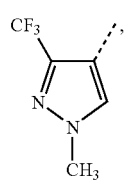

wherein the dashed lines indicate the point of attachment of the group A to the amide group, and $R_1$, X—$R_3$, $R_{5a}$, $R_{5b}$ and $R_{5c}$ are as defined in Table Ya.

Table 24a provides 64 compounds of formula (I-3a) wherein A is

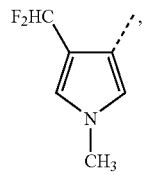

wherein the dashed lines indicate the point of attachment of the group A to the amide group, and $R_1$, X—$R_3$, $R_{5a}$, $R_{5b}$ and $R_{5c}$ are as defined in Table Ya.

Table 25a provides 64 compounds of formula (I-3a) wherein A is

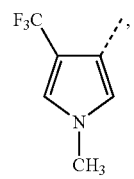

wherein the dashed lines indicate the point of attachment of the group A to the amide group, and $R_1$, X—$R_3$, $R_{5a}$, $R_{5b}$ and $R_{5c}$ are as defined in Table Ya.

Table 26a provides 64 compounds of formula (I-3a) wherein A is

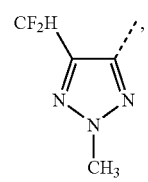

wherein the dashed lines indicate the point of attachment of the group A to the amide group, and $R_1$, X—$R_3$, $R_{5a}$, $R_{5b}$ and $R_{5c}$ are as defined in Table Ya.

Table 27a provides 64 compounds of formula (I-3a) wherein A is

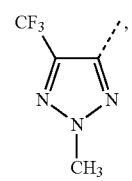

wherein the dashed lines indicate the point of attachment of the group A to the amide group, and $R_1$, X—$R_3$, $R_{5a}$, $R_{5b}$ and $R_{5c}$ are as defined in Table Ya.

Table 28a provides 64 compounds of formula (I-3a) wherein A is

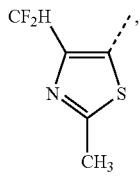

wherein the dashed lines indicate the point of attachment of the group A to the amide group, and $R_1$, $X$—$R_3$, $R_{5a}$, $R_{5b}$ and $R_{5c}$ are as defined in Table Ya.

Table 29a provides 64 compounds of formula (I-3a) wherein A is

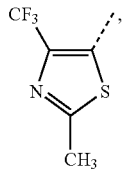

wherein the dashed lines indicate the point of attachment of the group A to the amide group, and $R_1$, $X$—$R_3$, $R_{5a}$, $R_{5b}$ and $R_{5c}$ are as defined in Table Ya.

Table 30a provides 64 compounds of formula (I-3a) wherein A is

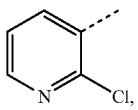

wherein the dashed lines indicate the point of attachment of the group A to the amide group, and $R_1$, $X$—$R_3$, $R_{5a}$, $R_{5b}$ and $R_{5c}$ are as defined in Table Ya.

Table 31a provides 64 compounds of formula (I-3a) wherein A is

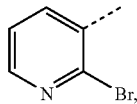

wherein the dashed lines indicate the point of attachment of the group A to the amide group, and $R_1$, $X$—$R_3$, $R_{5a}$, $R_{5b}$ and $R_{5c}$ are as defined in Table.

Table 32a provides 64 compounds of formula (I-3a) wherein A is

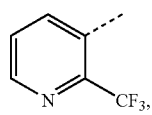

wherein the dashed lines indicate the point of attachment of the group A to the amide group, and $R_1$, $X$—$R_3$, $R_{5a}$, $R_{5b}$ and $R_{5c}$ are as defined in Table Ya.

Table 33a provides 64 compounds of formula (I-3a) wherein A is

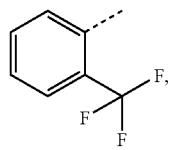

wherein the dashed lines indicate the point of attachment of the group A to the amide group, and $R_1$, $X$—$R_3$, $R_{5a}$, $R_{5b}$ and $R_{5c}$ are as defined in Table Ya.

Formulation Examples for Compounds of Formula I

Example F-1.1 to F-1.2

Emulsifiable Concentrates

| Components | F-1.1 | F-1.2 |
|---|---|---|
| compound of Tables 1 to 33 | 25% | 50% |
| calcium dodecylbenzenesulfonate | 5% | 6% |
| castor oil polyethylene glycol ether (36 mol ethylenoxy units) | 5% | — |
| tributylphenolpolyethylene glycol ether (30 mol ethylenoxy units) | — | 4% |
| cyclohexanone | — | 20% |
| xylene mixture | 65% | 20% |

Emulsions of any desired concentration can be prepared by diluting such concentrates with water.

Example F-2

Emulsifiable concentrate

| Components | F-2 |
|---|---|
| compound of Tables 1 to 33 | 10% |
| octylphenolpolyethylene glycol ether (4 to 5 mol ethylenoxy units) | 3% |
| calcium dodecylbenzenesulfonate | 3% |
| castor oil polyglycol ether (36 mol ethylenoxy units) | 4% |
| cyclohexanone | 30% |
| xylene mixture | 50% |

Emulsions of any desired concentration can be prepared by diluting such concentrates with water.

Examples F-3.1 to F-3.4

Solutions

| Components | F-3.1 | F-3.2 | F-3.3 | F-3.4 |
|---|---|---|---|---|
| compound of Tables 1 to 33 | 80% | 10% | 5% | 95% |
| propylene glycol monomethyl ether | 20% | — | — | — |

-continued

| Components | F-3.1 | F-3.2 | F-3.3 | F-3.4 |
|---|---|---|---|---|
| polyethylene glycol (relative molecular mass: 400 atomic mass units) | — | 70% | — | — |
| N-methylpyrrolid-2-one | — | 20% | — | — |
| epoxidised coconut oil | — | — | 1% | 5% |
| benzin (boiling range: 160-190°) | — | — | 94% | — |

The solutions are suitable for use in the form of microdrops.

Examples F-4.1 to F-4.4

Granulates

| Components | F-4.1 | F-4.2 | F-4.3 | F-4.4 |
|---|---|---|---|---|
| compound of Tables 1 to 33 | 5% | 10% | 8% | 21% |
| kaolin | 94% | — | 79% | 54% |
| highly dispersed silicic acid | 1% | — | 13% | 7% |
| attapulgite | — | 90% | — | 18% |

The novel compound is dissolved in dichloromethane, the solution is sprayed onto the carrier and the solvent is then removed by distillation under vacuum.

Examples F-5.1 and F-5.2

Dusts

| Components | F-5.1 | F-5.2 |
|---|---|---|
| compound of Tables 1 to 33 | 2% | 5% |
| highly dispersed silicic acid | 1% | 5% |
| talcum | 97% | — |
| kaolin | — | 90% |

Ready for use dusts are obtained by intimately mixing all components.

Examples F-6.1 to F-6.3

Wettable Powders

| Components | F-6.1 | F-6.2 | F-6.3 |
|---|---|---|---|
| compound of Tables 1 to 33 | 25% | 50% | 75% |
| sodium lignin sulfonate | 5% | 5% | — |
| sodium lauryl sulfate | 3% | — | 5% |
| sodium diisobutylnaphthalene sulfonate | — | 6% | 10% |
| octylphenolpolyethylene glycol ether (7 to 8 mol ethylenoxy units) | — | 2% | — |
| highly dispersed silicic acid | 5% | 10% | 10% |
| kaolin | 62% | 27% | — |

All components are mixed and the mixture is thoroughly ground in a suitable mill to give wettable powders which can be diluted with water to suspensions of any desired concentration.

Example F7

Flowable Concentrate for Seed Treatment

| | |
|---|---|
| compound of Tables 1 to 33 | 40% |
| propylene glycol | 5% |
| copolymer butanol PO/EO | 2% |
| tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Biological Examples: Fungicidal Actions

Example B-1

Action Against *Botrytis cinerea*/Tomato (*Botrytis* on Tomatoes)

4 week old tomato plants cv. Roter Gnom are treated with the formulated test compound (0.02% active ingredient) in a spray chamber. Two days after application tomato plants are inoculated by spraying a spore suspension ($1 \times 10^5$ conidia/ml) on the test plants. After an incubation period of 4 days at 20° C. and 95% r.h. in a growth chamber the disease incidence is assessed. Compounds 22.2, 22.4, 22.33, 22.34, 22.36, 30.2, 30.4 and 33.2 show good activity in this test (<20% infestation).

Example B-2

Action Against *Uncinula Necator*/Grape (Powdery Mildew on Grape)

5 week old grape seedlings cv. Gutedel are treated with the formulated test compound (0.02% active ingredient) in a spray chamber. One day after application, the grape plants are inoculated by shaking plants infected with grape powdery mildew above the test plants. After an incubation period of 7 days at 26° C. and 60% r.h. under a light regime of 14/10 hours (light/dark) the disease incidence is assessed. Compounds 22.2, 22.4, 22.33, 22.34, 22.36, 25.34, 29.34, 30.4, 30.33, 30.34, 33.2, 33.4, 33.33, 33.34 and 33.36 show good activity in this test (<20% infestation).

Example B-3

Action Against *Puccinia recondita*/Wheat (Brownrust on Wheat)

1 week old wheat plants cv. Arina are treated with the formulated test compound (0.02% active ingredient) in a spray chamber. One day after application, the wheat plants are inoculated by spraying a spore suspension (1×10⁵ uredospores/ml) on the test plants. After an incubation period of 2 days at 20° C. and 95% r.h. the plants are kept in a greenhouse for 8 days at 20° C. and 60% r.h. The disease incidence is assessed 10 days after inoculation. Compounds 22.2, 22.4 and 22.36 show good activity in this test (<20% infestation).

Example B-4

Action Against *Septoria tritici*/Wheat (Septoria Leaf Spot on Wheat)

2 week old wheat plants cv. Riband are treated with the formulated test compound (0.02% active ingredient) in a spray chamber. One day after application, wheat plants are inoculated by spraying a spore suspension (10×10⁵ conidia/ml) on the test plants. After an incubation period of 1 day at 23° C. and 95% r.h., the plants are kept for 16 days at 23° C. and 60% r.h. in a greenhouse. The disease incidence is assessed 18 days after inoculation. Compounds 22.2, 22.4, 22.33, 22.34, 22.36, 25.34, 29.34, 30.2, 30.4, 30.33, 30.34, 33.2, 33.4, 33.33, 33.34 and 33.36 show good activity in this test (<20% infestation).

Example B-5

Action Against *Pyrenophora teres*/Barley (Net Blotch on Barley)

1 week old barley plants cv. Express are treated with the formulated test compound (0.02% active ingredient) in a spray chamber. Two days after application barley plants are inoculated by spraying a spore suspension (3×10⁴ conidia/ml) on the test plants. After an incubation period of 2 days at 20° C. and 95% r.h. plants are kept for 2 days at 20° C. and 60% r.h. in a greenhouse. The disease incidence is assessed 4 days after inoculation. Compounds Compounds 22.2, 22.4, 22.33, 22.34, 22.36, 25.34, 29.34, 30.2, 30.4, 30.33, 30.34, 33.2, 33.4, 33.33, 33.34 and 33.36 show good activity in this test (<20% infestation).

Example B-6

Action Against *Alternaria solani*/Tomato (Early Blight on Tomatoes)

4 week old tomato plants cv. Roter Gnom are treated with the formulated test compound (0.02% active ingredient) in a spray chamber. Two days after application, the tomato plants are inoculated by spraying a spore suspension (2×10⁵ conidia/ml) on the test plants. After an incubation period of 3 days at 20° C. and 95% r.h. in a growth chamber the disease incidence is assessed. Compounds 22.2, 22.4, 22.34, 22.36, 25.34, 29.34, 30.2, 30.4, 30.34, 33.2, 33.4, 33.33, 33.34 and 33.36 show good activity in this test (<20% infestation).

What is claimed is:

1. A compound of the formula I

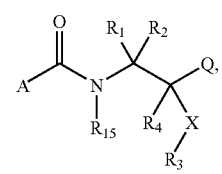

wherein $R_1$, $R_2$ and $R_4$ independently of each other are hydrogen, halogen, $C_1$-$C_4$ alkyl or $C_1$-$C_4$ halogenalkyl;

X is oxygen, sulfur, —N($R_9$)— or —N($R_{10}$)—O—;

$R_9$ and $R_{10}$ independently of each other are hydrogen or $C_1$-$C_6$alkyl;

$R_3$ is $C_1$-$C_6$alkyl or $C_1$-$C_6$haloalkyl;

Q is $Q_1$

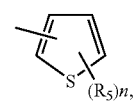

or Q is $Q_2$

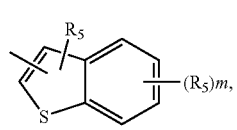

wherein each $R_5$ independently of each other is halogen, $C_1$-$C_4$ alkyl, $C_1$-$C_4$ halogenalkyl, phenyl, halogenphenyl, $C_3$-$C_7$ cycloalkyl acetynyl, phenyl acetynyl or halogenphenyl acetynyl;

n is 1, 2 or 3;

m is 1, 2, 3 or 4;

A is a 5- or 6-membered heterocyclic ring containing one to three heteroatoms, each independently selected from oxygen, nitrogen and sulphur, or a phenyl ring; the heterocyclic ring or the phenyl being substituted by the groups $R_6$, $R_7$ and $R_8$;

$R_6$, $R_7$ and $R_8$ are each, independently, hydrogen, halogen, cyano, nitro, $O_{1-4}$ alkyl, $C_{1-4}$ halogenalkyl, $C_{1-4}$ halogenalkoxy, $C_{1-4}$ alkoxy($C_{1-4}$)alkyl or $C_{1-4}$ halogenalkoxy ($C_{1-4}$)alkyl, provided that at least one of $R_6$, $R_7$ and $R_8$ is not hydrogen;

$R_{15}$ is hydrogen or $C_3$-$C_7$cycloalkyl;

and tautomers and enantiomers of these compounds.

2. A compound of formula I according to claim 1, wherein $R_{15}$ is hydrogen.

3. A compound of formula I according to claim 1, wherein A is a 5-membered heterocyclic ring containing one to three heteroatoms, each independently selected from oxygen, nitrogen and sulphur; the heterocyclic ring being substituted by the groups $R_6$, $R_7$ and $R_8$.

4. A compound of formula I according to claim 1, wherein A is $A_1$

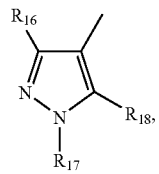

(A₁)

in which $R_{16}$ is halogen, cyano, nitro, $C_1$-$C_4$alkyl, $C_1$-$C_4$halogenalkyl, $C_1$-$C_4$halogenalkoxy, $C_1$-$C_4$alkoxy-$C_1$-$C_4$alkyl or $C_1$-$C_4$halogenalkoxy-$C_1$-$C_4$alkyl;

$R_{17}$ is $C_1$-$C_4$alkyl, $C_1$-$C_4$halogenalkyl, $C_1$-$C_4$halogenalkoxy, $C_1$-$C_4$alkoxy-$C_1$-$C_4$alkyl or $C_1$-$C_4$halogenalkoxy-$C_1$-$C_4$alkyl; and $R_{18}$ is hydrogen, halogen or cyano;

or A is $A_2$

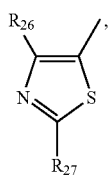

(A₂)

in which $R_{26}$ is halogen, cyano, nitro, $C_1$-$C_4$alkyl, $C_1$-$C_4$halogenalkyl, $C_1$-$C_4$halogenalkoxy, $C_1$-$C_4$alkoxy-$C_1$-$C_4$alkyl or $C_1$-$C_4$halogenalkoxy-$C_1$-$C_4$alkyl; and $R_{27}$ is $C_1$-$C_4$alkyl, $C_1$-$C_4$halogenalkyl, $C_1$-$C_4$halogenalkoxy, $C_1$-$C_4$alkoxy-$C_1$-$C_4$alkyl or $C_1$-$C_4$halogenalkoxy-$C_1$-$C_4$alkyl;

or A is $A_3$

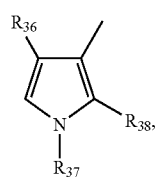

(A₃)

in which $R_{36}$ is halogen, cyano, nitro, $C_1$-$C_4$alkyl, $C_1$-$C_4$halogenalkyl, $C_1$-$C_4$halogenalkoxy, $C_1$-$C_4$alkoxy-$C_1$-$C_4$alkyl or $C_1$-$C_4$halogenalkoxy-$C_1$-$C_4$alkyl;

$R_{37}$ is $C_1$-$C_4$alkyl, $C_1$-$C_4$halogenalkyl, $C_1$-$C_4$halogenalkoxy, $C_1$-$C_4$alkoxy-$C_1$-$C_4$alkyl or $C_1$-$C_4$halogenalkoxy-$C_1$-$C_4$alkyl; and $R_{38}$ is hydrogen, halogen or cyano;

or A is $A_4$

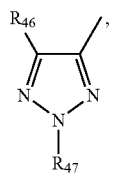

(A₄)

in which $R_{46}$ and $R_{47}$ independently of one another are halogen, cyano, nitro, $C_1$-$C_4$alkyl, $C_1$-$C_4$halogenalkyl, $C_1$-$C_4$halogenalkoxy, $C_1$-$C_4$alkoxy-$C_1$-$C_4$alkyl or $C_1$-$C_4$halogenalkoxy-$C_1$-$C_4$alkyl.

5. A compound of formula I according to claim 4, wherein A is $A_1$.

6. A compound of formula I according to claim 5, wherein $R_{16}$ is $C_1$-$C_4$alkyl or $C_1$-$C_4$halogenalkyl; $R_{17}$ is $C_1$-$C_4$alkyl; and $R_{18}$ is hydrogen or halogen.

7. A compound of formula I according to claim 1, wherein $R_1$, $R_2$ and $R_4$ independently of each other is hydrogen or methyl.

8. A compound of formula I according to claim 1, wherein Q is $Q_2$.

9. A compound of formula I according to claim 1, wherein $Q_2$ is $Q_{2A}$

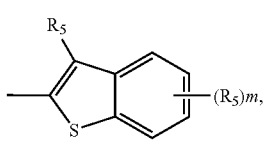

($Q_{2A}$)

wherein each $R_5$ independently of each other is halogen, $C_1$-$C_4$ alkyl, $C_1$-$C_4$ halogenalkyl, phenyl, halogenphenyl, $C_3$-$C_7$ cycloalkyl acetynyl, phenyl acetynyl or halogenphenyl acetynyl; and m is 1, 2, 3 or 4.

10. A compound of formula I according to claim 9, wherein $Q_{2A}$ is $Q_{2A-1}$

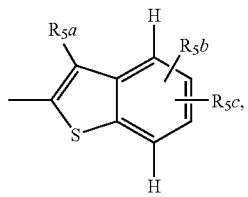

($Q_{2A-1}$)

wherein $R_{5a}$ and $R_{5b}$ are each independently from each other halogen, $C_1$-$C_4$ alkyl, $C_1$-$C_4$ halogenalkyl, phenyl, halogenphenyl, $C_3$-$C_7$ cycloalkyl acetynyl, phenyl acetynyl or halogenphenyl acetynyl; and $R_{5c}$ is hydrogen, halogen, $C_1$-$C_4$ alkyl, $C_1$-$C_4$ halogenalkyl, phenyl, halogenphenyl, $C_3$-$C_7$ cycloalkyl acetynyl, phenyl acetynyl or halogenphenyl acetynyl.

11. A compound of formula I according to claim 10, wherein $R_{5a}$ is halogen; $R_{5b}$ is halogen, phenyl, halogenphenyl, $C_3$-$C_7$ cycloalkyl acetynyl, phenyl acetynyl or halogenphenyl acetynyl; and $R_{5c}$ is hydrogen.

12. A method of controlling or preventing infestation of useful plants by phytopathogenic microorganisms, wherein a compound of formula I according to claim 1 or a composition, comprising this compound as active ingredient, is applied to the plants, to parts thereof or the locus thereof.

13. A composition for controlling and protecting against phytopathogenic microorganisms, comprising a compound of formula I according to claim 1 and an inert carrier.

* * * * *